US010973908B1

(12) United States Patent
Bermudes

(10) Patent No.: US 10,973,908 B1
(45) Date of Patent: Apr. 13, 2021

(54) EXPRESSION OF SARS-COV-2 SPIKE PROTEIN RECEPTOR BINDING DOMAIN IN ATTENUATED SALMONELLA AS A VACCINE

(71) Applicant: David Gordon Bermudes, Woodland Hills, CA (US)

(72) Inventor: David Gordon Bermudes, Woodland Hills, CA (US)

( * ) Notice: Subject to any disclaimer, the term of this patent is extended or adjusted under 35 U.S.C. 154(b) by 0 days.

(21) Appl. No.: 15/931,669

(22) Filed: May 14, 2020

(51) Int. Cl.
| | |
|---|---|
| *A61K 39/215* | (2006.01) |
| *C12N 1/20* | (2006.01) |
| *C12N 15/70* | (2006.01) |
| *A61K 39/108* | (2006.01) |
| *C12R 1/19* | (2006.01) |

(52) U.S. Cl.
CPC ........ *A61K 39/215* (2013.01); *A61K 39/0258* (2013.01); *C12N 1/20* (2013.01); *C12N 15/70* (2013.01); *C12R 1/19* (2013.01)

(58) Field of Classification Search
None
See application file for complete search history.

(56) References Cited

U.S. PATENT DOCUMENTS

| | | |
|---|---|---|
| 4,190,495 A | 2/1980 | Curtiss, III |
| 4,735,801 A | 4/1988 | Stocker |
| 4,888,170 A | 12/1989 | Curtiss, III |
| 4,968,619 A | 11/1990 | Curtiss, III |
| 5,066,596 A | 11/1991 | Manning et al. |
| 5,098,998 A | 3/1992 | Mekalanos et al. |
| 5,143,830 A | 9/1992 | Holland et al. |
| 5,294,441 A | 3/1994 | Curtiss, III |
| 5,330,753 A | 7/1994 | Mekalanos et al. |
| 5,387,744 A | 2/1995 | Curtiss, III et al. |
| 5,424,065 A | 6/1995 | Curtiss, III et al. |
| 5,468,485 A | 11/1995 | Curtiss, III |
| 5,470,719 A | 11/1995 | Meng et al. |
| 5,508,192 A | 4/1996 | Georgiou et al. |
| 5,527,678 A | 6/1996 | Blaser et al. |
| 5,627,067 A | 5/1997 | Siadak et al. |
| 5,628,996 A | 5/1997 | Siadak et al. |
| 5,643,771 A | 7/1997 | Stocker |
| 5,654,184 A | 8/1997 | Curtiss, III et al. |
| 5,656,488 A | 8/1997 | Curtiss, III et al. |
| 5,662,905 A | 9/1997 | Siadak et al. |
| 5,672,345 A | 9/1997 | Curtiss, III |
| 5,679,564 A | 10/1997 | Pace et al. |
| 5,679,880 A | 10/1997 | Curtiss, III et al. |
| 5,686,079 A | 11/1997 | Curtiss, III et al. |
| 5,695,983 A | 12/1997 | Miller et al. |
| 5,717,071 A | 2/1998 | Raff |
| 5,731,196 A | 3/1998 | Miller, III et al. |
| 5,736,367 A | 4/1998 | Haun et al. |
| 5,747,028 A | 5/1998 | Calderwood et al. |
| 5,770,214 A | 6/1998 | Dougan et al. |
| 5,773,007 A | 6/1998 | Penney et al. |
| 5,811,105 A | 9/1998 | Dougan et al. |
| 5,824,502 A | 10/1998 | Honjo et al. |
| 5,824,538 A | 10/1998 | Branstrom et al. |
| 5,830,702 A | 11/1998 | Portnoy et al. |
| 5,837,509 A | 11/1998 | Israelsen et al. |
| 5,837,541 A | 11/1998 | Raff |
| 5,840,483 A | 11/1998 | Curtiss, III |
| 5,843,426 A | 12/1998 | Miller et al. |
| 5,855,879 A | 1/1999 | Curtiss, III |
| 5,855,880 A | 1/1999 | Curtiss, III et al. |
| 5,869,066 A | 2/1999 | Pace et al. |
| 5,874,088 A | 2/1999 | Mekalanos |
| 5,877,159 A | 3/1999 | Powell et al. |
| 5,888,799 A | 3/1999 | Curtiss, III |
| 5,989,868 A | 11/1999 | Harrison et al. |
| 6,024,961 A | 2/2000 | Curtiss, III et al. |
| 6,030,624 A | 2/2000 | Russell et al. |
| 6,051,237 A | 4/2000 | Paterson |
| 6,051,416 A | 4/2000 | Pace et al. |
| 6,077,678 A | 6/2000 | Pace et al. |
| 6,080,849 A | 6/2000 | Bermudes et al. |
| 6,083,715 A | 7/2000 | Georgiou et al. |
| 6,100,388 A | 8/2000 | Casas et al. |

(Continued)

FOREIGN PATENT DOCUMENTS

| | | |
|---|---|---|
| EP | 0973911 | 1/2000 |
| EP | 1270730 | 1/2003 |

(Continued)

OTHER PUBLICATIONS

Sievers et al. 2020 (Clinical Trials Indentifier: NCT04334980; bacTRL-Spike-1; Symvivo Corporation; first posted Apr. 6, 2020; https://www.clinicaltrials.gov/ct2/show/ NCT04334980 (Year: 2020).*
Symvivo's bacTRL product information; 2019 (Year: 2019).*
Diamond et al. 2020 (The Challenges of Vaccine Development against a New Virus during a Pandemic; Cell Host & Microbe; 27: 699-703). (Year: 2020).*
Wang et al. 2020 (An Evidence Based Perspective on mRNA-SARS-CoV-2 Vaccine Development; Medical Science Monitor 26: 2924700 (Year: 2020).*
Ciotti et al. 2019 (COVID-19 Outbreak: An Overview; Chemotherapy 64:215-223; published online Apr. 7, 2020) (Year: 2020).*

*Primary Examiner* — Mary Maille Lyons

(74) *Attorney, Agent, or Firm* — Hoffberg & Associates; Steven M. Hoffberg

(57) ABSTRACT

A live genetically engineered bacterium, comprising a genetically engineered construct comprising a nucleic acid sequence encoding at least one portion of a SARS-CoV-2 antigen, the live genetically engineered bacterium being adapted for administration to a human or animal and colonization of at least one tissue under non-lethal conditions. The antigen is preferably the SARS-CoV-2 spike protein. The nucleic acid sequence preferably includes an associated promoter.

17 Claims, 1 Drawing Sheet

Specification includes a Sequence Listing.

(56) References Cited

U.S. PATENT DOCUMENTS

| | | |
|---|---|---|
| 6,129,917 A | 10/2000 | Potempa et al. |
| 6,130,082 A | 10/2000 | Majarian et al. |
| 6,150,170 A | 11/2000 | Powell et al. |
| 6,153,203 A | 11/2000 | Holmgren et al. |
| 6,177,083 B1 | 1/2001 | Lubitz |
| 6,190,657 B1 | 2/2001 | Pawelek et al. |
| 6,207,167 B1 | 3/2001 | Ou et al. |
| 6,207,648 B1 | 3/2001 | Waxman et al. |
| 6,245,338 B1 | 6/2001 | Kyd et al. |
| 6,254,875 B1 | 7/2001 | Kyd et al. |
| 6,284,477 B1 | 9/2001 | Kyd et al. |
| 6,294,655 B1 | 9/2001 | Ford et al. |
| 6,306,387 B1 | 10/2001 | Galan |
| 6,309,861 B1 | 10/2001 | Ambrosius et al. |
| 6,329,172 B1 | 12/2001 | Rhee et al. |
| 6,337,072 B1 | 1/2002 | Ford et al. |
| 6,339,141 B1 | 1/2002 | Ballinger et al. |
| 6,344,017 B1 | 2/2002 | Teeter |
| 6,365,163 B1 | 4/2002 | Holmgren et al. |
| 6,365,723 B1 | 4/2002 | Blattner et al. |
| 6,365,726 B1 | 4/2002 | Ballinger et al. |
| 6,372,892 B1 | 4/2002 | Ballinger et al. |
| 6,376,281 B1 | 4/2002 | Kohler et al. |
| 6,383,496 B1 | 5/2002 | Curtiss, III et al. |
| 6,410,012 B1 | 6/2002 | Sizemore et al. |
| 6,413,523 B1 | 7/2002 | Clements |
| 6,426,191 B1 | 7/2002 | Ford et al. |
| 6,444,445 B2 | 9/2002 | Nikolich et al. |
| 6,447,784 B1 | 9/2002 | Bermudes et al. |
| 6,455,279 B1 | 9/2002 | Ambrosius et al. |
| 6,471,964 B1 | 10/2002 | Biering et al. |
| 6,475,482 B1 | 11/2002 | Bermudes et al. |
| 6,495,661 B1 | 12/2002 | Glisson et al. |
| 6,500,419 B1 | 12/2002 | Hone et al. |
| 6,506,550 B1 | 1/2003 | Fulton et al. |
| 6,511,666 B1 | 1/2003 | Reynolds et al. |
| 6,531,313 B1 | 3/2003 | Goudsmit et al. |
| 6,537,558 B2 | 3/2003 | Kaniga |
| 6,541,623 B1 | 4/2003 | Ford et al. |
| 6,548,287 B1 | 4/2003 | Powell et al. |
| 6,566,121 B1 | 5/2003 | Jacobs, Jr. et al. |
| 6,593,147 B1 | 7/2003 | Barbet et al. |
| 6,596,509 B1 | 7/2003 | Bauer et al. |
| 6,596,510 B1 | 7/2003 | Lubitz et al. |
| 6,599,509 B2 | 7/2003 | Fox et al. |
| 6,605,697 B1 | 8/2003 | Kwon et al. |
| 6,610,300 B1 | 8/2003 | Segers et al. |
| 6,610,529 B1 | 8/2003 | Curtiss, III et al. |
| 6,635,246 B1 | 10/2003 | Barrett et al. |
| 6,642,027 B2 | 11/2003 | Diaz-Torres |
| 6,653,128 B2 | 11/2003 | Barbet et al. |
| 6,673,569 B1 | 1/2004 | Kurokawa et al. |
| 6,682,729 B1 | 1/2004 | Powell et al. |
| 6,685,935 B1 | 2/2004 | Pawelek et al. |
| 6,719,980 B1 | 4/2004 | Weston et al. |
| 6,737,521 B1 | 5/2004 | Fischetti et al. |
| 6,749,831 B1 | 6/2004 | Bennett-Guerrero et al. |
| 6,752,994 B2 | 6/2004 | Jacobs, Jr. et al. |
| 6,770,632 B1 | 8/2004 | Aghi et al. |
| 6,780,405 B1 | 8/2004 | Curtiss, III et al. |
| 6,798,684 B2 | 9/2004 | Low et al. |
| 6,825,028 B1 | 11/2004 | Von Eichel-Streiber et al. |
| 6,828,121 B2 | 12/2004 | Chen |
| 6,852,512 B2 | 2/2005 | Choi et al. |
| 6,855,814 B2 | 2/2005 | Blattner et al. |
| 6,861,403 B2 | 3/2005 | Sanders |
| 6,863,894 B2 | 3/2005 | Bermudes et al. |
| 6,872,547 B1 | 3/2005 | Curtiss, III |
| 6,887,483 B2 | 5/2005 | Apicella et al. |
| 6,905,691 B1 | 6/2005 | Chatfield et al. |
| 6,913,753 B2 | 7/2005 | Ramachandran et al. |
| 6,916,478 B2 | 7/2005 | Kadurugamuwa et al. |
| 6,916,918 B2 | 7/2005 | Yu et al. |
| 6,919,198 B1 | 7/2005 | Korpela et al. |
| 6,921,659 B2 | 7/2005 | Joly |
| 6,923,958 B2 | 8/2005 | Xiang et al. |
| 6,923,972 B2 | 8/2005 | Bermudes et al. |
| 6,934,176 B2 | 8/2005 | Low et al. |
| 6,962,696 B1 | 11/2005 | Bermudes et al. |
| 6,992,237 B1 | 1/2006 | Habben et al. |
| 6,994,860 B1 | 2/2006 | Ruelle et al. |
| 7,005,129 B1 | 2/2006 | Apicella et al. |
| 7,015,027 B1 | 3/2006 | Redshaw |
| 7,018,835 B2 | 3/2006 | Hone |
| 7,026,155 B2 | 4/2006 | Mahan et al. |
| 7,039,956 B1 | 5/2006 | Hsia |
| 7,045,336 B1 | 5/2006 | Branstrom et al. |
| 7,052,867 B2 | 5/2006 | Kwon et al. |
| 7,056,700 B2 | 6/2006 | Galen |
| 7,056,732 B2 | 6/2006 | Hua et al. |
| 7,063,850 B1 | 6/2006 | Dale |
| 7,070,989 B2 | 7/2006 | Lee et al. |
| 7,079,879 B1 | 7/2006 | Sylvester et al. |
| 7,080,116 B2 | 7/2006 | Purpura |
| 7,083,791 B2 | 8/2006 | Sleeman et al. |
| 7,083,794 B2 | 8/2006 | Curtiss, III et al. |
| 7,084,105 B2 | 8/2006 | Chakrabarty et al. |
| 7,092,803 B2 | 8/2006 | Kapolka et al. |
| 7,092,819 B2 | 8/2006 | Odachi et al. |
| 7,094,410 B2 | 8/2006 | Reisfeld et al. |
| 7,094,579 B2 | 8/2006 | Gray et al. |
| 7,094,941 B2 | 8/2006 | Das et al. |
| 7,095,430 B2 | 8/2006 | Kato et al. |
| 7,095,524 B2 | 8/2006 | Ogawa |
| 7,105,327 B1 | 9/2006 | Kuppusamy et al. |
| 7,108,130 B2 | 9/2006 | Herelier et al. |
| 7,108,139 B2 | 9/2006 | Nguyen |
| 7,108,922 B2 | 9/2006 | Lyu et al. |
| 7,112,434 B2 | 9/2006 | Cannon et al. |
| 7,115,269 B2 | 10/2006 | Darji et al. |
| 7,118,634 B2 | 10/2006 | Goldsteinas et al. |
| 7,119,032 B2 | 10/2006 | Ji et al. |
| 7,125,718 B2 | 10/2006 | Powell et al. |
| 7,127,800 B2 | 10/2006 | Dinan et al. |
| 7,130,192 B2 | 10/2006 | Wang et al. |
| 7,144,580 B2 | 12/2006 | Confer et al. |
| 7,144,982 B2 | 12/2006 | Mayo |
| 7,159,299 B1 | 1/2007 | McMunigal et al. |
| 7,165,470 B2 | 1/2007 | Sakamoto et al. |
| 7,167,720 B2 | 1/2007 | Takahashi et al. |
| 7,183,105 B2 | 2/2007 | Sabbadini et al. |
| 7,195,757 B2 | 3/2007 | Curtiss, III et al. |
| 7,202,059 B2 | 4/2007 | Habermann et al. |
| 7,211,843 B2 | 5/2007 | Low et al. |
| 7,226,588 B2 | 6/2007 | Apicella et al. |
| 7,235,234 B1 | 6/2007 | Branstrom et al. |
| 7,247,296 B2 | 7/2007 | Redshaw |
| 7,264,812 B2 | 9/2007 | Claerebout et al. |
| 7,279,464 B2 | 10/2007 | Xiang et al. |
| 7,291,325 B2 | 11/2007 | Lee et al. |
| 7,341,725 B2 | 3/2008 | Weston et al. |
| 7,341,841 B2 | 3/2008 | Metzger et al. |
| 7,341,860 B2 | 3/2008 | Curtiss, III et al. |
| 7,344,710 B2 | 3/2008 | Dang et al. |
| 7,354,592 B2 | 4/2008 | Bermudes et al. |
| 7,393,525 B2 | 7/2008 | Powell et al. |
| 7,404,963 B2 | 7/2008 | Sotomayor et al. |
| 7,407,790 B2 | 8/2008 | Hone |
| 7,410,788 B2 | 8/2008 | Beckwith et al. |
| 7,425,438 B2 | 9/2008 | Sung et al. |
| 7,452,531 B2 | 11/2008 | Bermudes et al. |
| 7,459,161 B2 | 12/2008 | Galen |
| 7,470,667 B2 | 12/2008 | Luo et al. |
| 7,473,247 B2 | 1/2009 | Mikszta et al. |
| 7,491,528 B2 | 2/2009 | Lee et al. |
| 7,510,717 B2 | 3/2009 | Apicella et al. |
| 7,514,089 B2 | 4/2009 | Bermudes et al. |
| 7,514,415 B2 | 4/2009 | Klinman et al. |
| 7,531,723 B2 | 5/2009 | Habben et al. |
| 7,541,043 B2 | 6/2009 | Kopecko et al. |
| 7,569,219 B2 | 8/2009 | Hone |
| 7,569,552 B2 | 8/2009 | Luo et al. |
| 7,569,682 B2 | 8/2009 | Adler et al. |
| 7,588,767 B2 | 9/2009 | Szalay et al. |

(56) References Cited

U.S. PATENT DOCUMENTS

| | | |
|---|---|---|
| 7,588,771 B2 | 9/2009 | Szalay et al. |
| 7,601,804 B2 | 10/2009 | Nuijten et al. |
| 7,611,712 B2 | 11/2009 | Karp |
| 7,611,883 B2 | 11/2009 | Cranenburgh |
| 7,622,107 B2 | 11/2009 | Horwitz et al. |
| 7,625,572 B2 | 12/2009 | Sun et al. |
| 7,657,380 B2 | 2/2010 | Lazar et al. |
| 7,662,398 B2 | 2/2010 | Szalay et al. |
| 7,666,656 B2 | 2/2010 | Sun et al. |
| 7,687,474 B2 | 3/2010 | Matin et al. |
| 7,691,383 B2 | 4/2010 | Chakrabarty et al. |
| 7,691,393 B2 | 4/2010 | Dubensky, Jr. et al. |
| 7,695,725 B2 | 4/2010 | Dubensky, Jr. et al. |
| 7,700,091 B2 | 4/2010 | Von Eichel-Streiber et al. |
| 7,700,104 B2 | 4/2010 | Hensel et al. |
| 7,718,179 B2 | 5/2010 | Claerebout et al. |
| 7,718,180 B2 | 5/2010 | Karp |
| 7,732,187 B2 | 6/2010 | Cochran et al. |
| 7,736,898 B1 | 6/2010 | Fulton et al. |
| 7,740,835 B2 | 6/2010 | Fujimori et al. |
| 7,754,221 B2 | 7/2010 | Szalay et al. |
| 7,758,876 B2 | 7/2010 | Klinman et al. |
| 7,763,420 B2 | 7/2010 | Stritzker et al. |
| 7,772,386 B1 | 8/2010 | Jungblut et al. |
| 7,776,527 B2 | 8/2010 | Hsu et al. |
| 7,786,288 B2 | 8/2010 | Karp |
| 7,790,177 B2 | 9/2010 | Karp |
| 7,794,734 B2 | 9/2010 | Ayalew et al. |
| 7,803,531 B2 | 9/2010 | Fulton et al. |
| 7,803,990 B2 | 9/2010 | Abbitt |
| 7,807,184 B2 | 10/2010 | Vermeij |
| 7,807,456 B2 | 10/2010 | Cochran et al. |
| 7,820,184 B2 | 10/2010 | Stritzker et al. |
| 7,829,104 B2 | 11/2010 | Sun et al. |
| 7,833,775 B2 | 11/2010 | Dubensky, Jr. et al. |
| 7,842,289 B2 | 11/2010 | Dubensky, Jr. et al. |
| 7,842,290 B2 | 11/2010 | Holden |
| 7,850,958 B2 | 12/2010 | Hone |
| 7,850,970 B2 | 12/2010 | Shapiro |
| 7,871,604 B1 | 1/2011 | Curtiss, III et al. |
| 7,871,815 B2 | 1/2011 | Sabbadini et al. |
| 7,871,816 B2 | 1/2011 | Sung et al. |
| 7,887,816 B2 | 2/2011 | Feldman et al. |
| 7,915,218 B2 | 3/2011 | Capecchi et al. |
| 7,919,081 B2 | 4/2011 | Maier et al. |
| 7,927,606 B2 | 4/2011 | Dubensky, Jr. et al. |
| 7,930,107 B2 | 4/2011 | Lazar et al. |
| 7,939,319 B2 | 5/2011 | Polack et al. |
| 7,951,386 B2 | 5/2011 | Chang |
| 7,951,786 B2 | 5/2011 | Klinman et al. |
| 7,955,600 B2 | 6/2011 | Hensel et al. |
| 7,960,518 B2 | 6/2011 | Throsby et al. |
| 7,972,604 B2 | 7/2011 | Cochran et al. |
| 7,985,573 B2 | 7/2011 | Yacoby et al. |
| 7,993,651 B2 | 8/2011 | Hanke et al. |
| 7,998,461 B2 | 8/2011 | Forbes et al. |
| 8,008,283 B2 | 8/2011 | Hochman et al. |
| 8,012,466 B2 | 9/2011 | Morita et al. |
| 8,021,662 B2 | 9/2011 | Szalay et al. |
| 8,021,848 B2 | 9/2011 | Straus |
| 8,034,359 B2 | 10/2011 | Gunn |
| 8,043,857 B2 | 10/2011 | Sun et al. |
| 8,048,428 B2 | 11/2011 | Reisfeld et al. |
| 8,049,000 B2 | 11/2011 | Helentjaris et al. |
| 8,053,181 B2 | 11/2011 | Lewinsohn et al. |
| 8,053,421 B2 | 11/2011 | Luo et al. |
| 8,066,987 B2 | 11/2011 | Moore et al. |
| 8,071,084 B2 | 12/2011 | Kopecko et al. |
| 8,071,319 B2 | 12/2011 | Metzger et al. |
| 8,076,099 B2 | 12/2011 | Chambers et al. |
| 8,101,396 B2 | 1/2012 | Sabbadini et al. |
| 8,114,409 B2 | 2/2012 | Weston et al. |
| 8,114,414 B2 | 2/2012 | Paterson et al. |
| 8,124,068 B2 | 2/2012 | Horwitz et al. |
| 8,124,408 B2 | 2/2012 | Cai et al. |
| 8,133,493 B2 | 3/2012 | Curtiss, III |
| 8,137,904 B2 | 3/2012 | Szalay et al. |
| 8,147,820 B2 | 4/2012 | Hawke et al. |
| 8,168,421 B2 | 5/2012 | Quinn et al. |
| 8,173,773 B2 | 5/2012 | He et al. |
| 8,187,610 B2 | 5/2012 | Waller et al. |
| 8,198,430 B2 | 6/2012 | Prior et al. |
| 8,202,516 B2 | 6/2012 | Padmanabhan et al. |
| 8,207,228 B2 | 6/2012 | Mayo et al. |
| 8,211,431 B2 | 7/2012 | Throsby et al. |
| 8,221,769 B2 | 7/2012 | Szalay et al. |
| 8,227,584 B2 | 7/2012 | Claerebout et al. |
| 8,241,623 B1 | 8/2012 | Bermudes |
| 8,241,631 B2 | 8/2012 | Throsby et al. |
| 8,241,637 B2 | 8/2012 | Reisfeld et al. |
| 8,257,713 B2 | 9/2012 | Poobalane et al. |
| 8,273,361 B2 | 9/2012 | Reed et al. |
| 8,282,919 B2 | 10/2012 | Eisenstark et al. |
| 8,287,883 B2 | 10/2012 | Dubensky, Jr. et al. |
| 8,288,359 B2 | 10/2012 | Klinman et al. |
| 8,318,661 B2 | 11/2012 | Ny et al. |
| 8,323,668 B2 | 12/2012 | Fleckenstein |
| 8,323,959 B2 | 12/2012 | Szalay et al. |
| 8,329,685 B1 | 12/2012 | Meyer |
| 8,337,832 B2 | 12/2012 | Kopecko et al. |
| 8,337,861 B2 | 12/2012 | Paterson et al. |
| 8,343,509 B2 | 1/2013 | Stritzker et al. |
| 8,343,512 B2 | 1/2013 | Reed et al. |
| 8,349,586 B1 | 1/2013 | Hamer |
| 8,357,486 B2 | 1/2013 | Stritzker et al. |
| 8,357,533 B2 | 1/2013 | Cai et al. |
| 8,361,707 B2 | 1/2013 | Lewinsohn et al. |
| 8,367,055 B2 | 2/2013 | Talaat et al. |
| 8,399,618 B2 | 3/2013 | Lazar et al. |
| 8,440,207 B2 | 5/2013 | Bermudes |
| 8,445,254 B2 | 5/2013 | Curtiss, III et al. |
| 8,445,426 B2 | 5/2013 | De Vos et al. |
| 8,445,662 B2 | 5/2013 | He et al. |
| 8,460,666 B2 | 6/2013 | Throsby et al. |
| 8,465,755 B2 | 6/2013 | Curtiss, III et al. |
| 8,470,551 B2 | 6/2013 | Sung et al. |
| 8,481,055 B2 | 7/2013 | Klinman et al. |
| 8,501,198 B2 | 8/2013 | Gunn |
| 8,524,220 B1 | 9/2013 | Bermudes |
| 8,551,471 B2 | 10/2013 | Filutowicz et al. |
| 8,551,497 B2 | 10/2013 | Quinn et al. |
| 8,557,789 B2 | 10/2013 | Klinman et al. |
| 8,568,707 B2 | 10/2013 | Szalay et al. |
| 8,580,280 B2 | 11/2013 | Dominowski et al. |
| 8,586,022 B2 | 11/2013 | Szalay et al. |
| 8,591,862 B2 | 11/2013 | Brahmbhatt et al. |
| 8,604,178 B2 | 12/2013 | Bottje et al. |
| 8,609,114 B2 | 12/2013 | Reed |
| 8,623,350 B1 | 1/2014 | Bermudes |
| 8,628,776 B2 | 1/2014 | Throsby et al. |
| 8,632,783 B2 | 1/2014 | Bagnoli et al. |
| 8,633,305 B2 | 1/2014 | Shapiro |
| 8,642,257 B2 | 2/2014 | Szalay et al. |
| 8,642,656 B2 | 2/2014 | Mayo et al. |
| 8,647,642 B2 | 2/2014 | Bermudes |
| 8,658,350 B2 | 2/2014 | Lewinsohn et al. |
| 8,663,634 B2 | 3/2014 | Koenig et al. |
| 8,663,940 B2 | 3/2014 | Granoff et al. |
| 8,669,355 B2 | 3/2014 | Poobalane et al. |
| 8,673,311 B2 | 3/2014 | Cutting et al. |
| 8,679,505 B2 | 3/2014 | Bagnoli et al. |
| 8,685,939 B2 | 4/2014 | Wei et al. |
| 8,703,153 B2 | 4/2014 | Telfer et al. |
| 8,715,641 B2 | 5/2014 | Filutowicz et al. |
| 8,715,929 B2 | 5/2014 | Benghezal et al. |
| 8,716,254 B2 | 5/2014 | Xiang et al. |
| 8,716,343 B2 | 5/2014 | Mayo et al. |
| 8,722,064 B2 | 5/2014 | Reed et al. |
| 8,722,668 B2 | 5/2014 | Hochman |
| 8,734,779 B2 | 5/2014 | Hamaji et al. |
| 8,748,150 B2 | 6/2014 | Padmanabhan et al. |
| 8,758,766 B2 | 6/2014 | Oloo et al. |
| 8,771,669 B1 | 7/2014 | Bermudes |
| 8,772,013 B2 | 7/2014 | Brahmbhatt et al. |

(56) References Cited

U.S. PATENT DOCUMENTS

| | | |
|---|---|---|
| 8,778,683 B2 | 7/2014 | Nano |
| 8,784,829 B2 | 7/2014 | Morsey et al. |
| 8,784,836 B2 | 7/2014 | Szalay et al. |
| 8,790,909 B2 | 7/2014 | Benghezal et al. |
| 8,822,194 B2 | 9/2014 | Zhao et al. |
| 8,828,681 B2 | 9/2014 | Bell, III et al. |
| 8,840,908 B2 | 9/2014 | Reed et al. |
| 8,853,382 B2 | 10/2014 | Hammarstrom et al. |
| 8,859,256 B2 | 10/2014 | Szalay et al. |
| 8,877,212 B2 | 11/2014 | Robinson et al. |
| 8,883,147 B2 | 11/2014 | Lazar et al. |
| 8,889,121 B2 | 11/2014 | Curtiss, III et al. |
| 8,889,150 B2 | 11/2014 | Malouin et al. |
| 8,895,062 B2 | 11/2014 | De Leeuw et al. |
| 8,916,372 B2 | 12/2014 | Bereta et al. |
| 8,926,993 B2 | 1/2015 | Dubensky, Jr. et al. |
| 8,937,074 B2 | 1/2015 | Meyer |
| 8,951,531 B2 | 2/2015 | Oloo et al. |
| 8,956,618 B2 | 2/2015 | Berghman et al. |
| 8,956,621 B2 | 2/2015 | Paterson et al. |
| 8,956,859 B1 | 2/2015 | Bermudes |
| 8,961,989 B2 | 2/2015 | Lewinsohn et al. |
| 8,980,279 B2 | 3/2015 | Gunn et al. |
| 8,992,943 B2 | 3/2015 | Kopecko et al. |
| 9,005,665 B2 | 4/2015 | Gourapura et al. |
| 9,011,870 B2 | 4/2015 | Leenhouts et al. |
| 9,012,213 B2 | 4/2015 | Fruehauf et al. |
| 9,017,986 B2 | 4/2015 | Sabbadini et al. |
| 9,023,635 B2 | 5/2015 | Bayer et al. |
| 9,040,059 B2 | 5/2015 | Curtiss, III et al. |
| 9,040,233 B2 | 5/2015 | Lewinsohn et al. |
| 9,045,528 B2 | 6/2015 | Ruker et al. |
| 9,045,742 B2 | 6/2015 | Curtiss, III et al. |
| 9,050,285 B2 | 6/2015 | Curtiss, III et al. |
| 9,050,319 B2 | 6/2015 | Maj et al. |
| 9,051,574 B2 | 6/2015 | Galen et al. |
| 9,056,909 B2 | 6/2015 | Chu et al. |
| 9,062,297 B2 | 6/2015 | Curtiss, III et al. |
| 9,068,187 B1 | 6/2015 | Bermudes |
| 9,107,864 B2 | 8/2015 | Gunn |
| 9,140,698 B2 | 9/2015 | Orth et al. |
| 9,161,974 B2 | 10/2015 | Dubensky et al. |
| 9,163,219 B2 | 10/2015 | Curtiss, III et al. |
| 9,169,302 B2 | 10/2015 | Carboulec et al. |
| 9,173,930 B2 | 11/2015 | Lewinsohn et al. |
| 9,173,935 B2 | 11/2015 | Maj et al. |
| 9,173,936 B2 | 11/2015 | Maj et al. |
| 9,180,183 B2 | 11/2015 | Maj et al. |
| 9,181,546 B2 | 11/2015 | Li et al. |
| 9,198,960 B2 | 12/2015 | Dubensky, Jr. et al. |
| 9,200,251 B1 | 12/2015 | Bermudes |
| 9,200,289 B1 | 12/2015 | Bermudes |
| 9,205,142 B2 | 12/2015 | Bagnoli et al. |
| 9,220,764 B2 | 12/2015 | Talaat et al. |
| 9,248,177 B2 | 2/2016 | Tang et al. |
| 9,255,149 B2 | 2/2016 | Himmler et al. |
| 9,255,283 B2 | 2/2016 | Curtiss, III et al. |
| 9,265,804 B2 | 2/2016 | Newman |
| 9,267,108 B2 | 2/2016 | Giacalone |
| 9,289,481 B2 | 3/2016 | Ramachandran et al. |
| 9,297,015 B2 | 3/2016 | Curtiss, III et al. |
| 9,303,264 B2 | 4/2016 | Curtiss et al. |
| 9,309,493 B2 | 4/2016 | Ilg et al. |
| 9,315,817 B2 | 4/2016 | Bermudes |
| 9,320,787 B2 | 4/2016 | Gunn |
| 9,320,788 B2 | 4/2016 | Gunn |
| 9,333,251 B2 | 5/2016 | Kopecko et al. |
| 9,339,533 B2 | 5/2016 | Beck et al. |
| 9,358,283 B2 | 6/2016 | Corbeil et al. |
| 9,364,528 B1 | 6/2016 | Giuliani et al. |
| 9,365,625 B1 | 6/2016 | Bermudes |
| 9,376,686 B2 | 6/2016 | Campos-Neto et al. |
| 9,408,880 B2 | 8/2016 | Kovarik et al. |
| 9,415,077 B2 | 8/2016 | Alonso et al. |
| 9,415,098 B2 | 8/2016 | Lubenau |
| 9,421,252 B2 | 8/2016 | Bermudes |
| 9,428,572 B2 | 8/2016 | Throsby et al. |
| 9,441,204 B2 | 9/2016 | Voorhees et al. |
| 9,453,227 B2 | 9/2016 | Diamond et al. |
| 9,457,074 B2 | 10/2016 | Gourapura et al. |
| 9,457,077 B2 | 10/2016 | Kovarik et al. |
| 9,463,238 B2 | 10/2016 | Chaplin et al. |
| 9,474,831 B2 | 10/2016 | Boyden et al. |
| 9,480,740 B2 | 11/2016 | Reed et al. |
| 9,481,884 B2 | 11/2016 | Li |
| 9,481,888 B2 | 11/2016 | Curtiss, III et al. |
| 9,486,513 B1 | 11/2016 | Bermudes |
| 9,487,577 B2 | 11/2016 | Schwarz et al. |
| 9,492,534 B2 | 11/2016 | Szalay et al. |
| 9,499,606 B2 | 11/2016 | Shapiro |
| 9,504,750 B2 | 11/2016 | Harel et al. |
| 9,506,922 B2 | 11/2016 | Lewinsohn et al. |
| 9,526,778 B2 | 12/2016 | Alonso et al. |
| 9,529,005 B2 | 12/2016 | Orth et al. |
| 9,539,313 B2 | 1/2017 | Sad et al. |
| 9,540,407 B2 | 1/2017 | Maj et al. |
| 9,546,199 B2 | 1/2017 | Oloo et al. |
| 9,549,956 B2 | 1/2017 | Fujiwara et al. |
| 9,556,442 B2 | 1/2017 | Le Gouellec et al. |
| 9,561,270 B2 | 2/2017 | Kohler et al. |
| 9,562,080 B2 | 2/2017 | Urbanowicz et al. |
| 9,562,837 B2 | 2/2017 | Link |
| 9,566,321 B2 | 2/2017 | Giacalone |
| 9,566,322 B2 | 2/2017 | Malouin et al. |
| 9,567,375 B2 | 2/2017 | Luo et al. |
| 9,580,478 B2 | 2/2017 | Nano |
| 9,580,718 B2 | 2/2017 | Curtiss, III et al. |
| 9,592,283 B2 | 3/2017 | Kolander et al. |
| 9,593,339 B1 | 3/2017 | Bermudes |
| 9,597,379 B1 | 3/2017 | Bermudes |
| 9,598,697 B2 | 3/2017 | Curtiss, III et al. |
| 9,603,799 B2 | 3/2017 | Sorayya et al. |
| 9,610,342 B2 | 4/2017 | Giuliani et al. |
| 9,616,114 B1 | 4/2017 | Bermudes |
| 9,622,486 B2 | 4/2017 | Padmanabhan et al. |
| 9,636,386 B2 | 5/2017 | Husseiny Elsayed et al. |
| 9,642,881 B2 | 5/2017 | Honda et al. |
| 9,642,904 B2 | 5/2017 | Bagnoli et al. |
| 9,649,345 B2 | 5/2017 | Honda et al. |
| 9,651,559 B2 | 5/2017 | Himmler et al. |
| 9,655,815 B2 | 5/2017 | Xiang et al. |
| 9,657,085 B1 | 5/2017 | Bermudes |
| 9,657,327 B2 | 5/2017 | Metzger et al. |
| 9,662,385 B2 | 5/2017 | Dominowski et al. |
| 9,663,758 B2 | 5/2017 | Talaat |
| 9,670,270 B2 | 6/2017 | Sabbadini et al. |
| 9,695,229 B2 | 7/2017 | Shapiro |
| 9,714,426 B2 | 7/2017 | Fruehauf et al. |
| 9,717,782 B2 | 8/2017 | Lewinsohn et al. |
| 9,730,996 B2 | 8/2017 | Gauduin et al. |
| 9,737,592 B1 | 8/2017 | Bermudes et al. |
| 9,737,601 B2 | 8/2017 | Schwarz et al. |
| 9,739,773 B1 | 8/2017 | Bermudes |
| 9,750,802 B2 | 9/2017 | Kovarik et al. |
| 9,758,572 B2 | 9/2017 | Schwarz et al. |
| 9,764,021 B2 | 9/2017 | Ilg et al. |
| 9,775,896 B2 | 10/2017 | Gunn |
| 9,795,641 B2 | 10/2017 | Nardelli Haefliger et al. |
| 9,796,762 B2 | 10/2017 | Kelly et al. |
| 9,801,930 B2 | 10/2017 | Ramachandran et al. |
| 9,808,517 B2 | 11/2017 | Putnam et al. |
| 9,814,772 B2 | 11/2017 | Reed et al. |
| 9,827,305 B2 | 11/2017 | Qiao et al. |
| 9,844,592 B2 | 12/2017 | Blander et al. |
| 9,845,342 B2 | 12/2017 | Thompson et al. |
| 9,855,336 B2 | 1/2018 | O'Connell et al. |
| 9,856,311 B2 | 1/2018 | Ruker et al. |
| 9,867,785 B2 | 1/2018 | Brahmbhatt et al. |
| 9,872,898 B2 | 1/2018 | Gourapura et al. |
| 9,878,023 B1 | 1/2018 | Bermudes |
| 9,878,024 B2 | 1/2018 | Dubensky, Jr. et al. |
| 9,878,043 B2 | 1/2018 | Brahmbhatt et al. |
| 9,884,108 B2 | 2/2018 | Campos-Neto et al. |
| 9,885,051 B2 | 2/2018 | Curtiss, III et al. |

(56) References Cited

U.S. PATENT DOCUMENTS

| | | |
|---|---|---|
| 9,889,165 B2 | 2/2018 | Taylor et al. |
| 9,901,082 B2 | 2/2018 | Flavell et al. |
| 9,907,755 B2 | 3/2018 | Kabadi et al. |
| 9,907,845 B2 | 3/2018 | Reed et al. |
| 9,913,893 B2 | 3/2018 | Berghman et al. |
| 9,925,257 B2 | 3/2018 | Campos-Neto et al. |
| 9,950,063 B2 | 4/2018 | Reed et al. |
| 9,951,340 B2 | 4/2018 | Lesser et al. |
| 9,986,724 B2 | 6/2018 | Flavell et al. |
| 9,987,355 B2 | 6/2018 | Reed et al. |
| 9,994,809 B2 | 6/2018 | Bhatia et al. |
| 9,999,660 B2 | 6/2018 | Mueller et al. |
| 10,087,451 B2 | 10/2018 | Bermudes |
| 10,141,626 B2 | 11/2018 | Tan et al. |
| 10,188,722 B2 | 1/2019 | Bermudes |
| 10,286,051 B1 | 5/2019 | Bermudes |
| 2001/0014673 A1 | 8/2001 | Nikolich et al. |
| 2002/0025325 A1 | 2/2002 | Chu |
| 2002/0026655 A1 | 2/2002 | Bermudes |
| 2002/0028215 A1 | 3/2002 | Kadurugamuwa |
| 2002/0044938 A1 | 4/2002 | Fox |
| 2002/0068068 A1 | 6/2002 | Mahan |
| 2002/0076417 A1 | 6/2002 | Mahan |
| 2002/0077272 A1 | 6/2002 | Mahan |
| 2002/0081317 A1 | 6/2002 | Mahan |
| 2002/0086032 A1 | 7/2002 | Mahan et al. |
| 2002/0086332 A1 | 7/2002 | Mahan et al. |
| 2002/0090376 A1 | 7/2002 | Kaniga et al. |
| 2002/0102242 A1 | 8/2002 | Briles et al. |
| 2002/0132789 A1 | 9/2002 | Barbet et al. |
| 2002/0146430 A1 | 10/2002 | Galen |
| 2002/0151063 A1 | 10/2002 | Lasham et al. |
| 2002/0151462 A1 | 10/2002 | Lissolo |
| 2002/0156009 A1 | 10/2002 | Ballinger et al. |
| 2002/0176848 A1 | 11/2002 | Sizemore et al. |
| 2003/0008839 A1 | 1/2003 | van Rooij et al. |
| 2003/0009015 A1 | 1/2003 | Ulrich et al. |
| 2003/0017162 A1 | 1/2003 | Warren et al. |
| 2003/0022835 A1 | 1/2003 | Watson et al. |
| 2003/0023075 A1 | 1/2003 | Blattner et al. |
| 2003/0031628 A1 | 2/2003 | Zhao et al. |
| 2003/0036644 A1 | 2/2003 | Ulrich |
| 2003/0045492 A1 | 3/2003 | Tang et al. |
| 2003/0059400 A1 | 3/2003 | Szalay |
| 2003/0065039 A1 | 4/2003 | Kharazmi et al. |
| 2003/0068328 A1 | 4/2003 | Vladoianu et al. |
| 2003/0100100 A1 | 5/2003 | Jacobs, Jr. et al. |
| 2003/0108562 A1 | 6/2003 | Hanke et al. |
| 2003/0108957 A1 | 6/2003 | Otvos et al. |
| 2003/0109026 A1 | 6/2003 | Bermudes et al. |
| 2003/0113293 A1 | 6/2003 | Bermudes et al. |
| 2003/0124516 A1 | 7/2003 | Chung et al. |
| 2003/0125278 A1 | 7/2003 | Tang et al. |
| 2003/0130827 A1 | 7/2003 | Bentzien et al. |
| 2003/0143676 A1 | 7/2003 | Strachan et al. |
| 2003/0152589 A1 | 8/2003 | Ramachandran et al. |
| 2003/0153527 A1 | 8/2003 | Powell et al. |
| 2003/0157637 A1 | 8/2003 | Reynolds et al. |
| 2003/0166099 A1 | 9/2003 | Sabbadini et al. |
| 2003/0166279 A1 | 9/2003 | Sabbadini et al. |
| 2003/0170211 A1 | 9/2003 | Goudsmit et al. |
| 2003/0170276 A1 | 9/2003 | Bermudes et al. |
| 2003/0170613 A1 | 9/2003 | Straus |
| 2003/0176377 A1 | 9/2003 | Xiang et al. |
| 2003/0180260 A1 | 9/2003 | Clancy et al. |
| 2003/0180304 A1 | 9/2003 | Ullrich et al. |
| 2003/0180320 A1 | 9/2003 | Darji et al. |
| 2003/0185802 A1 | 10/2003 | Reisfeld et al. |
| 2003/0186908 A1 | 10/2003 | Goldway |
| 2003/0190601 A1 | 10/2003 | Sabbadini et al. |
| 2003/0190683 A1 | 10/2003 | Sabbadini et al. |
| 2003/0190749 A1 | 10/2003 | Surber et al. |
| 2003/0194714 A1 | 10/2003 | Sabbadini et al. |
| 2003/0194755 A1 | 10/2003 | Schnabel et al. |
| 2003/0194798 A1 | 10/2003 | Surber et al. |
| 2003/0198995 A1 | 10/2003 | Sabbadini et al. |
| 2003/0198996 A1 | 10/2003 | Surber et al. |
| 2003/0199005 A1 | 10/2003 | Sabbadini et al. |
| 2003/0199088 A1 | 10/2003 | Sabbadini et al. |
| 2003/0199089 A1 | 10/2003 | Surber et al. |
| 2003/0202937 A1 | 10/2003 | Sabbadini et al. |
| 2003/0203411 A1 | 10/2003 | Sabbadini et al. |
| 2003/0203481 A1 | 10/2003 | Surber et al. |
| 2003/0207833 A1 | 11/2003 | Berkley et al. |
| 2003/0211086 A1 | 11/2003 | Berkley et al. |
| 2003/0211103 A1 | 11/2003 | Buyse et al. |
| 2003/0211461 A1 | 11/2003 | Kariv et al. |
| 2003/0211476 A1 | 11/2003 | O'Mahony et al. |
| 2003/0211599 A1 | 11/2003 | Sabbadini et al. |
| 2003/0219408 A1 | 11/2003 | Sabbadini et al. |
| 2003/0219888 A1 | 11/2003 | Segall et al. |
| 2003/0224369 A1 | 12/2003 | Surber et al. |
| 2003/0224444 A1 | 12/2003 | Sabbadini et al. |
| 2003/0232335 A1 | 12/2003 | Surber et al. |
| 2003/0235577 A1 | 12/2003 | Shapiro et al. |
| 2004/0005695 A1 | 1/2004 | Miksch et al. |
| 2004/0005700 A1 | 1/2004 | Surber et al. |
| 2004/0009540 A1 | 1/2004 | Soohoo et al. |
| 2004/0009936 A1 | 1/2004 | Tang et al. |
| 2004/0013658 A1 | 1/2004 | Fulton et al. |
| 2004/0013689 A1 | 1/2004 | Kadurugamuwa et al. |
| 2004/0023310 A1 | 2/2004 | Kariv et al. |
| 2004/0033539 A1 | 2/2004 | Schnabel et al. |
| 2004/0037117 A1 | 2/2004 | Low et al. |
| 2004/0042274 A1 | 3/2004 | Low et al. |
| 2004/0052817 A1 | 3/2004 | Geldhof et al. |
| 2004/0053209 A1 | 3/2004 | Kariv et al. |
| 2004/0054142 A1 | 3/2004 | Cassart et al. |
| 2004/0058849 A1 | 3/2004 | Sleeman et al. |
| 2004/0077067 A1 | 4/2004 | Sin et al. |
| 2004/0115174 A1 | 6/2004 | Gilboa et al. |
| 2004/0121307 A1 | 6/2004 | Schnabel et al. |
| 2004/0121474 A1 | 6/2004 | SooHoo et al. |
| 2004/0126871 A1 | 7/2004 | Barbet et al. |
| 2004/0131641 A1 | 7/2004 | Mikszta et al. |
| 2004/0132678 A1 | 7/2004 | Hone |
| 2004/0137003 A1 | 7/2004 | Curtiss, III |
| 2004/0156865 A1 | 8/2004 | Confer et al. |
| 2004/0192631 A1 | 9/2004 | Xiang et al. |
| 2004/0202648 A1 | 10/2004 | Cabezon et al. |
| 2004/0202663 A1 | 10/2004 | Hu et al. |
| 2004/0213804 A1 | 10/2004 | Michon et al. |
| 2004/0219169 A1 | 11/2004 | Bermudes et al. |
| 2004/0228877 A1 | 11/2004 | Dubensky, Jr. et al. |
| 2004/0229338 A1 | 11/2004 | King |
| 2004/0234455 A1 | 11/2004 | Szalay |
| 2004/0237147 A1 | 11/2004 | Habben et al. |
| 2004/0258703 A1 | 12/2004 | Glenn et al. |
| 2004/0258707 A1 | 12/2004 | Weston et al. |
| 2004/0265337 A1 | 12/2004 | Zsebo et al. |
| 2004/0266003 A1 | 12/2004 | Powell et al. |
| 2005/0008618 A1 | 1/2005 | Kaufman et al. |
| 2005/0009750 A1 | 1/2005 | Sleeman et al. |
| 2005/0010032 A1 | 1/2005 | Hardham et al. |
| 2005/0026866 A1 | 2/2005 | Pawelek |
| 2005/0036987 A1 | 2/2005 | Pawelek et al. |
| 2005/0042755 A1 | 2/2005 | Von Eichel-Streiber et al. |
| 2005/0048076 A1 | 3/2005 | Apicella et al. |
| 2005/0052892 A1 | 3/2005 | Low et al. |
| 2005/0064526 A1 | 3/2005 | Ulrich et al. |
| 2005/0069491 A1 | 3/2005 | Szalay et al. |
| 2005/0075298 A1 | 4/2005 | Chen et al. |
| 2005/0106151 A1 | 5/2005 | Shapiro |
| 2005/0106176 A1 | 5/2005 | Curtis et al. |
| 2005/0112139 A1 | 5/2005 | Karp |
| 2005/0112140 A1 | 5/2005 | Karp |
| 2005/0112642 A1 | 5/2005 | Sleeman et al. |
| 2005/0118193 A1 | 6/2005 | Andino-Pavlovsky et al. |
| 2005/0129711 A1 | 6/2005 | Ramachandran et al. |
| 2005/0163791 A1 | 7/2005 | Adler et al. |
| 2005/0175630 A1 | 8/2005 | Raz et al. |
| 2005/0180985 A9 | 8/2005 | Vladoianu et al. |
| 2005/0214317 A1 | 9/2005 | Karp |
| 2005/0214318 A1 | 9/2005 | Karp |

(56) References Cited

U.S. PATENT DOCUMENTS

| | | |
|---|---|---|
| 2005/0222057 A1 | 10/2005 | Brahmbhatt et al. |
| 2005/0229274 A1 | 10/2005 | Habben et al. |
| 2005/0232937 A1 | 10/2005 | Willemsen et al. |
| 2005/0233408 A1 | 10/2005 | Pouwels et al. |
| 2005/0249706 A1 | 11/2005 | Bermudes et al. |
| 2005/0249752 A1 | 11/2005 | Sung et al. |
| 2005/0255088 A1 | 11/2005 | Bermudes et al. |
| 2005/0255125 A1 | 11/2005 | Nuijten et al. |
| 2005/0267103 A1 | 12/2005 | Hochman |
| 2005/0271643 A1 | 12/2005 | Sorokulova et al. |
| 2005/0271683 A1 | 12/2005 | Claerebout et al. |
| 2005/0281841 A1 | 12/2005 | Kopecko et al. |
| 2005/0287123 A1 | 12/2005 | Xiang et al. |
| 2006/0018877 A1 | 1/2006 | Mikszta et al. |
| 2006/0019239 A1 | 1/2006 | Ivins et al. |
| 2006/0025387 A1 | 2/2006 | Hochman |
| 2006/0057152 A1 | 3/2006 | Marshall |
| 2006/0074039 A1 | 4/2006 | Klinman et al. |
| 2006/0078572 A1 | 4/2006 | Confer et al. |
| 2006/0083716 A1 | 4/2006 | Kaufman et al. |
| 2006/0089350 A1 | 4/2006 | Hochman et al. |
| 2006/0104955 A1 | 5/2006 | Redshaw |
| 2006/0115483 A1 | 6/2006 | Sleeman et al. |
| 2006/0115494 A1 | 6/2006 | Sun et al. |
| 2006/0121045 A1 | 6/2006 | Iverson et al. |
| 2006/0121054 A1 | 6/2006 | Sun et al. |
| 2006/0127408 A1 | 6/2006 | Young et al. |
| 2006/0140971 A1 | 6/2006 | Sung et al. |
| 2006/0140975 A1 | 6/2006 | Curtiss et al. |
| 2006/0147418 A1 | 7/2006 | Hone |
| 2006/0147461 A1 | 7/2006 | Galen |
| 2006/0153875 A1 | 7/2006 | Adler et al. |
| 2006/0171960 A1 | 8/2006 | Chu et al. |
| 2006/0182754 A1 | 8/2006 | Horwitz et al. |
| 2006/0189792 A1 | 8/2006 | Ruelle et al. |
| 2006/0193874 A1 | 8/2006 | Jones |
| 2006/0233835 A1 | 10/2006 | Paterson et al. |
| 2006/0240494 A1 | 10/2006 | Otvos et al. |
| 2006/0240515 A1* | 10/2006 | Dimitrov .............. A61K 39/215 435/69.1 |
| 2006/0246083 A1 | 11/2006 | Dale |
| 2006/0257415 A1 | 11/2006 | Sirard et al. |
| 2006/0269570 A1 | 11/2006 | Hone |
| 2006/0270043 A1 | 11/2006 | Blattner et al. |
| 2007/0004666 A1 | 1/2007 | Lasham et al. |
| 2007/0009489 A1 | 1/2007 | Bermudes et al. |
| 2007/0031382 A1 | 2/2007 | Powell et al. |
| 2007/0031458 A1 | 2/2007 | Favre et al. |
| 2007/0037225 A1 | 2/2007 | Metzger et al. |
| 2007/0048331 A1 | 3/2007 | Apicella et al. |
| 2007/0059323 A1 | 3/2007 | Reisfeld et al. |
| 2007/0104689 A1 | 5/2007 | Gillies et al. |
| 2007/0104733 A1 | 5/2007 | Gunn |
| 2007/0104736 A1 | 5/2007 | Apicella et al. |
| 2007/0110717 A1 | 5/2007 | Luo et al. |
| 2007/0110721 A1 | 5/2007 | Cranenburgh |
| 2007/0110752 A1 | 5/2007 | Murison et al. |
| 2007/0116725 A1 | 5/2007 | Vladoianu et al. |
| 2007/0122881 A1 | 5/2007 | Surber |
| 2007/0128216 A1 | 6/2007 | Horwitz et al. |
| 2007/0134214 A1 | 6/2007 | Xu |
| 2007/0134264 A1 | 6/2007 | Marshall |
| 2007/0134272 A1 | 6/2007 | Ayalew et al. |
| 2007/0141082 A1 | 6/2007 | Sung et al. |
| 2007/0154495 A1 | 7/2007 | Gorringe et al. |
| 2007/0169226 A1 | 7/2007 | Habben et al. |
| 2007/0189982 A1 | 8/2007 | Reynolds et al. |
| 2007/0191262 A1 | 8/2007 | Racila et al. |
| 2007/0202591 A1 | 8/2007 | Ulrich |
| 2007/0258901 A1 | 11/2007 | Boschert et al. |
| 2007/0281328 A1 | 12/2007 | Hsu et al. |
| 2007/0286874 A1 | 12/2007 | Cochran et al. |
| 2007/0287171 A1 | 12/2007 | Inouye |
| 2007/0298012 A1 | 12/2007 | King et al. |
| 2008/0008718 A1 | 1/2008 | Schuijffel et al. |
| 2008/0020441 A1 | 1/2008 | Brahmbhatt et al. |
| 2008/0038296 A1 | 2/2008 | Brahmbhatt et al. |
| 2008/0063655 A1 | 3/2008 | Adler et al. |
| 2008/0064062 A1 | 3/2008 | Leonhartsberger et al. |
| 2008/0076157 A1 | 3/2008 | Leonhartsberger et al. |
| 2008/0095794 A1 | 4/2008 | Sun et al. |
| 2008/0107653 A1 | 5/2008 | Vermeij |
| 2008/0112974 A1 | 5/2008 | Czerkinsky et al. |
| 2008/0124355 A1 | 5/2008 | Bermudes |
| 2008/0131466 A1 | 6/2008 | Reed et al. |
| 2008/0138359 A1 | 6/2008 | Steeghs et al. |
| 2008/0166757 A1 | 7/2008 | Bron et al. |
| 2008/0166764 A1 | 7/2008 | Schloesser et al. |
| 2008/0181892 A1 | 7/2008 | Ledbetter et al. |
| 2008/0182295 A1 | 7/2008 | Patkar et al. |
| 2008/0187520 A1 | 8/2008 | Polack et al. |
| 2008/0188436 A1 | 8/2008 | Brahmbhatt et al. |
| 2008/0193373 A1 | 8/2008 | Stritzker et al. |
| 2008/0193974 A1 | 8/2008 | Coleman et al. |
| 2008/0206284 A1 | 8/2008 | Williams et al. |
| 2008/0206814 A1 | 8/2008 | Lee et al. |
| 2008/0206818 A1 | 8/2008 | Wich et al. |
| 2008/0213308 A1 | 9/2008 | Valiante et al. |
| 2008/0241179 A1 | 10/2008 | Weston et al. |
| 2008/0241858 A1 | 10/2008 | Metzger et al. |
| 2008/0249013 A1 | 10/2008 | Cabezon et al. |
| 2008/0254058 A1 | 10/2008 | Glenting et al. |
| 2008/0254511 A1 | 10/2008 | Dassler et al. |
| 2008/0260769 A1 | 10/2008 | Capecchi et al. |
| 2008/0261869 A1 | 10/2008 | Shapiro |
| 2008/0280346 A1 | 11/2008 | de Lorenzo Prieto et al. |
| 2008/0286852 A1 | 11/2008 | Sun et al. |
| 2008/0311081 A1 | 12/2008 | Fruehauf et al. |
| 2008/0317742 A1 | 12/2008 | Chambers et al. |
| 2009/0011995 A1 | 1/2009 | Lee et al. |
| 2009/0017000 A1 | 1/2009 | Cai et al. |
| 2009/0017048 A1 | 1/2009 | Adler et al. |
| 2009/0028890 A1 | 1/2009 | Karp |
| 2009/0028892 A1 | 1/2009 | Claerebout et al. |
| 2009/0053186 A1 | 2/2009 | Hu et al. |
| 2009/0068226 A1 | 3/2009 | Ulrich et al. |
| 2009/0074816 A1 | 3/2009 | Gunn |
| 2009/0081250 A1 | 3/2009 | Paterson et al. |
| 2009/0081257 A1 | 3/2009 | Maier et al. |
| 2009/0104204 A1 | 4/2009 | Throsby et al. |
| 2009/0117047 A1 | 5/2009 | Szalay et al. |
| 2009/0117048 A1 | 5/2009 | Szalay et al. |
| 2009/0117049 A1 | 5/2009 | Szalay et al. |
| 2009/0117151 A1 | 5/2009 | Sung et al. |
| 2009/0117152 A1 | 5/2009 | Chu et al. |
| 2009/0123382 A1 | 5/2009 | Szalay et al. |
| 2009/0123426 A1 | 5/2009 | Li et al. |
| 2009/0136542 A1 | 5/2009 | Karp |
| 2009/0142310 A1 | 6/2009 | Klinman et al. |
| 2009/0148473 A1 | 6/2009 | Quinn et al. |
| 2009/0169517 A1 | 7/2009 | Bermudes et al. |
| 2009/0169562 A1 | 7/2009 | Throsby et al. |
| 2009/0175829 A1 | 7/2009 | Forbes et al. |
| 2009/0180955 A1 | 7/2009 | Stritzker et al. |
| 2009/0180987 A1 | 7/2009 | Stritzker et al. |
| 2009/0181078 A1 | 7/2009 | Reed et al. |
| 2009/0196887 A1 | 8/2009 | Morita et al. |
| 2009/0208534 A1 | 8/2009 | Xu et al. |
| 2009/0214476 A1 | 8/2009 | Pretzer et al. |
| 2009/0215754 A1 | 8/2009 | Hochman et al. |
| 2009/0220540 A1 | 9/2009 | Marshall |
| 2009/0227013 A1 | 9/2009 | Helentjaris et al. |
| 2009/0253778 A1 | 10/2009 | Reisfeld et al. |
| 2009/0263414 A1 | 10/2009 | Leenhouts et al. |
| 2009/0263418 A1 | 10/2009 | Speelman-Van Der Wel et al. |
| 2009/0285844 A1 | 11/2009 | Apicella et al. |
| 2009/0297552 A1 | 12/2009 | Aderem et al. |
| 2009/0297561 A1 | 12/2009 | Pasternack et al. |
| 2009/0300779 A1 | 12/2009 | Zhao et al. |
| 2009/0304750 A1 | 12/2009 | Hone et al. |
| 2009/0305398 A1 | 12/2009 | Hone |
| 2009/0317404 A1 | 12/2009 | Markham |
| 2009/0324503 A1 | 12/2009 | Lewinsohn et al. |
| 2009/0324576 A1 | 12/2009 | Padmanabhan et al. |

(56) References Cited

U.S. PATENT DOCUMENTS

| | | |
|---|---|---|
| 2009/0324638 A1 | 12/2009 | Dattwyler et al. |
| 2009/0324641 A1 | 12/2009 | Dominowski et al. |
| 2010/0047286 A1 | 2/2010 | Sun et al. |
| 2010/0055082 A1 | 3/2010 | Bauer et al. |
| 2010/0055127 A1 | 3/2010 | Venegas |
| 2010/0068214 A1 | 3/2010 | Rood et al. |
| 2010/0092438 A1 | 4/2010 | Fruehauf et al. |
| 2010/0092518 A1 | 4/2010 | Horwitz et al. |
| 2010/0099600 A1 | 4/2010 | Ny et al. |
| 2010/0120124 A1 | 5/2010 | Fernandez Herrero et al. |
| 2010/0129406 A1 | 5/2010 | Lauer et al. |
| 2010/0135961 A1 | 6/2010 | Bermudes |
| 2010/0135973 A1 | 6/2010 | Eisenstark et al. |
| 2010/0136048 A1 | 6/2010 | Bermudes |
| 2010/0136055 A1 | 6/2010 | Luo et al. |
| 2010/0136058 A1 | 6/2010 | Luo et al. |
| 2010/0137192 A1 | 6/2010 | Shapiro |
| 2010/0166786 A1 | 7/2010 | He et al. |
| 2010/0166800 A1 | 7/2010 | Cochran et al. |
| 2010/0172938 A1 | 7/2010 | Pouwels et al. |
| 2010/0172976 A1 | 7/2010 | Satishchandran et al. |
| 2010/0189691 A1 | 7/2010 | Fruehauf et al. |
| 2010/0196524 A1 | 8/2010 | Meindert De Vos et al. |
| 2010/0209446 A1 | 8/2010 | Claerebout et al. |
| 2010/0226891 A1 | 9/2010 | Sung et al. |
| 2010/0226931 A1 | 9/2010 | Valiante et al. |
| 2010/0226941 A1 | 9/2010 | Klinman et al. |
| 2010/0233195 A1 | 9/2010 | Delisa et al. |
| 2010/0233212 A1 | 9/2010 | Dubensky, Jr. et al. |
| 2010/0233213 A1 | 9/2010 | Sun et al. |
| 2010/0239546 A1 | 9/2010 | Fruehauf et al. |
| 2010/0272748 A1 | 10/2010 | Kopecko et al. |
| 2010/0272759 A1 | 10/2010 | Beck et al. |
| 2010/0285592 A1 | 11/2010 | Curtiss et al. |
| 2010/0291148 A1 | 11/2010 | Bernardini et al. |
| 2010/0297184 A1 | 11/2010 | Waller et al. |
| 2010/0297740 A1 | 11/2010 | Li et al. |
| 2010/0303862 A1 | 12/2010 | Ramachandran et al. |
| 2010/0310602 A1 | 12/2010 | Reed et al. |
| 2010/0322957 A1 | 12/2010 | Aderem et al. |
| 2011/0008389 A1 | 1/2011 | Cochran et al. |
| 2011/0014274 A1 | 1/2011 | Reed et al. |
| 2011/0020401 A1 | 1/2011 | Gunn |
| 2011/0021416 A1 | 1/2011 | Shapiro |
| 2011/0027349 A1 | 2/2011 | Sable et al. |
| 2011/0052628 A1 | 3/2011 | Hone |
| 2011/0059126 A1 | 3/2011 | Kohler et al. |
| 2011/0064723 A1 | 3/2011 | Truong-Le et al. |
| 2011/0064766 A1 | 3/2011 | Hawke et al. |
| 2011/0070290 A1 | 3/2011 | Reed et al. |
| 2011/0086059 A1 | 4/2011 | Galen et al. |
| 2011/0091493 A1 | 4/2011 | Moahamadzadeh et al. |
| 2011/0104186 A1 | 5/2011 | Valiante et al. |
| 2011/0104196 A1 | 5/2011 | Karp |
| 2011/0110979 A1 | 5/2011 | Nardelli Haefliger |
| 2011/0111481 A1 | 5/2011 | Li |
| 2011/0111496 A1 | 5/2011 | Li |
| 2011/0123565 A1 | 5/2011 | Weston et al. |
| 2011/0165680 A1 | 7/2011 | Blattner et al. |
| 2011/0183342 A1 | 7/2011 | Lewinsohn et al. |
| 2011/0195093 A1 | 8/2011 | Gunn |
| 2011/0200631 A1 | 8/2011 | Morsey et al. |
| 2011/0201092 A1 | 8/2011 | Dubensky, Jr. et al. |
| 2011/0201676 A1 | 8/2011 | Klinman et al. |
| 2011/0206694 A1 | 8/2011 | Fleckenstein |
| 2011/0209228 A1 | 8/2011 | Cocks et al. |
| 2011/0212090 A1 | 9/2011 | Pedersen et al. |
| 2011/0213129 A1 | 9/2011 | Reynolds et al. |
| 2011/0217323 A1 | 9/2011 | Valiante et al. |
| 2011/0223241 A1 | 9/2011 | Tardi et al. |
| 2011/0243992 A1 | 10/2011 | Kernodle |
| 2011/0256214 A1 | 10/2011 | Martin et al. |
| 2011/0268661 A1 | 11/2011 | Markiv et al. |
| 2011/0268739 A1 | 11/2011 | Throsby et al. |
| 2011/0274719 A1 | 11/2011 | Marshall |
| 2011/0275585 A1 | 11/2011 | Brahmbhatt et al. |
| 2011/0281330 A1 | 11/2011 | Sabbadini et al. |
| 2011/0287046 A1 | 11/2011 | Oloo et al. |
| 2011/0293662 A1 | 12/2011 | Blattner et al. |
| 2011/0312020 A1 | 12/2011 | Granoff et al. |
| 2011/0318308 A1 | 12/2011 | Ragolia |
| 2012/0003298 A1 | 1/2012 | Barberis et al. |
| 2012/0009247 A1 | 1/2012 | Maj et al. |
| 2012/0014881 A1 | 1/2012 | Lewinsohn et al. |
| 2012/0020883 A1 | 1/2012 | Stritzker et al. |
| 2012/0021517 A1 | 1/2012 | Jin et al. |
| 2012/0027811 A1 | 2/2012 | Edwards et al. |
| 2012/0036589 A1 | 2/2012 | Poobalane et al. |
| 2012/0039931 A1 | 2/2012 | Reisfeld et al. |
| 2012/0039994 A1 | 2/2012 | Reed et al. |
| 2012/0058142 A1 | 3/2012 | Kopecko et al. |
| 2012/0071545 A1 | 3/2012 | Shapiro |
| 2012/0077206 A1 | 3/2012 | Metzger et al. |
| 2012/0083587 A1 | 4/2012 | Gallo et al. |
| 2012/0093773 A1 | 4/2012 | Li et al. |
| 2012/0093850 A1 | 4/2012 | Bagnoli et al. |
| 2012/0093865 A2 | 4/2012 | Blattner et al. |
| 2012/0100177 A1 | 4/2012 | Ilg et al. |
| 2012/0107340 A1 | 5/2012 | Bagnoli et al. |
| 2012/0108640 A1 | 5/2012 | Hochman et al. |
| 2012/0115223 A1 | 5/2012 | Cai et al. |
| 2012/0121647 A1 | 5/2012 | Alonso et al. |
| 2012/0128594 A1 | 5/2012 | Choy et al. |
| 2012/0135039 A1 | 5/2012 | Aldwell et al. |
| 2012/0135503 A1 | 5/2012 | Sabbadini et al. |
| 2012/0141493 A1 | 6/2012 | Throsby et al. |
| 2012/0142079 A1 | 6/2012 | Sabbadini et al. |
| 2012/0142080 A1 | 6/2012 | Bermudes |
| 2012/0144509 A1 | 6/2012 | Benghezal et al. |
| 2012/0148601 A1 | 6/2012 | Ulrich et al. |
| 2012/0164687 A1 | 6/2012 | Bereta et al. |
| 2012/0177682 A1 | 7/2012 | Marshall |
| 2012/0189572 A1 | 7/2012 | Wei et al. |
| 2012/0189657 A1 | 7/2012 | Quinn et al. |
| 2012/0189661 A1 | 7/2012 | Nano |
| 2012/0208866 A1 | 8/2012 | Brahmbhatt et al. |
| 2012/0225454 A1 | 9/2012 | Benghezal et al. |
| 2012/0237491 A1 | 9/2012 | Padmanabhan et al. |
| 2012/0237537 A1 | 9/2012 | Lewinsohn et al. |
| 2012/0237544 A1 | 9/2012 | Cutting et al. |
| 2012/0244621 A1 | 9/2012 | Weiss et al. |
| 2012/0258128 A1 | 10/2012 | Dowling et al. |
| 2012/0258129 A1 | 10/2012 | He et al. |
| 2012/0258135 A1 | 10/2012 | Gunn et al. |
| 2012/0276167 A1 | 11/2012 | Lam et al. |
| 2012/0282181 A1 | 11/2012 | Lewinsohn et al. |
| 2012/0282291 A1 | 11/2012 | Berghman et al. |
| 2012/0288523 A1 | 11/2012 | Jacobs |
| 2012/0294948 A1 | 11/2012 | Poobalane et al. |
| 2012/0301422 A1 | 11/2012 | Meyer |
| 2012/0315278 A1 | 12/2012 | Throsby et al. |
| 2013/0004547 A1 | 1/2013 | Lam et al. |
| 2013/0018089 A1 | 1/2013 | Klinman et al. |
| 2013/0040370 A1 | 2/2013 | Genin |
| 2013/0058997 A1 | 3/2013 | Reed et al. |
| 2013/0064845 A1 | 3/2013 | Malouin et al. |
| 2013/0078275 A1 | 3/2013 | Tao |
| 2013/0078278 A1 | 3/2013 | Kopecko et al. |
| 2013/0084307 A1 | 4/2013 | Reed et al. |
| 2013/0095131 A1 | 4/2013 | Campos-Neto et al. |
| 2013/0096103 A1 | 4/2013 | Valiante et al. |
| 2013/0101523 A1 | 4/2013 | Lewinsohn et al. |
| 2013/0110249 A1 | 5/2013 | Schwarz et al. |
| 2013/0121968 A1 | 5/2013 | Quay |
| 2013/0130292 A1 | 5/2013 | Szalay et al. |
| 2013/0149321 A1 | 6/2013 | Ny et al. |
| 2013/0156809 A1 | 6/2013 | Sad et al. |
| 2013/0164307 A1 | 6/2013 | Markham |
| 2013/0164380 A1 | 6/2013 | Durum et al. |
| 2013/0177589 A1 | 7/2013 | Nano |
| 2013/0177593 A1 | 7/2013 | Gunn et al. |
| 2013/0209405 A1 | 8/2013 | Curtiss et al. |
| 2013/0217063 A1 | 8/2013 | Metzger et al. |
| 2013/0236948 A1 | 9/2013 | Barreira et al. |

(56) References Cited

U.S. PATENT DOCUMENTS

| | | |
|---|---|---|
| 2013/0251719 A1 | 9/2013 | Muller et al. |
| 2013/0266635 A1 | 10/2013 | Maj et al. |
| 2013/0267481 A1 | 10/2013 | Maj et al. |
| 2013/0273144 A1 | 10/2013 | Maj et al. |
| 2013/0287810 A1 | 10/2013 | Mohamadzadeh et al. |
| 2013/0295054 A1 | 11/2013 | Huang et al. |
| 2013/0302380 A1 | 11/2013 | Fujiwara et al. |
| 2013/0315950 A1 | 11/2013 | Dubensky et al. |
| 2013/0330824 A1 | 12/2013 | Li |
| 2013/0336990 A1 | 12/2013 | Meyer |
| 2013/0337012 A1 | 12/2013 | Gunn |
| 2013/0337545 A1 | 12/2013 | Sabbadini et al. |
| 2013/0345114 A1 | 12/2013 | Williams et al. |
| 2014/0004178 A1 | 1/2014 | Morici |
| 2014/0004193 A1 | 1/2014 | Gourapura et al. |
| 2014/0010844 A1 | 1/2014 | Gunn |
| 2014/0017279 A1 | 1/2014 | Brito et al. |
| 2014/0017285 A1 | 1/2014 | Brito et al. |
| 2014/0037691 A1 | 2/2014 | Reed et al. |
| 2014/0056940 A1 | 2/2014 | Dominowski et al. |
| 2014/0065187 A1 | 3/2014 | Carboulec et al. |
| 2014/0086950 A1 | 3/2014 | Pascual et al. |
| 2014/0093477 A1 | 4/2014 | Orth et al. |
| 2014/0093885 A1 | 4/2014 | Hua et al. |
| 2014/0093954 A1 | 4/2014 | Giacalone |
| 2014/0099320 A1 | 4/2014 | Throsby et al. |
| 2014/0112951 A1 | 4/2014 | Tang et al. |
| 2014/0134662 A1 | 5/2014 | Havell et al. |
| 2014/0148582 A1 | 5/2014 | Gallo et al. |
| 2014/0155343 A1 | 6/2014 | Brahmbhatt et al. |
| 2014/0178341 A1 | 6/2014 | Zhao et al. |
| 2014/0178425 A1 | 6/2014 | Bagnoli et al. |
| 2014/0186398 A1 | 7/2014 | Blander et al. |
| 2014/0186401 A1 | 7/2014 | Diamond et al. |
| 2014/0187612 A1 | 7/2014 | Agrez et al. |
| 2014/0193459 A1 | 7/2014 | Reed et al. |
| 2014/0205538 A1 | 7/2014 | Wei et al. |
| 2014/0206064 A1 | 7/2014 | Bayer et al. |
| 2014/0212396 A1 | 7/2014 | Newman |
| 2014/0220661 A1 | 8/2014 | Bermudes |
| 2014/0234310 A1 | 8/2014 | Shapiro |
| 2014/0234379 A1 | 8/2014 | Fujiwara et al. |
| 2014/0256922 A1 | 9/2014 | David et al. |
| 2014/0271563 A1 | 9/2014 | Alonso et al. |
| 2014/0271719 A1 | 9/2014 | Talaat |
| 2014/0294883 A1 | 10/2014 | Poobalane et al. |
| 2014/0322249 A1 | 10/2014 | Xiang et al. |
| 2014/0322265 A1 | 10/2014 | Chaplin et al. |
| 2014/0322267 A1 | 10/2014 | Haiwick et al. |
| 2014/0322268 A1 | 10/2014 | Reed et al. |
| 2014/0335125 A1 | 11/2014 | Le Gouellec et al. |
| 2014/0341921 A1 | 11/2014 | Honda et al. |
| 2014/0341942 A1 | 11/2014 | Oloo et al. |
| 2014/0341970 A1 | 11/2014 | Reed et al. |
| 2014/0341974 A1 | 11/2014 | Sorayya et al. |
| 2014/0356415 A1 | 12/2014 | DeShong et al. |
| 2014/0369986 A1 | 12/2014 | Padmanabhan et al. |
| 2014/0370036 A1 | 12/2014 | Shapiro |
| 2014/0370057 A1 | 12/2014 | Curtiss et al. |
| 2014/0371428 A1 | 12/2014 | Schwarz et al. |
| 2015/0017138 A1 | 1/2015 | Fruehauf et al. |
| 2015/0017191 A1 | 1/2015 | Fox et al. |
| 2015/0017204 A1 | 1/2015 | Bermudes |
| 2015/0030573 A1 | 1/2015 | Fruehauf et al. |
| 2015/0037370 A1 | 2/2015 | Corbeil et al. |
| 2015/0050311 A1 | 2/2015 | Schubert et al. |
| 2015/0056246 A1 | 2/2015 | Putnam et al. |
| 2015/0071994 A1 | 3/2015 | Schentag et al. |
| 2015/0093824 A1 | 4/2015 | Satishchandran et al. |
| 2015/0125485 A1 | 5/2015 | Dubensky, Jr. et al. |
| 2015/0125921 A1 | 5/2015 | Kotelko et al. |
| 2015/0132335 A1 | 5/2015 | Malouin et al. |
| 2015/0140028 A1 | 5/2015 | Sad et al. |
| 2015/0140034 A1 | 5/2015 | Dominowski et al. |
| 2015/0140037 A1 | 5/2015 | Galan et al. |
| 2015/0165011 A1 | 6/2015 | Lubenau |
| 2015/0174178 A1 | 6/2015 | Kovarik et al. |
| 2015/0182611 A1 | 7/2015 | Kopecko et al. |
| 2015/0184167 A1 | 7/2015 | Fruehauf et al. |
| 2015/0190500 A1 | 7/2015 | Berghman et al. |
| 2015/0196659 A1 | 7/2015 | Leenhouts et al. |
| 2015/0202276 A1 | 7/2015 | Lewinsohn et al. |
| 2015/0204845 A1 | 7/2015 | De Armas et al. |
| 2015/0218254 A1 | 8/2015 | Sabbadini et al. |
| 2015/0219645 A1 | 8/2015 | Lewinsohn et al. |
| 2015/0225692 A1 | 8/2015 | Bhatia et al. |
| 2015/0238589 A1 | 8/2015 | Gunn et al. |
| 2015/0258190 A1 | 9/2015 | Grandi |
| 2015/0265696 A1 | 9/2015 | Gourapura et al. |
| 2015/0273045 A1 | 10/2015 | Kolander et al. |
| 2015/0316567 A1 | 11/2015 | Salha et al. |
| 2015/0321037 A1 | 11/2015 | Li et al. |
| 2015/0335736 A1 | 11/2015 | Reed et al. |
| 2015/0343050 A1 | 12/2015 | Gunn |
| 2015/0359909 A1 | 12/2015 | O'Sullivan et al. |
| 2015/0376242 A1 | 12/2015 | Oloo et al. |
| 2016/0000896 A1 | 1/2016 | Carboulec et al. |
| 2016/0022592 A1 | 1/2016 | Kabadi et al. |
| 2016/0028148 A1 | 1/2016 | Tan et al. |
| 2016/0030494 A1 | 2/2016 | Henn et al. |
| 2016/0045591 A1 | 2/2016 | Campos-Neto et al. |
| 2016/0054299 A9 | 2/2016 | De Armas et al. |
| 2016/0058860 A1 | 3/2016 | Reed et al. |
| 2016/0074505 A1 | 3/2016 | Kovarik et al. |
| 2016/0090395 A1 | 3/2016 | Maj et al. |
| 2016/0101168 A1 | 4/2016 | Husseiny Elsayed et al. |
| 2016/0103127 A1 | 4/2016 | Lewinsohn et al. |
| 2016/0108096 A1 | 4/2016 | Thompson et al. |
| 2016/0136285 A1 | 5/2016 | Gozdziewicz et al. |
| 2016/0136294 A1 | 5/2016 | Leenhouts et al. |
| 2016/0158334 A1 | 6/2016 | Giacalone |
| 2016/0158335 A1 | 6/2016 | Bagnoli et al. |
| 2016/0169921 A1 | 6/2016 | Orth et al. |
| 2016/0175415 A1 | 6/2016 | Dubensky, Jr. et al. |
| 2016/0175428 A1 | 6/2016 | Tang et al. |
| 2016/0193256 A1 | 7/2016 | Honda et al. |
| 2016/0193257 A1 | 7/2016 | Honda et al. |
| 2016/0199422 A1 | 7/2016 | Newman |
| 2016/0199474 A1 | 7/2016 | Ramachandran et al. |
| 2016/0206727 A1 | 7/2016 | Haiwick et al. |
| 2016/0208261 A1 | 7/2016 | Satishchandran et al. |
| 2016/0213770 A1 | 7/2016 | Ilg et al. |
| 2016/0220652 A1 | 8/2016 | Petit et al. |
| 2016/0222393 A1 | 8/2016 | Bermudes |
| 2016/0228523 A1 | 8/2016 | Newman |
| 2016/0228530 A1 | 8/2016 | Paterson |
| 2016/0243204 A1 | 8/2016 | Ny et al. |
| 2016/0250311 A1 | 9/2016 | Lubenau |
| 2016/0263209 A1 | 9/2016 | Gunn |
| 2016/0289287 A1 | 10/2016 | Hancock et al. |
| 2016/0317637 A1 | 11/2016 | Agrawal et al. |
| 2016/0324783 A1 | 11/2016 | Fox et al. |
| 2016/0324939 A1 | 11/2016 | Allan |
| 2016/0346381 A1 | 12/2016 | Qiao et al. |
| 2016/0354462 A1 | 12/2016 | Campos-Neto et al. |
| 2016/0366862 A1 | 12/2016 | Havell et al. |
| 2016/0367650 A1 | 12/2016 | Paterson |
| 2016/0369282 A1 | 12/2016 | Li et al. |
| 2017/0007683 A1 | 1/2017 | Mueller et al. |
| 2017/0014513 A1 | 1/2017 | O'Connell et al. |
| 2017/0015735 A1 | 1/2017 | Schwarz et al. |
| 2017/0021011 A1 | 1/2017 | Kovarik et al. |
| 2017/0028048 A1 | 2/2017 | Lewinsohn et al. |
| 2017/0042987 A1 | 2/2017 | D'Souza |
| 2017/0042996 A1 | 2/2017 | Wallecha et al. |
| 2017/0051260 A1 | 2/2017 | Bermudes et al. |
| 2017/0072042 A1 | 3/2017 | Fergen et al. |
| 2017/0080078 A1 | 3/2017 | Gourapura et al. |
| 2017/0081642 A1 | 3/2017 | Chaplin et al. |
| 2017/0081671 A1 | 3/2017 | Diamond et al. |
| 2017/0095548 A1 | 4/2017 | Malouin et al. |
| 2017/0106028 A1 | 4/2017 | Fujiwara et al. |
| 2017/0106074 A1 | 4/2017 | Alonso et al. |
| 2017/0114319 A1 | 4/2017 | Le Gouellec et al. |

(56) References Cited

U.S. PATENT DOCUMENTS

| | | |
|---|---|---|
| 2017/0129942 A1 | 5/2017 | Plante et al. |
| 2017/0136102 A1 | 5/2017 | Sharma |
| 2017/0136111 A1 | 5/2017 | Nano |
| 2017/0143815 A1 | 5/2017 | Giacalone |
| 2017/0145061 A1 | 5/2017 | Lu et al. |
| 2017/0145065 A1 | 5/2017 | Haagsman et al. |
| 2017/0151321 A1 | 6/2017 | Luo et al. |
| 2017/0157232 A1 | 6/2017 | Bremer et al. |
| 2017/0157239 A1 | 6/2017 | Bermudes |
| 2017/0174746 A1 | 6/2017 | Sad et al. |
| 2017/0182155 A1 | 6/2017 | Reed et al. |
| 2017/0191058 A1 | 7/2017 | De Armas et al. |
| 2017/0209502 A1 | 7/2017 | Honda et al. |
| 2017/0216378 A1 | 8/2017 | Honda et al. |
| 2017/0240615 A1 | 8/2017 | Shapiro |
| 2017/0246281 A1 | 8/2017 | Super et al. |
| 2017/0258885 A1 | 9/2017 | Luirink et al. |
| 2017/0290889 A1 | 10/2017 | Loke et al. |
| 2017/0290901 A1 | 10/2017 | Talaat |
| 2017/0304434 A1 | 10/2017 | Dominowski et al. |
| 2017/0318817 A1 | 11/2017 | Padmanabhan et al. |
| 2017/0327830 A1 | 11/2017 | Curtiss et al. |
| 2017/0340720 A1 | 11/2017 | Bagnoli et al. |
| 2017/0350890 A1 | 12/2017 | Cirillo et al. |
| 2017/0360540 A1 | 12/2017 | Jackwood et al. |
| 2017/0368156 A1 | 12/2017 | Husseiny Elsayed et al. |
| 2017/0368166 A1 | 12/2017 | Gunn |
| 2018/0008701 A1 | 1/2018 | Dominowski et al. |
| 2018/0021424 A1 | 1/2018 | Dominowski et al. |
| 2018/0028642 A1 | 2/2018 | Cherpes et al. |
| 2018/0028649 A1 | 2/2018 | Reed et al. |
| 2018/0043021 A1 | 2/2018 | Schwarz et al. |
| 2018/0044406 A1 | 2/2018 | Schwarz et al. |
| 2018/0049413 A1 | 2/2018 | Havell et al. |
| 2018/0050099 A1 | 2/2018 | Gunn et al. |
| 2018/0066041 A1 | 3/2018 | Szij Rto et al. |
| 2018/0066225 A1 | 3/2018 | Choi et al. |
| 2018/0071377 A1 | 3/2018 | Putnam et al. |
| 2018/0087060 A1 | 3/2018 | Fruehauf et al. |
| 2018/0099999 A1 | 4/2018 | Thompson et al. |
| 2018/0104328 A1 | 4/2018 | Qiao et al. |
| 2018/0140665 A1 | 5/2018 | Giacalone |
| 2018/0147278 A1 | 5/2018 | Klocke et al. |
| 2018/0164221 A1 | 6/2018 | Singh et al. |
| 2018/0168488 A1 | 6/2018 | Jones et al. |
| 2018/0168489 A1 | 6/2018 | Jones et al. |
| 2018/0168490 A1 | 6/2018 | Jones et al. |
| 2018/0169222 A1 | 6/2018 | Lopez |
| 2018/0169226 A1 | 6/2018 | Reed et al. |
| 2018/0185469 A1 | 7/2018 | Gourapura et al. |
| 2018/0193003 A1 | 7/2018 | Jones et al. |
| 2018/0193441 A1 | 7/2018 | Rubio Nistal et al. |
| 2018/0206726 A1 | 7/2018 | Singh et al. |
| 2018/0206769 A1 | 7/2018 | Pak et al. |
| 2018/0221286 A1 | 8/2018 | Kabadi et al. |
| 2018/0221470 A1 | 8/2018 | Reed et al. |
| 2018/0236063 A1 | 8/2018 | Reed et al. |
| 2018/0243347 A1 | 8/2018 | Agrawal et al. |
| 2018/0243348 A1 | 8/2018 | Honda et al. |
| 2018/0271787 A1 | 9/2018 | Tardi et al. |
| 2019/0017057 A1 | 1/2019 | Bermudes |
| 2019/0055569 A1 | 2/2019 | Lesser et al. |

FOREIGN PATENT DOCUMENTS

| | | |
|---|---|---|
| EP | 1402036 | 3/2004 |
| EP | 1407052 | 4/2004 |
| EP | 1068339 B1 | 7/2008 |
| WO | WO0047222 | 8/2000 |
| WO | WO0125397 | 4/2001 |
| WO | WO02067983 | 9/2002 |
| WO | WO02074336 | 9/2002 |
| WO | WO2002070645 | 9/2002 |
| WO | WO02083214 | 10/2002 |
| WO | WO02087494 | 11/2002 |
| WO | WO03014380 | 2/2003 |
| WO | WO2004016281 A1 | 2/2004 |
| WO | WO2005005630 | 1/2005 |
| WO | WO2005018332 | 3/2005 |
| WO | WO2005054477 | 6/2005 |
| WO | WO2006017929 | 2/2006 |
| WO | WO2006048344 | 5/2006 |
| WO | WO2008073148 | 6/2008 |
| WO | WO2008089132 | 7/2008 |
| WO | WO2009021548 | 2/2009 |
| WO | WO2009126189 | 10/2009 |

* cited by examiner

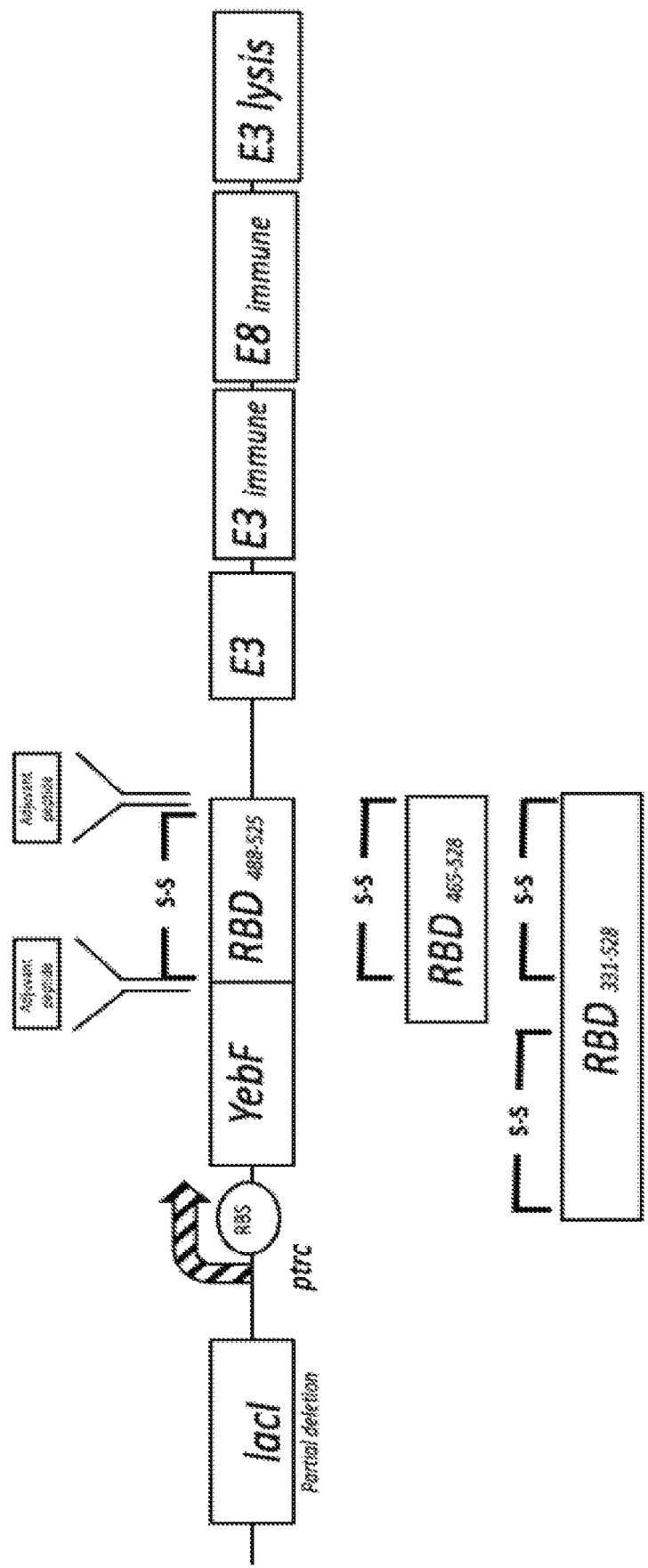

SEQUENCE LISTING

```
<160> NUMBER OF SEQ ID NOS: 15

<210> SEQ ID NO 1
<211> LENGTH: 198
<212> TYPE: PRT
<213> ORGANISM: Artificial Sequence
<220> FEATURE:
<223> OTHER INFORMATION: receptor binding domain of SARS-CoV-2, with 4
      added amino acids (CGPK)

<400> SEQUENCE: 1

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
    50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
    130                 135                 140

Ala Gly Ser Thr Pro Cys Asn Gly Val Glu Gly Phe Asn Cys Tyr Phe
```

```
                145                 150                 155                 160
Pro Leu Gln Ser Tyr Gly Phe Gln Pro Thr Asn Gly Val Gly Tyr Gln
                    165                 170                 175

Pro Tyr Arg Val Val Val Leu Ser Phe Glu Leu Leu His Ala Pro Ala
                180                 185                 190

Thr Val Cys Gly Pro Lys
            195

<210> SEQ ID NO 2
<211> LENGTH: 43
<212> TYPE: PRT
<213> ORGANISM: Artificial Sequence
<220> FEATURE:
<223> OTHER INFORMATION: Flexible linker with SARS-CoV-2-RBD 488-525

<400> SEQUENCE: 2

Gly Gly Gly Gly Ser Cys Tyr Phe Pro Leu Gln Ser Tyr Gly Phe Gln
1               5                   10                  15

Pro Thr Asn Gly Val Gly Tyr Gln Pro Tyr Arg Val Val Val Leu Ser
            20                  25                  30

Phe Glu Leu Leu His Ala Pro Ala Thr Val Cys
        35                  40

<210> SEQ ID NO 3
<211> LENGTH: 46
<212> TYPE: PRT
<213> ORGANISM: Artificial Sequence
<220> FEATURE:
<223> OTHER INFORMATION: flexible linker with RBD 488-528

<400> SEQUENCE: 3

Gly Gly Gly Gly Ser Cys Tyr Phe Pro Leu Gln Ser Tyr Gly Phe Gln
1               5                   10                  15

Pro Thr Asn Gly Val Gly Tyr Gln Pro Tyr Arg Val Val Val Leu Ser
            20                  25                  30

Phe Glu Leu Leu His Ala Pro Ala Thr Val Cys Gly Pro Lys
        35                  40                  45

<210> SEQ ID NO 4
<211> LENGTH: 28
<212> TYPE: PRT
<213> ORGANISM: Artificial Sequence
<220> FEATURE:
<223> OTHER INFORMATION: synthetic peptide corresponding to the CR2-
      binding site on C3d, P28

<400> SEQUENCE: 4

Lys Phe Leu Thr Thr Ala Lys Asp Lys Asn Arg Trp Glu Asp Pro Gly
1               5                   10                  15

Lys Gln Leu Tyr Asn Val Glu Ala Thr Ser Tyr Ala
            20                  25

<210> SEQ ID NO 5
<211> LENGTH: 519
<212> TYPE: DNA
<213> ORGANISM: Artificial Sequence
<220> FEATURE:
<223> OTHER INFORMATION: An expression plasmid, pTrc99a, with a YebF,
      containing an in-frame fusion with a portion of the RBD consisting
      of 41 amino acids, from a cysteine to a cysteine with added GPK
      and an added artificial lysine followed by a stop codon

<400> SEQUENCE: 5
```

-continued

| | |
|---|---|
| atggctaaaa aaagagggc gttttagg ctgttgttgg tttctgcctg cgcatcagtt | 60 |
| ttcgctgcca ataatgaaac cagcaagtcg gtcactttcc caaagtgtga agatctggat | 120 |
| gctgccggaa ttgccgcgag cgtaaaacgt gattatcaac aaaatcgcgt ggcgcgttgg | 180 |
| gcagatgatc aaaaaattgt cggtcaggcc gatcccgtgg cttgggtcag tttgcaggac | 240 |
| attcaggta aagatgataa atggtcagta ccgctaaccg tgcgtggtaa aagtgccgat | 300 |
| attcattacc aggtcagcgt ggactgcaaa gcgggaatgg cggaatatca gcggcgtctc | 360 |
| gagggtacta gtggcggtgg tggcagttgc tattttccac tgcagtctta tggctttcag | 420 |
| ccgactaacg gtgtgggtta ccaaccgtac cgtgtggttg tactgtcttt cgagctgctg | 480 |
| catgccccgg caaccgtatg cggcccgaag aaatcttga | 519 |

<210> SEQ ID NO 6
<211> LENGTH: 6690
<212> TYPE: DNA
<213> ORGANISM: Artificial Sequence
<220> FEATURE:
<223> OTHER INFORMATION: complete pTrc99a plasmid, with the YebF 41aa of RBD, and the ColE3 colicin, immunity and lysis protein

<400> SEQUENCE: 6

| | |
|---|---|
| gtttgacagc ttatcatcga ctgcacggtg caccaatgct tctggcgtca ggcagccatc | 60 |
| ggaagctgtg gtatggctgt gcaggtcgta atcactgca taattcgtgt cgctcaaggc | 120 |
| gcactcccgt tctggataat gttttttgcg ccgacatcat aacggttctg gcaaatattc | 180 |
| tgaaatgagc tgttgacaat taatcatccg gctcgtataa tgtgtggaat tgtgagcgga | 240 |
| taacaatttc acacaggaaa cagaccatgg ctaaaaaag aggggcgttt ttagggctgt | 300 |
| tgttggtttc tgcctgcgca tcagttttcg ctgccaataa tgaaaccagc aagtcggtca | 360 |
| cttttcccaaa gtgtgaagat ctggatgctg ccggaattgc cgcgagcgta aaacgtgatt | 420 |
| atcaacaaaa tcgcgtggcg cgttgggcag atgatcaaaa aattgtcggt caggccgatc | 480 |
| ccgtggcttg ggtcagtttg caggacattc agggtaaaga tgataatggg tcagtaccgc | 540 |
| taaccgtgcg tggtaaaagt gccgatattc attaccaggt cagcgtggac tgcaaagcgg | 600 |
| gaatggcgga atatcagcgg cgtctcgagg gtactagtgg cggtggtggc agttgctatt | 660 |
| ttccactgca gtcttatggc tttcagccga ctaacggtgt gggttaccaa ccgtaccgtg | 720 |
| tggttgtact gtctttcgag ctgctgcatg ccccggcaac cgtatgcggc ccgaagaaat | 780 |
| cttgatctag agtcgacctg caggcatgca agcttggctg ttttggcgga tgagagaaga | 840 |
| ttttcagcct gatacagatt aaatcagaac gcagaagcgg tctgataaaa cagaatttgc | 900 |
| ctggcggcag tagcgcggtg gtcccacctg accccatgcc gaactcagaa gtgaaacgcc | 960 |
| gtagcgccga tggtagtgtg gggtctcccc atgcgagagt agggaactgc caggcatcaa | 1020 |
| ataaaacgaa aggctcagtc gaaagactgg gcctttcgtt ttatctgttg tttgtcggtg | 1080 |
| aacgctctcc tgagtaggac aaatccgccg ggagcggatt tgaacgttgc gaagcaacgg | 1140 |
| cccggagggt ggcgggcagg acgcccgcca taaactgcca ggcatcaaat taagcagaag | 1200 |
| gccatcctga cggatggcct ttttgcgttt ctacaaactc ttttgttta ttttctaaa | 1260 |
| tacattcaaa tatgtatccg ctcatgagac aataaccctg ataaatgctt caataatatt | 1320 |
| gaaaaggaa gagtatgagt attcaacatt tccgtgtcgc ccttattccc ttttttgcgg | 1380 |
| cattttgcct tcctgttttt gctcacccag aaacgctggt gaaagtaaaa gatgctgaag | 1440 |
| atcagttggg tgcacgagtg ggttacatcg aactggatct caacagcggt aagatccttg | 1500 |

```
agagttttcg ccccgaagaa cgttttccaa tgatgagcac ttttaaagtt ctgctatgtg    1560
gcgcggtatt atcccgtgtt gacgccgggc aagagcaact cggtcgccgc atacactatt    1620
ctcagaatga cttggttgag tactcaccag tcacagaaaa gcatcttacg gatggcatga    1680
cagtaagaga attatgcagt gctgccataa ccatgagtga taacactgcg gccaacttac    1740
ttctgacaac gatcggagga ccgaaggagc taaccgcttt tttgcacaac atgggggatc    1800
atgtaactcg ccttgatcgt tgggaaccgg agctgaatga agccatacca aacgacgagc    1860
gtgacaccac gatgcctaca gcaatggcaa caacgttgcg caaactatta actggcgaac    1920
tacttactct agcttcccgg caacaattaa tagactggat ggaggcggat aaagttgcag    1980
gaccacttct gcgctcggcc cttccggctg gctggtttat tgctgataaa tctggagccg    2040
gtgagcgtgg gtctcgcggt atcattgcag cactggggcc agatggtaag ccctcccgta    2100
tcgtagttat ctacacgacg gggagtcagg caactatgga tgaacgaaat agacagatcg    2160
ctgagatagg tgcctcactg attaagcatt ggtaactgtc agaccaagtt tactcatata    2220
tactttagat tgatttaaaa cttcattttt aatttaaaag gatctaggtg aagatccttt    2280
ttgataatct catgaccaaa atcccttaac gtgagttttc gttccactga gcgtcagacc    2340
ccgtagaaaa gatcaaagga tcttcttgag atcctttttt tctgcgcgta atctgctgct    2400
tgcaaacaaa aaaaccaccg ctaccagcgg tggtttgttt gccggatcaa gagctaccaa    2460
ctcttttttcc gaaggtaact ggcttcagca gagcgcagat accaaatact gtccttctag    2520
tgtagccgta gttaggccac cacttcaaga actctgtagc accgcctaca tacctcgctc    2580
tgctaatcct gttaccagtg gctgctgcca gtggcgataa gtcgtgtctt accgggttgg    2640
actcaagacg atagttaccg gataaggcgc agcggtcggg ctgaacgggg ggttcgtgca    2700
cacagcccag cttggagcga acgacctaca ccgaactgag atacctacag cgtgagctat    2760
gagaaagcgc cacgcttccc gaagggagaa aggcggacag gtatccggta agcggcaggg    2820
tcggaacagg agagcgcacg agggagcttc caggggggaaa cgcctggtat ctttatagtc    2880
ctgtcgggtt tcgccacctc tgacttgagc gtcgattttt gtgatgctcg tcagggggggc    2940
ggagcctatg gaaaaacgcc agcaacgcgg ccttttttacg gttcctggcc ttttgctggc    3000
cttttgctca catgttcttt cctgcgttat cccctgattc tgtggataac cgtattaccg    3060
cctttgagtg agctgatacc gctcgccgca gccgaacgac cgagcgcagc gagtcagtga    3120
gcgaggaagc ggaagagcgc ctgatgcggt attttctcct tacgcatctg tgcggtattt    3180
cacaccgcat atgcccgctc tgcgttttct aagtgttatc cctcctgatt tctaaaaaat    3240
tttccacctg aacttgacag aaaaaacgat gacgagtact ttttgatctg tacataaacc    3300
cagtggtttt atgtacagta ttaatcgtgt aatcaattgt tttaacgctt aaaagaggga    3360
attttttatga gcggtggcga tggacgcggc cataacacgg gcgcgcatag cacaagtggt    3420
aacattaatg gtggcccgac cgggcttggt gtaggtggtg gtgcttctga tggctccgga    3480
tggagttcgg aaaataaccc gtggggtggt ggttccggta gcggcattca ctggggtggt    3540
ggttccggtc atggtaatgg cggggggaat ggtaattccg gtggtggttc gggaacaggc    3600
ggtaatctgt cagcagtagc tgcgccagtg gcatttggtt ttccggcact tccactcca    3660
ggagctggcg gtctggcggt cagtatttca gcgggagcat tatcggcagc tattgctgat    3720
attatggctg ccctgaaagg accgtttaaa tttggtcttt gggggggtggc tttatatggt    3780
gtattgccat cacaaatagc gaaagatgac cccaatatga tgtcaaagat tgtgacgtca    3840
ttacccgcag atgatattac tgaatcacct gtcagttcat tacctctcga taaggcaaca    3900
```

```
gtaaacgtaa atgttcgtgt tgttgatgat gtaaaagacg agcgacagaa tatttcggtt   3960
gtttcaggtg ttccgatgag tgttccggtg gttgatgcaa aacctaccga acgtccgggt   4020
gtttttacgg catcaattcc aggtgcacct gttctgaata tttcagttaa taacagtacg   4080
ccagcagtac agacattaag cccaggtgtt acaaataata ctgataagga tgttcgcccg   4140
gcaggattta ctcagggtgg taataccagg gatgcagtta ttcgattccc gaaggacagc   4200
ggtcataatg ccgtatatgt ttcagtgagt gatgttctta gccctgacca ggtaaaacaa   4260
cgtcaagatg aagaaaatcg ccgtcagcag gaatgggatg ctacgcatcc ggttgaagcg   4320
gctgagcgaa attatgaacg cgcgcgtgca gagctgaatc aggcaaatga agatgttgcc   4380
agaaatcagg agcgacaggc taaagctgtt caggtttata attcgcgtaa aagcgaactt   4440
gatgcagcga ataaaactct tgctgatgca atagctgaaa taaaacaatt taatcgattt   4500
gcccatgacc caatggctgg cggtcacaga atgtggcaaa tggccgggct aaagcccag    4560 cgggcgcaga cggatgtaaa taataagcag gctgcatttg atgctgctgc aaaagagaag   4620
tcagatgctg atgctgcatt gagttctgct atggaaagca ggaagaagaa agaagataag   4680
aaaaggagtg ctgaaaataa tttaaacgat gaaaagaata agcccagaaa aggttttaaa   4740
gattacgggc atgattatca tccagctccg aaaactgaga atattaaagg gcttggtgat   4800
cttaagcctg ggataccaaa aacaccaaag cagaatggtg gtggaaaacg caagcgctgg   4860
actggagata aagggcgtaa gatttatgag tgggattctc agcatggtga gcttgagggg   4920
tatcgtgcca gtgatggtca gcatcttggc tcatttgacc ctaaaacagg caatcagttg   4980
aaaggtccag atccgaaacg aaatatcaag aaatatcttt gagaggaagt tatgggactt   5040
aaattggatt taacttggtt tgataaaagt acagaagatt ttaagggtga ggagtattca   5100
aaagattttg gagatgacgg ttcagttatg gaaagtctag gtgtgccttt taaggataat   5160
gttaataacg gttgctttga tgttatagct gaatgggtac ctttgctaca accatacttt   5220
aatcatcaaa ttgatatttc cgataatgag tattttgttt cgtttgatta tcgtgatggt   5280
gattggtgat caaatattat cagggatgag ttgatatacg ggcttctagt gttcatggat   5340
gaacgctgga gcctccaaat gtagaaatgt tatatttttt attgagttct tggttataat   5400
tgctccgcaa tgatttaaat aagcattatt taaaacattc tcaggagagg tgaaggtgga   5460
gctaaaaaaa agtattggtg attacactga aaccgaattc aaaaaattta ttgaagacat   5520
catcaattgt gaaggtgatg aaaaaaaaca ggatgataac ctcgagtatt ttataaatgt   5580
tactgagcat cctagtggtt ctgatctgat ttattaccca gaaggtaata atgatggtag   5640
ccctgaaggt gttattaaag agattaaaga atggcgagcc gctaacggta agtcaggatt   5700
taaacagggc tgaaatatga atgccggttg tttatggatg aatggctggc attctttcac   5760
aacaaggagt cgttatgaaa aaaataacag ggattatttt attgcttctt gcagtcatta   5820
ttctgtctgc atgtcaggca aactatatcc gggatgttca gggcgggacc gtatctccgt   5880
catcaacagc tgaagtgacc ggattagcaa cgcagtaacc cgaaatcctc tttgacaaaa   5940
acaaagcgtg tcaggctgcg gccgcccatt gctgtggaag ctgcctgcac taatgttccg   6000
gcgttatttc ttgatgtctc tgaccagaca cccatcaaca gtattatttt ctcccatgaa   6060
gacggtacgc gactgggcgt ggagcatctg gtcgcattgg gtcaccagca aatcgcgctg   6120
ttagcgggcc cattaagttc tgtctcggcg cgtctgcgtc tggctggctg gcataaatat   6180
ctcactcgca atcaaattca gccgatagcg gaacgggaag gcgactggag tgccatgtcc   6240
```

```
ggttttcaac aaaccatgca aatgctgaat gagggcatcg ttcccactgc gatgctggtt    6300
gccaacgatc agatggcgct gggcgcaatg cgcgccatta ccgagtccgg gctgcgcgtt    6360
ggtgcggata tctcggtagt gggatacgac gataccgaag acagctcatg ttatatcccg    6420
ccgttaacca ccatcaaaca ggattttcgc ctgctgggc aaaccagcgt ggaccgcttg     6480
ctgcaactct ctcagggcca ggcggtgaag ggcaatcagc tgttgcccgt ctcactggtg    6540
aaaagaaaaa ccaccctggc gcccaatacg caaaccgcct ctccccgcgc gttggccgat    6600
tcattaatgc agctggcacg acaggtttcc cgactggaaa gcgggcagtg agcgcaacgc    6660
aattaatgtg agttagcgcg aattgatctg                                     6690
```

<210> SEQ ID NO 7
<211> LENGTH: 13
<212> TYPE: PRT
<213> ORGANISM: Artificial Sequence
<220> FEATURE:
<223> OTHER INFORMATION: truncated p28 peptide

<400> SEQUENCE: 7

Gly Lys Gln Leu Tyr Asn Val Glu Ala Thr Ser Tyr Ala
1               5                   10

<210> SEQ ID NO 8
<211> LENGTH: 136
<212> TYPE: PRT
<213> ORGANISM: Artificial Sequence
<220> FEATURE:
<223> OTHER INFORMATION: peptide adjuvant containing P28 dimer,
      separated by a portion of the Vibrio vulnificus flagellin with
      flexible linkers

<400> SEQUENCE: 8

Lys Phe Leu Thr Thr Ala Lys Asp Lys Asn Arg

```
ctgaacttga cagaaaaaac gatgacgagt acttttttgat ctgtacataa acccagtggt    120
tttatgtaca gtattaatcg tgtaatcaat tgttttaacg cttaaaagag ggaatttta     180 tgagcggtgg cgatggacgc ggccataaca cgggcgcgca tagcacaagt ggtaacatta    240
atggtggccc gaccgggctt ggtgtaggtg gtggtgcttc tgatggctcc ggatggagtt    300
cggaaaataa cccgtgtgggt ggtggttccg gtagcggcat tcactggggt ggtggttccg   360
gtcatggtaa tggcgggggg aatggtaatt ccggtggtgg ttcgggaaca ggcggtaatc    420
tgtcagcagt agctgcgcca gtggcatttg gttttccggc actttccact ccaggagctg    480
gcggtctggc ggtcagtatt tcagcgggag cattatcggc agctattgct gatattatgg    540
ctgccctgaa aggaccgttt aaatttggtc tttgggggt ggctttatat ggtgtattgc     600
catcacaaat agcgaaagat gaccccaata tgatgtcaaa gattgtgacg tcattacccg    660
cagatgatat tactgaatca cctgtcagtt cattacctct cgataaggca acagtaaacg    720
taaatgttcg tgttgttgat gatgtaaaag acgagcgaca gaatatttcg gttgtttcag    780
gtgttccgat gagtgttccg gtggttgatg caaaacctac cgaacgtccg ggtgttttta    840
cggcatcaat tccaggtgca cctgttctga atatttcagt taataacagt acgccagcag    900
tacagacatt aagcccaggt gttacaaata atactgataa ggatgttcgc ccggcaggat    960
ttactcaggg tggtaatacc agggatgcag ttattcgatt cccgaaggac agcggtcata    1020
atgccgtata tgtttcagtg agtgatgttc ttagccctga ccaggtaaaa caacgtcaag    1080
atgaagaaaa tcgccgtcag caggaatggg atgctacgca tccggttgaa gcggctgagc    1140
gaaattatga acgcgcgcgt gcagagctga atcaggcaaa tgaagatgtt gccagaaatc    1200
aggagcgaca ggctaaagct gttcaggttt ataattcgcg taaaagcgaa cttgatgcag    1260
cgaataaaac tcttgctgat gcaatagctg aaataaaaca atttaatcga tttgcccatg    1320
acccaatggc tggcggtcac agaatgtggc aaatggccgg gcttaaagcc cagcgggcgc    1380
agacggatgt aaataataag caggctgcat ttgatgctgc tgcaaaagag aagtcagatg    1440
ctgatgctgc attgagttct gctatggaaa gcaggaagaa gaaagaagat aagaaaagga    1500
gtgctgaaaa taatttaaac gatgaaaaga ataagcccag aaaaggtttt aaagattacg    1560
ggcatgatta tcatccagct ccgaaaactg agaatattaa agggcttggt gatcttaagc    1620
ctgggatacc aaaaacacca aagcagaatg gtggtggaaa acgcaagcgc tggactggag    1680
ataaagggcg taagatttat gagtgggatt ctcagcatgg tgagcttgag gggtatcgtg    1740
ccagtgatgg tcagcatctt ggctcatttg acctaaaac aggcaatcag ttgaaaggtc     1800
cagatccgaa acgaaatatc aagaaatatc tttgagagga agttatggga cttaaattgg    1860
atttaacttg gttgataaa agtacagaag atttaaggg tgaggagtat tcaaaagatt      1920
ttggagatga cggttcagtt atggaaagtc taggtgtgcc ttttaaggat aatgttaata    1980
acggttgctt tgatgttata gctgaatggg tacctttgct acaaccatac tttaatcatc    2040
aaattgatat ttccgataat gagtattttg tttcgtttga ttatcgtgat ggtgattggt    2100
gagcggccgc ccattgctgt gg                                             2122
```

<210> SEQ ID NO 10
<211> LENGTH: 1273
<212> TYPE: PRT
<213> ORGANISM: Artificial Sequence
<220> FEATURE:
<223> OTHER INFORMATION: NCBI Reference Sequence: NC_045512.2

<400> SEQUENCE: 10

```
Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
            85                  90                  95

Lys Ser Asn Ile Ile Arg Gly Trp Ile Phe Gly Thr Thr Leu Asp Ser
        100                 105                 110

Lys Thr Gln Ser Leu Leu Ile Val Asn Asn Ala Thr Asn Val Val Ile
    115                 120                 125

Lys Val Cys Glu Phe Gln Phe Cys Asn Asp Pro Phe Leu Gly Val Tyr
130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
            165                 170                 175

Met Asp Leu Glu Gly Lys Gln Gly Asn Phe Lys Asn Leu Arg Glu Phe
        180                 185                 190

Val Phe Lys Asn Ile Asp Gly Tyr Phe Lys Ile Tyr Ser Lys His Thr
    195                 200                 205

Pro Ile Asn Leu Val Arg Asp Leu Pro Gln Gly Phe Ser Ala Leu Glu
210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
            245                 250                 255

Gly Trp Thr Ala Gly Ala Ala Ala Tyr Tyr Val Gly Tyr Leu Gln Pro
        260                 265                 270

Arg Thr Phe Leu Leu Lys Tyr Asn Glu Asn Gly Thr Ile Thr Asp Ala
    275                 280                 285

Val Asp Cys Ala Leu Asp Pro Leu Ser Glu Thr Lys Cys Thr Leu Lys
290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
            325                 330                 335

Pro Phe Gly Glu Val Phe Asn Ala Thr Arg Phe Ala Ser Val Tyr Ala
        340                 345                 350

Trp Asn Arg Lys Arg Ile Ser Asn Cys Val Ala Asp Tyr Ser Val Leu
    355                 360                 365

Tyr Asn Ser Ala Ser Phe Ser Thr Phe Lys Cys Tyr Gly Val Ser Pro
370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
            405                 410                 415
```

```
Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
        450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
            565                 570                 575

Arg Asp Pro Gln Thr Leu Glu Ile Leu Asp Ile Thr Pro Cys Ser Phe
        580                 585                 590

Gly Gly Val Ser Val Ile Thr Pro Gly Thr Asn Thr Ser Asn Gln Val
            595                 600                 605

Ala Val Leu Tyr Gln Asp Val Asn Cys Thr Glu Val Pro Val Ala Ile
        610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
            645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
            725                 730                 735

Asp Cys Thr Met Tyr Ile Cys Gly Asp Ser Thr Glu Cys Ser Asn Leu
        740                 745                 750

Leu Leu Gln Tyr Gly Ser Phe Cys Thr Gln Leu Asn Arg Ala Leu Thr
            755                 760                 765

Gly Ile Ala Val Glu Gln Asp Lys Asn Thr Gln Glu Val Phe Ala Gln
        770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
            805                 810                 815

Phe Ile Glu Asp Leu Leu Phe Asn Lys Val Thr Leu Ala Asp Ala Gly
        820                 825                 830
```

```
Phe Ile Lys Gln Tyr Gly Asp Cys Leu Gly Asp Ile Ala Arg Asp
            835                 840                 845

Leu Ile Cys Ala Gln Lys Phe Asn Gly Leu Thr Val Leu Pro Pro Leu
850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Ala Ser Ala
            930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Lys Val Glu Ala Glu Val Gln
                980                 985                 990

Ile Asp Arg Leu Ile Thr Gly Arg Leu Gln Ser Leu Gln Thr Tyr Val
            995                 1000                1005

Thr Gln Gln Leu Ile Arg Ala Ala Glu Ile Arg Ala Ser Ala Asn
            1010                1015                1020

Leu Ala Ala Thr Lys Met Ser Glu Cys Val Leu Gly Gln Ser Lys
            1025                1030                1035

Arg Val Asp Phe Cys Gly Lys Gly Tyr His Leu Met Ser Phe Pro
            1040                1045                1050

Gln Ser Ala Pro His Gly Val Val Phe Leu His Val Thr Tyr Val
            1055                1060                1065

Pro Ala Gln Glu Lys Asn Phe Thr Thr Ala Pro Ala Ile Cys His
            1070                1075                1080

Asp Gly Lys Ala His Phe Pro Arg Glu Gly Val Phe Val Ser Asn
            1085                1090                1095

Gly Thr His Trp Phe Val Thr Gln Arg Asn Phe Tyr Glu Pro Gln
            1100                1105                1110

Ile Ile Thr Thr Asp Asn Thr Phe Val Ser Gly Asn Cys Asp Val
            1115                1120                1125

Val Ile Gly Ile Val Asn Asn Thr Val Tyr Asp Pro Leu Gln Pro
            1130                1135                1140

Glu Leu Asp Ser Phe Lys Glu Glu Leu Asp Lys Tyr Phe Lys Asn
            1145                1150                1155

His Thr Ser Pro Asp Val Asp Leu Gly Asp Ile Ser Gly Ile Asn
            1160                1165                1170

Ala Ser Val Val Asn Ile Gln Lys Glu Ile Asp Arg Leu Asn Glu
            1175                1180                1185

Val Ala Lys Asn Leu Asn Glu Ser Leu Ile Asp Leu Gln Glu Leu
            1190                1195                1200

Gly Lys Tyr Glu Gln Tyr Ile Lys Trp Pro Trp Tyr Ile Trp Leu
            1205                1210                1215

Gly Phe Ile Ala Gly Leu Ile Ala Ile Val Met Val Thr Ile Met
            1220                1225                1230

Leu Cys Cys Met Thr Ser Cys Cys Ser Cys Leu Lys Gly Cys Cys
```

```
              1235                1240                1245

Ser Cys Gly Ser Cys Cys Lys Phe Asp Glu Asp Ser Glu Pro
        1250                1255                1260

Val Leu Lys Gly Val Lys Leu His Tyr Thr
        1265                1270

<210> SEQ ID NO 11
<211> LENGTH: 199
<212> TYPE: PRT
<213> ORGANISM: Artificial Sequence
<220> FEATURE:
<223> OTHER INFORMATION: Wuhan spike protein Receptor Binding Domain
      (RBD) with 4 additional amino acids

<400> SEQUENCE: 11

Asn Ile Thr Asn Leu Cys Pro Phe Gly Glu Val Phe Asn Ala Thr Arg
1               5                   10                  15

Phe Ala Ser Val Tyr Ala Trp Asn Arg Lys Arg Ile Ser Asn Cys Val
            20                  25                  30

Ala Asp Tyr Ser Val Leu Tyr Asn Ser Ala Ser Phe Ser Thr Phe Lys
        35                  40                  45

Cys Tyr Gly Val Ser Pro Thr Lys Leu Asn Asp Leu Cys Phe Thr Asn
50                  55                  60

Val Tyr Ala Asp Ser Phe Val Ile Arg Gly Asp Glu Val Arg Gln Ile
65                  70                  75                  80

Ala Pro Gly Gln Thr Gly Lys Ile Ala Asp Tyr Asn Tyr Lys Leu Pro
                85                  90                  95

Asp Asp Phe Thr Gly Cys Val Ile Ala Trp Asn Ser Asn Asn Leu Asp
            100                 105                 110

Ser Lys Val Gly Gly Asn Tyr Asn Tyr Leu Tyr Arg Leu Phe Arg Lys
        115                 120                 125

Ser Asn Leu Lys Pro Phe Glu Arg Asp Ile Ser Thr Glu Ile Tyr Gln
130                 135                 140

Ala Gly Ser Thr Pro Cys Asn Gly Val Glu Gly Phe Asn Cys Tyr Phe
145                 150                 155                 160

Pro Leu Gln Ser Tyr Gly Phe Gln Pro Thr Asn Gly Val Gly Tyr Gln
                165                 170                 175

Pro Tyr Arg Val Val Val Leu Ser Phe Glu Leu Leu His Ala Pro Ala
            180                 185                 190

Thr Val Cys Gly Pro Lys Pro
        195

<210> SEQ ID NO 12
<211> LENGTH: 136
<212> TYPE: PRT
<213> ORGANISM: Artificial Sequence
<220> FEATURE:
<223> OTHER INFORMATION: peptide containing P28 dimer, separated by a
      portion of the Vibrio vulnificus flagellin with flexible linkers

<400> SEQUENCE: 12

Lys Phe Leu Thr Thr Ala Lys Asp Lys Asn Arg Trp Glu Asp Pro Gly
1               5                   10                  15

Lys Gln Leu Tyr Asn Val Glu Ala Thr Ser Tyr Ala Gly Gly Gly Gly
            20                  25                  30

Ser Gly Gly Gly Gly Ser Gly Gly Gly Gly Ser Ala Gln Thr Ala Glu
        35                  40                  45

Gly Ala Met Asn Glu Thr Thr Asn Ile Leu Gln Arg Met Arg Asp Leu
```

```
                        50                  55                  60

Ser Leu Gln Ser Ala Asn Gly Ser Asn Ser Lys Ser Glu Arg Val Ala
 65                  70                  75                  80

Ile Gln Glu Glu Ile Thr Ala Leu Asn Asp Glu Leu Asn Gly Gly Gly
                 85                  90                  95

Gly Ser Gly Gly Gly Gly Ser Gly Gly Gly Ser Lys Phe Leu Thr
                100                 105                 110

Thr Ala Lys Asp Lys Asn Arg Trp Glu Asp Pro Gly Lys Gln Leu Tyr
             115                 120                 125

Asn Val Glu Ala Thr Ser Tyr Ala
         130                 135

<210> SEQ ID NO 13
<211> LENGTH: 510
<212> TYPE: DNA
<213> ORGANISM: Artificial Sequence
<220> FEATURE:
<223> OTHER INFORMATION: A yebF fusion with 38 amino acids of the RBD

<400> SEQUENCE: 13
atggctaaaa aaagaggggc gttttttaggg ctgttgttgg tttctgcctg cgcatcagtt      60
ttcgctgcca ataatgaaac cagcaagtcg gtcacttttcc caaagtgtga agatctggat     120
gctgccggaa ttgccgcgag cgtaaaacgt gattatcaac aaaatcgcgt ggcgcgttgg     180
gcagatgatc aaaaaattgt cggtcaggcc gatcccgtgg cttgggtcag tttgcaggac     240
attcagggta agatgataa atggtcagta ccgctaaccg tcgtggtaa agtgccgat        300 attcattacc aggtcagcgt ggactgcaaa gcgggaatgg cggaatatca gcggcgtctc     360
gagggtacta gtggcggtgg tggcagttgc tattttccac tgcagtctta tggctttcag     420
ccgactaacg gtgtgggtta ccaaccgtac cgtgtggttg tactgtcttt cgagctgctg     480
catgccccgg caaccgtatg ctaatctaga                                        510

<210> SEQ ID NO 14
<211> LENGTH: 6822
<212> TYPE: DNA
<213> ORGANISM: Artificial Sequence
<220> FEATURE:
<223> OTHER INFORMATION: plasmid is containing a YebF with in-frame
      fusions of a truncated p28 (p13), a 38 amino acid portion of the
      spike protein RBD, with co-expression of E3, E3 immunity, E8
      immunity, and E3 lysis protein

<400> SEQUENCE: 14
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg caaatattc      180 tgaaatgagc tgttgacaat taatcatccg gctcgtataa tgtgtggaat tgtgagcgga     240
taacaatttc acacaggaaa cagaccatgg ctaaaaaaag agggcgtttt ttagggctgt     300
tgttggtttc tgcctgcgca tcagtttcg ctgccaataa tgaaaccagc aagtcggtca     360
ctttcccaaa gtgtgaagat ctggatgctg ccggaattgc cgcgagcgta aaacgtgatt     420
atcaacaaaa tcgcgtggcg cgttgggcag atgatcaaaa aattgtcggt caggccgatc     480
ccgtggcttg ggtcagtttg caggacattc agggtaaaga tgataaatgg tcagtaccgc     540
taaccgtgcg tggtaaaagt gccgatattc attaccaggt cagcgtggac tgcaaagcgg     600
gaatggcgga atatcagcgg cgtctcgagg gcggtggtgg cagtggaaaa caattataca     660
```

```
atgtggaagc aacttcgtac gcaggcggcg gtggtagcgg cggcggcgga agcggcggtg      720
gcggttctgg caagcaactc tacaatgtcg aggccacttc atacggcggt ggtggcagta      780
ctagtggcgg tggtggcagt tgctattttc cactgcagtc ttatggcttt cagccgacta      840
acggtgtggg ttaccaaccg taccgtgtgg ttgtactgtc tttcgagctg ctgcatgccc      900
cggcaaccgt atgctaatct agagtcgacc tgcaggcatg caagcttggc tgttttggcg      960
gatgagagaa gattttcagc ctgatacaga ttaaatcaga acgcagaagc ggtctgataa     1020
aacagaattt gcctggcggc agtagcgcgg tggtcccacc tgaccccatg ccgaactcag     1080
aagtgaaacg ccgtagcgcc gatggtagtg tggggtctcc ccatgcgaga gtagggaact     1140
gccaggcatc aaataaaacg aaaggctcag tcgaaagact gggcctttcg ttttatctgt     1200
tgtttgtcgg tgaacgctct cctgagtagg acaaatccgc cgggagcgga tttgaacgtt     1260
gcgaagcaac ggcccggagg gtggcgggca ggacgcccgc cataaactgc caggcatcaa     1320
attaagcaga aggccatcct gacgatggc cttttgcgt ttctacaaac tcttttttgtt     1380 tatttttcta aatacattca aatatgtatc cgctcatgag acaataaccc tgataaatgc     1440
ttcaataata ttgaaaaagg aagagtatga gtattcaaca tttccgtgtc gcccttattc     1500 cctttttttgc ggcattttgc cttcctgttt ttgctcaccc agaaacgctg gtgaaagtaa     1560
aagatgctga agatcagttg ggtgcacgag tgggttacat cgaactggat ctcaacagcg     1620
gtaagatcct tgagagtttt cgccccgaag aacgttttcc aatgatgagc acttttaaag     1680
ttctgctatg tggcgcggta ttatcccgtg ttgacgccgg gcaagagcaa ctcggtcgcc     1740
gcatacacta ttctcagaat gacttggttg agtactcacc agtcacagaa aagcatctta     1800
cggatggcat gacagtaaga gaattatgca gtgctgccat aaccatgagt gataacactg     1860
cggccaactt acttctgaca acgatcggag gaccgaagga gctaaccgct ttttttgcaca     1920 acatggggga tcatgtaact cgccttgatc gttgggaacc ggagctgaat gaagccatac     1980
caaacgacga gcgtgacacc acgatgccta cagcaatggc aacaacgttg cgcaaactat     2040
taactggcga actacttact ctagcttccc ggcaacaatt aatagactgg atggaggcgg     2100
ataaagttgc aggaccactt ctgcgctcgg cccttccggc tggctggttt attgctgata     2160
aatctggagc cggtgagcgt gggtctcgcg gtatcattgc agcactgggg ccagatggta     2220
agccctcccg tatcgtagtt atctacacga cggggagtca ggcaactatg gatgaacgaa     2280
atagacagat cgctgagata ggtgcctcac tgattaagca ttggtaactg tcagaccaag     2340
tttactcata tactttttag attgatttaa aacttcattt ttaatttaaa aggatctagg     2400
tgaagatcct ttttgataat ctcatgacca aaatccctta acgtgagttt cgttccact      2460 gagcgtcaga ccccgtagaa aagatcaaag gatcttcttg agatcctttt tttctgcgcg     2520
taatctgctg cttgcaaaca aaaaaaccac cgctaccagc ggtggtttgt ttgccggatc     2580
aagagctacc aactctttt ccgaaggtaa ctggcttcag cagagcgcag ataccaaata     2640
ctgtccttct agtgtagccg tagttaggcc accacttcaa gaactctgta gcaccgccta     2700
catacctcgc tctgctaatc ctgttaccag tggctgctgc cagtggcgat aagtcgtgtc     2760
ttaccgggtt ggactcaaga cgatagttac cggataaggc gcagcggtcg ggctgaacgg     2820
ggggttcgtg cacacagccc agcttggagc gaacgaccta caccgaactg agatacctac     2880
agcgtgagct atgagaaagc gccacgcttc ccgaagggag aaaggcggac aggtatccgg     2940
taagcggcag ggtcggaaca ggagagcgca cgagggagct tccaggggga aacgcctggt     3000
```

```
atctttatag tcctgtcggg tttcgccacc tctgacttga gcgtcgattt ttgtgatgct    3060 cgtcagggg gcggagccta tggaaaaacg ccagcaacgc ggccttttta cggttcctgg    3120
ccttttgctg gccttttgct cacatgttct ttcctgcgtt atccctgat tctgtggata     3180 accgtattac cgcctttgag tgagctgata ccgctcgccg cagccgaacg accgagcgca    3240
gcgagtcagt gagcgaggaa gcggaagagc gcctgatgcg gtattttctc cttacgcatc    3300
tgtgcggtat ttcacaccgc atatgcccgc tctgcgtttt ctaagtgtta ccctcctga    3360 tttctaaaaa attttccacc tgaacttgac agaaaaaacg atgacgagta cttttgatc    3420 tgtacataaa cccagtggtt ttatgtacag tattaatcgt gtaatcaatt gttttaacgc    3480
ttaaaagagg gaattttat gagcggtggc gatggacgcg ccataacac gggcgcgcat      3540 agcacaagtg gtaacattaa tggtggcccg accgggcttg gtgtaggtgg tggtgcttct    3600
gatggctccg gatggagttc ggaaaataac ccgtggggtg gtggttccgg tagcggcatt    3660
cactggggtg gtggttccgg tcatggtaat ggcgggggga atggtaattc cgtggtggt    3720 tcgggaacag gcggtaatct gtcagcagta gctgcgccag tggcatttgg ttttccggca    3780
ctttccactc caggagctgg cggtctggcg gtcagtattt cagcgggagc attatcggca    3840
gctattgctg atattatggc tgccctgaaa ggaccgttta aatttggtct ttgggggtg     3900 gctttatatg gtgtattgcc atcacaaata gcgaagatg accccaatat gatgtcaaag     3960
attgtgacgt cattacccgc agatgatatt actgaatcac ctgtcagttc attacctctc    4020
gataaggcaa cagtaaacgt aaatgttcgt gttgttgatg atgtaaaaga cgagcgacag    4080
aatatttcgg ttgtttcagg tgttccgatg agtgttccgg tggttgatgc aaaacctacc    4140
gaacgtccgg gtgttttttac ggcatcaatt ccaggtgcac ctgttctgaa tatttcagtt    4200
aataacagta cgccagcagt acagacatta agcccaggtg ttacaaataa tactgataag    4260
gatgttcgcc cggcaggatt tactcagggt ggtaatacca gggatgcagt tattcgattc    4320
ccgaaggaca gcgtcataa tgccgtatat gtttcagtga gtgatgttct tagccctgac    4380
caggtaaaac aacgtcaaga tgaagaaaat cgccgtcagc aggaatggga tgctacgcat    4440
ccggttgaag cggctgagcg aaattatgaa cgcgcgcgtg cagagctgaa tcaggcaaat    4500
gaagatgttg ccagaaatca ggagcgacag gctaaagctg ttcaggttta taattcgcgt    4560
aaaagcgaac ttgatgcagc gaataaaact cttgctgatg caatagctga ataaaacaa    4620 tttaatcgat ttgcccatga cccaatggct ggcggtcaca gaatgtggca atggccggg    4680 cttaaagccc agcgggcgca gacggatgta aataataagc aggctgcatt tgatgctgct    4740
gcaaaagaga agtcagatgc tgatgctgca ttgagttctg ctatggaaag caggaagaag    4800
aaagaagata gaaaaggag tgctgaaaat aatttaaacg atgaaaagaa taagcccaga    4860
aaaggtttta agattacgg gcatgattat catccagctc cgaaaactga gaatattaaa    4920
gggcttggtg atcttaagcc tgggatacca aaaacaccaa gcagaatgg tggtggaaaa    4980 cgcaagcgct ggactggaga taagggcgt aagatttatg agtgggattc tcagcatggt    5040
gagcttgagg ggtatcgtgc cagtgatggt cagcatcttg gctcatttga ccctaaaaca    5100
ggcaatcagt tgaaaggtcc agatccgaaa cgaaatatca agaatatct tgagaggaa     5160 gttatgggac ttaaattgga tttaacttgg tttgataaaa gtacagaaga ttttaagggt    5220
gaggagtatt caaaagattt tggagatgac ggttcagtta tggaaagtct aggtgtgcct    5280
tttaaggata atgttaataa cggttgcttt gatgttatag ctgaatgggt acctttgcta    5340
caaccatact ttaatcatca aattgatatt tccgataatg agtattttgt ttcgtttgat    5400
```

```
tatcgtgatg gtgattggtg atcaaatatt atcagggatg agttgatata cgggcttcta    5460
gtgttcatgg atgaacgctg gagcctccaa atgtagaaat gttatatttt ttattgagtt    5520
cttggttata attgctccgc aatgatttaa ataagcatta tttaaaacat tctcaggaga    5580
ggtgaaggtg gagctaaaaa aaagtattgg tgattacact gaaaccgaat tcaaaaaatt    5640
tattgaagac atcatcaatt gtgaaggtga tgaaaaaaaa caggatgata acctcgagta    5700
ttttataaat gttactgagc atcctagtgg ttctgatctg atttattacc cagaaggtaa    5760
taatgatggt agccctgaag gtgttattaa agagattaaa gaatggcgag ccgctaacgg    5820
taagtcagga tttaaacagg gctgaaatat gaatgccggt tgtttatgga tgaatggctg    5880
gcattctttc acaacaagga gtcgttatga aaaaataac agggattatt ttattgcttc    5940
ttgcagtcat tattctgtct gcatgtcagg caaactatat ccgggatgtt cagggcggga    6000
ccgtatctcc gtcatcaaca gctgaagtga ccggattagc aacgcagtaa cccgaaatcc    6060
tctttgacaa aaacaaagcg tgtcaggctg cggccgccca ttgctgtgga agctgcctgc    6120
actaatgttc cggcgttatt tcttgatgtc tctgaccaga cacccatcaa cagtattatt    6180
ttctcccatg aagacggtac gcgactgggc gtggagcatc tggtcgcatt gggtcaccag    6240
caaatcgcgc tgttagcggg cccattaagt tctgtctcgg cgcgtctgcg tctggctggc    6300
tggcataaat atctcactcg caatcaaatt cagccgatag cggaacggga aggcgactgg    6360
agtgccatgt ccggttttca acaaaccatg caaatgctga atgagggcat cgttcccact    6420
gcgatgctgg ttgccaacga tcagatggcg ctgggcgcaa tgcgcgccat taccgagtcc    6480
gggctgcgcg ttggtgcgga tatctcggta gtgggatacg acgataccga agacagctca    6540
tgttatatcc cgccgttaac caccatcaaa caggattttc gcctgctggg caaaccagc     6600 gtggaccgct tgctgcaact ctctcagggc caggcggtga agggcaatca gctgttgccc    6660
gtctcactgg tgaaaagaaa aaccaccctg gcgcccaata cgcaaaccgc ctctccccgc    6720
gcgttggccg attcattaat gcagctggca cgacaggttt cccgactgga aagcgggcag    6780
tgagcgcaac gcaattaatg tgagttagcg cgaattgatc tg                      6822
```

<210> SEQ ID NO 15
<211> LENGTH: 38
<212> TYPE: PRT
<213> ORGANISM: Artificial Sequence
<220> FEATURE:
<223> OTHER INFORMATION: SARS-Cov-2 (Wuhan-Hu-1 NC_045512.2) Receptor
      Binding Domain, residues 488-525

<400> SEQUENCE: 15

```
Cys Tyr Phe Pro Leu Gln Ser Tyr Gly Phe Gln Pro Thr Asn Gly Val
1               5                   10                  15

Gly Tyr Gln Pro Tyr Arg Val Val Val Leu Ser Phe Glu Leu Leu His
            20                  25                  30

Ala Pro Ala Thr Val Cys
        35
```

EXPRESSION OF SARS-COV-2 SPIKE PROTEIN RECEPTOR BINDING DOMAIN IN ATTENUATED SALMONELLA AS A VACCINE

FIELD OF THE INVENTION

The present invention relates to the field of live bacterial vectors as vaccines, and more particularly to a live attenuated bacteria expressing a portion of the SARS-CoV-2 spike protein receptor binding domain, adapted for oral administration to a human without substantial morbidity and to induce an effective preventative vaccine response.

BACKGROUND OF THE INVENTION

Coronavirus disease 2019 (COVID-19) is an infectious disease caused by severe acute respiratory syndrome coronavirus 2 (SARS-CoV-2). It was first identified in Wuhan, China, and has since spread globally, resulting in an ongoing pandemic. As of 10 May 2020, more than 4.08 million cases have been reported across 187 countries and territories, resulting in more than 281,000 deaths. More than 1.39 million people have been infected. en.wikipedia.org/wiki/Coronavirus_disease_2019.

Common symptoms include fever, cough, fatigue, shortness of breath, and loss of smell and taste. While the majority of cases result in mild symptoms, some progress to acute respiratory distress syndrome (ARDS), multi-organ failure, septic shock, and blood clots. The time from exposure to onset of symptoms is typically around five days but may range from two to fourteen days.

The virus is believed to be spread between people during close contact, most often via small droplets produced by coughing, sneezing, and talking. It is most contagious during the first three days after the onset of symptoms, although spread may be possible before symptoms appear, or from people who do not show symptoms. The standard method of diagnosis is by real-time reverse transcription polymerase chain reaction (rRT-PCR) from a nasopharyngeal swab. Chest CT imaging may also be helpful for diagnosis in individuals where there is a high suspicion of infection based on symptoms and risk factors; however, guidelines do not recommend using it for routine screening. Chest X-ray shows a characteristic ground glass appearance.

As is common with infections, there is a delay between the moment a person is first infected and the time he or she develops symptoms. This is called the incubation period. The incubation period for COVID 19 is typically five to six days but may range from two to 14 days, although 97.5% of people who develop symptoms will do so within 11.5 days of infection.

A minority of cases do not develop noticeable symptoms at any point in time. These asymptomatic carriers tend not to get tested, and their role in transmission is not yet fully known. However, preliminary evidence suggests they may contribute to the spread of the disease.

SARS-CoV-2 is closely related to the original SARS-CoV. [6] It is thought to have a zoonotic origin. Genetic analysis has revealed that the coronavirus genetically clusters with the genus Betacoronavirus, in subgenus Sarbecovirus (lineage B) together with two bat-derived strains. It is 96% identical at the whole genome level to other bat coronavirus samples (BatCov RaTG13). In February 2020, Chinese researchers found that there is only one amino acid difference in the binding domain of the S protein between the coronaviruses from pangolins and those from humans; however, whole-genome comparison to date found that at most 92% of genetic material was shared between pangolin coronavirus and SARS-CoV-2, which is insufficient to prove pangolins to be the intermediate host. [7]

The lungs are the organs most affected by COVID 19 because the virus accesses host cells via the enzyme angiotensin-converting enzyme 2 (ACE2), which is most abundant in type II alveolar cells of the lungs. The virus uses a special surface glycoprotein called a "spike" (peplomer) to connect to ACE2 and enter the host cell. [8] The density of ACE2 in each tissue correlates with the severity of the disease in that tissue and some have suggested that decreasing ACE2 activity might be protective, [9][10] though another view is that increasing ACE2 using angiotensin II receptor blocker medications could be protective and these hypotheses need to be tested. [11] As the alveolar disease progresses, respiratory failure might develop and death may follow. [10]

The virus also affects gastrointestinal organs as ACE2 is abundantly expressed in the glandular cells of gastric, duodenal and rectal epithelium[12] as well as endothelial cells and enterocytes of the small intestine. [13]

The virus can cause acute myocardial injury and chronic damage to the cardiovascular system. [14] Rates of cardiovascular symptoms are high, owing to the systemic inflammatory response and immune system disorders during disease progression, but acute myocardial injuries may also be related to ACE2 receptors in the heart. [14] ACE2 receptors are highly expressed in the heart and are involved in heart function. [14][15]

Although SARS-COV-2 has a tropism for ACE2-expressing epithelial cells of the respiratory tract, patients with severe COVID 19 have symptoms of systemic hyperinflammation. Clinical laboratory findings of elevated IL-2, IL-7, IL-6, granulocyte-macrophage colony-stimulating factor (GM-CSF), interferon-γ inducible protein 10 (IP-10), monocyte chemoattractant protein 1 (MCP-1), macrophage inflammatory protein 1-α (MIP-1α), and tumour necrosis factor-α (TNF-α) indicative of cytokine release syndrome (CRS) suggest an underlying immunopathology. Additionally, people with COVID 19 and acute respiratory distress syndrome (ARDS) have classical serum biomarkers of CRS, including elevated C-reactive protein (CRP), lactate dehydrogenase (LDH), D-dimer, and ferritin. [16]

Systemic inflammation results in vasodilation, allowing inflammatory lymphocytic and monocytic infiltration of the lung and the heart. In particular, pathogenic GM-CSF-secreting T-cells were shown to correlate with the recruitment of inflammatory IL-6-secreting monocytes and severe lung pathology in COVID 19 patients. [17]

It is unknown if past infection provides effective and long-term immunity in people who recover from the disease. [18][19] Some of the infected have been reported to develop protective antibodies, so acquired immunity is presumed likely, based on the behaviour of other coronaviruses. [20] However, cases in which recovery from COVID 19 was followed by positive tests for coronavirus at a later date have been reported. [21][22][23][24] These cases are believed to be lingering infection rather than reinfection,[24] or false positives due to remaining RNA fragments. [15] Some other coronaviruses circulating in people are capable of reinfection after roughly a year. [26][27]

Three vaccination strategies are generally being investigated. First, researchers aim to build a whole virus vaccine. The use of such a virus, be it inactive or dead, aims to elicit a prompt immune response of the human body to a new infection with COVID 19. A second strategy, subunit vaccines, aims to create a vaccine that sensitizes the immune system to certain subunits of the virus. In the case of SARS-CoV-2, such research focuses on the S-spike protein that helps the virus intrude the ACE2 enzyme receptor. A third strategy is that of the nucleic acid vaccines (DNA or RNA vaccines). Experimental vaccines from any of these strategies would have to be tested for safety and efficacy. [28] Antibody-dependent enhancement has been suggested as a potential challenge for vaccine development for SARS-COV-2, but this is controversial. [29]

Cytokine release syndrome (CRS) can be a complication in the later stages of severe COVID 19. There is preliminary evidence that hydroxychloroquine may have anti-cytokine storm properties. [30]

Tocilizumab has been included in treatment guidelines by China's National Health Commission after a small study was completed. [31][32] It is undergoing a phase 2 non-randomised trial at the national level in Italy after showing positive results in people with severe disease. [33][34] Combined with a serum ferritin blood test to identify cytokine storms, it is meant to counter such developments, which are thought to be the cause of death in some affected people. [35][36][37] The interleukin-6 receptor antagonist was approved by the FDA to undergo a phase III clinical trial assessing the medication's impact on COVID 19 based on retrospective case studies for the treatment of steroid-refractory cytokine release syndrome induced by a different cause, CAR T cell therapy, in 2017. [38] Lenzilumab, an anti-GM-CSF monoclonal antibody, is protective in murine models for CAR T cell-induced CRS and neurotoxicity and is a viable therapeutic option due to the observed increase of pathogenic GM-CSF secreting T-cells in hospitalised patients with COVID 19. [39]

The Feinstein Institute of Northwell Health announced in March a study on "a human antibody that may prevent the activity" of IL-6. [40]

Transferring purified and concentrated antibodies produced by the immune systems of those who have recovered from COVID 19 to people who need them is being investigated as a non-vaccine method of passive immunisation. [41] This strategy was tried for SARS with inconclusive results. [41] Viral neutralisation is the anticipated mechanism of action by which passive antibody therapy can mediate defence against SARS-CoV-2. Other mechanisms, however, such as antibody-dependent cellular cytotoxicity and/or phagocytosis, may be possible. [41] Other forms of passive antibody therapy, for example, using manufactured monoclonal antibodies, are in development. [41] Production of convalescent serum, which consists of the liquid portion of the blood from recovered patients and contains antibodies specific to this virus, could be increased for quicker deployment. [42]

The world experienced the outbreaks of coronavirus infection that threaten global pandemic in 2002-2003 by Severe Acute Respiratory Syndrome (SARS) and in 2011 by Middle East Respiratory Syndrome (MERS). In both cases, the causative agents (SARS-CoV and MERS-CoV, respectively) were newly identified coronavirus in the genus Betacoronavirus with zoonotic origin. At the end of 2019, outbreak of another coronavirus that causes respiratory-related illness was reported in Wuhan, Hubei, China, a disease now officially called "the Corona Virus Disease 2019; COVID-19". The coronavirus that is the causative agent of this respiratory disease was identified and its genome is fully sequenced. [42] The genomic sequence of SARS-CoV-2 showed similar, but distinct genome composition of SARS-CoV and MERS-CoV. Since its first reported case in late 2019, the infection has spread to other regions in China and other countries, and the transmission rate, the mortality rate and the clinical manifestation slowly emerged. However, it will take months and maybe years until we will fully grasp the whole picture of the characteristics of the pathogens and its likely origin, symptoms and the host immune responses to combat the infection. [83]

Identification of SARS-CoV-2 tropism is also warranted. In agreement with genome similarity with SARS, analysis of nucleic acid sequence within the spike protein receptor-binding domain (RBD) has been predicted that SAR-CoV-2 might also use angiotensin-converting enzyme 2 (ACE2) as a cell receptor. [43] The study performed in vitro experiments which could confirm that SAR-CoV-2 used ACE2 for cellular entry. [44] Because wild range of animal species (except rat and mouse) express ACE2, it could support the observed cross-species and human-to-human transmission events.

Currently, only limited information is available on the host innate immune status of SARS-CoV-2 infected patients. In one report where 99 cases in Wuhan were investigated, increased total neutrophils (38%), reduced total lymphocytes (35%), increased serum IL-6 (52%) and increased c-reactive protein (84%) were observed. [45] In a separate report also from Wuhan, it revealed that in 41 patients, increased total neutrophils, decreased total lymphocytes in patients of ICU vs. non-ICU care were found to be statistically different. Increased neutrophils and decreased lymphocytes also correlate with disease severity and death. Furthermore, patients needing ICU care had higher plasma levels of many innate cytokines, IP-10, MCP-1, MIP-1A, and TNFα. [46] These clinical features suggested the likelihood of involvement of highly pro-inflammatory condition in the disease progression and severity. This early high rise in the serum levels of pro-inflammatory cytokines were also observed in SARS-CoV and MERS-CoV infection, suggesting a potential similar cytokine storm-mediated disease severity. [47][48]Effective innate immune response against viral infection relies heavily on the interferon (IFN) type I responses and its downstream cascade that culminates in controlling viral replication and induction of effective adaptive immune response. While SARS-CoV and SARS-CoV-2 seem to share the entry receptor of ACE2, MERS-CoV uses dipeptidyl peptidase (DPP)-4 as a specific receptor. [45] The putative receptor of SARS-CoV-2, ACE2, is mainly expressed in a small subset of cells in the lung called type 2 alveolar cells. It has been reported that SARS-CoV directly infects macrophages and T cells, a key feature in SARS-CoV-mediated pathogenesis. [49] Whether SARS-CoV-2 infects any immune cells are still unknown. Only minimal percentages of monocytes/macrophages in the lung expressed ACE2. [50] If ACE2 is minimally expressed in the potential target immune cells, it is possible that other receptors may exist, or other cellular entry mode is utilized such as antibody-dependent enhancement.

To mount an antiviral response, innate immune cells need to recognize the invasion of the virus, often by pathogen-associated molecular patterns (PAMPs). For RNA virus such as coronavirus, it is known that PAMPs in the form of viral genomic RNA or the intermediates during viral replication including dsRNA, are recognized by either the endosomal RNA receptors, TLR3 and TLR7 and the cytosolic RNA sensor, RIG-I/MDA5. This recognition event leads to activation of the downstream signaling cascade, i.e. NF-κB and IRF3, accompanied by their nuclear translocation. In the nuclei, these transcription factors induce expression of type I IFN and other pro-inflammatory cytokines and this initial responses comprise the first line defense against viral infection at the entry site. [51] Type I IFN via IFNAR, in turn, activates the JAK-STAT pathway, where JAK and TYK2 kinases phosphorylate STAT1 and STAT2. STAT1/2 form a complex with IRF9, and together they move into the nucleus to initiate the transcription of IFN-stimulated genes (ISGs) under the control of IFN-stimulated response element (ISRE) containing promoters. A successful mounting of this type I IFN response should be able to suppress viral replication and dissemination at an early stage.

For SARS-CoV and MERS-CoV, the response to viral infection by type I IFN is suppressed. Both coronaviruses employ multiple strategies to interfere with the signaling leading to type I IFN production and/or the signaling downstream of IFNAR. This dampening strategy is closely associated with the disease severity. At the step of type I IFN induction, SARS-CoV interferes with the signaling downstream of RNA sensors directly or indirectly such as ubiquitination and degradation of RNA sensor adaptor molecules MAVS and TRAF3/6 and inhibiting IRF3 nuclear translocation. [52] MERS-CoV also utilizes some of these strategies with additional mechanism such as repressive histone modification. Once type I IFN is secreted, these two viruses are equipped with mechanism that inhibit IFN signaling such as decreasing STAT1 phosphorylation. The viral proteins involved in the modulation of this host type I IFN response are both structural proteins (such as M, N) and non-structural proteins (ORF proteins).

Based on the genomic sequence comparison, SARS-CoV shares overall genomic similarity with SARS-CoV or MERS-CoV, approximately 79% and 50%, respectively. The genome of SARS-CoV-2 also contains additional gene regions (10b, 13, 14). In addition, the amino acid sequences of some putative proteins of SARS-CoV-2 show only 68% similarity with that of SARS-CoV. Therefore, careful sequence comparison of each gene region may yield better prediction as how SARS-CoV-2 interferes with host innate immune response. It is partially speculative that SARS-CoV-2 utilizes similar strategies to modulate the host innate immune response, especially in dampening the type I IFN response but additional novel mechanisms may be uncovered.

Aerosolized uptake of SARS-CoV-2 leads to infection of ACE2 expressing target cells such as alveolar type 2 cells or other unknown target cells. Virus may dampen anti-viral IFN responses resulting in uncontrolled viral replication. The influx of neutrophils and monocytes/macrophages results in hyperproduction of pro-inflammatory cytokines. The immunopathology of lung may be the result of the "cytokine storms". Specific Th1/Th17 may be activated and contributes to exacerbate inflammatory responses. B cells/plasma cells produce SARS-CoV-2 specific antibodies that may help neutralize viruses. The question marks indicated events that are still speculative or unknown.

In the severe or lethal cases of SARS-CoV or MERS-CoV infection, increased neutrophil and monocyte-macrophages influx are consistently observed. [53][54] In a mouse model of SARS-CoV infection, dysregulated type I IFN and inflammatory monocyte-macrophages are the main cause of lethal pneumonia. Therefore, excessive type I IFN with the infiltrated myeloid cells are the main cause of lung dysfunction and negatively impact the outcome of the infection. It is speculated that upon SARS-CoV or MERS-CoV infection, delayed type I IFN compromises the early viral control, leading to influx of hyperinflammatory neutrophils and monocytes-macrophages. The increases in these innate immune cells yields deteriorating consequences to infected host that manifested in lung immunopathology, including pneumonia or acute respiratory distress syndrome. In SARS-CoV-2 infection, similar scenario is expected with varying degree of immune interference. Interestingly, transmission of virus is reported to occur even in asymptomatic infected individuals. This may be indicative of delayed early response of the innate immune response.

Based on the accumulated data for previous coronavirus infection, innate immune response plays crucial role in protective or destructive responses and may open a window for immune intervention. Active viral replication later results in hyperproduction type I IFN and influx of neutrophils and macrophages which are the major sources of pro-inflammatory cytokines. With similar changes in total neutrophils and lymphocytes during COVID19, SARS-CoV-2 probably induces delayed type I IFN and loss of viral control in an early phase of infection. Individuals susceptible to CoVID19 are those with underlying diseases, including diabetes, hypertension, and cardiovascular disease. In addition, no severe cases were reported in young children, when innate immune response is highly effective. These facts strongly indicate that innate immune response is a critical factor for disease outcome.

Based on the assumption that innate immunity plays a key role, several interventions can be proposed. Type I IFN, antagonists of some key pro-inflammatory cytokines and anti-viral agents are some of these examples. When using type I IFN for treatment, in a mouse model of either SARS-CoV or MERSCoV infection, the timing of administration is key to yield protective response. [55]

In general, the Th1 type immune response plays a dominant role in an adaptive immunity to viral infections. Cytokine microenvironment generated by antigen presenting cells dictate the direction of T cell responses. Helper T cells orchestrate the overall adaptive response, while cytotoxic T cells are essential in killing of viral infected cells. Humoral immune response, especially production of neutralizing antibody, plays a protective role by limiting infection at later phase and prevents reinfection in the future. In SARS-CoV, both T and B cell epitopes were extensively mapped for the structural proteins, S, N, M and E protein. [56]

SARS-CoV infection induces seroconversion as early as day 4 after onset of disease and was found in most patients by 14 days. Long lasting specific IgG and neutralizing antibody are reported as long as 2 years after infection. [57] For MERS-CoV infection, seroconversion is seen at the second or third week of disease onset. For both types of coronavirus infections, delayed and weak antibody response are associated with severe outcome. [56] A limited serology details of SARS-CoV-2 was reported. In a preliminary study, one patient showed peak specific IgM at day 9 after disease onset and the switching to IgG by week 2.25 Interestingly, sera from 5 patients of confirmed COVID-19 show some cross-reactivity with SARS-CoV, but not other coronavirus. Furthermore, all sera from patients were able to neutralize SARS-CoV-2 in an in vitro plaque assay, suggesting a possible successful mounting of the humoral responses.

T cell response in SARS-CoV was extensively investigated. In one study using 128 convalescent samples, it was reported that CD8+ T cell responses were more frequent with greater magnitude than CD4+ T cell responses. Furthermore, the virus-specific T cells from the severe group tended to be a central memory phenotype with a significantly higher frequency of polyfunctional CD4+ T cells (IFNγ, TNFα, and IL-2) and CD8+ T cells (IFNγ, TNFα and degranulated state), as compared with the mild-moderate group. Strong T cell responses correlated significantly with higher neutralizing antibody while more serum Th2 cytokines (IL-4, IL-5, IL-10) were detected in the fatal group. [58] For the epitope mapping, most responses (70%) were found against the structural proteins (spike, envelope, membrane, and nucleocapsid). In MERS-CoV infection, early rise of CD8+ T cells correlates with disease severity and at the convalescent phase, dominant Th1 type helper T cells are observed. [59] In an animal model, airway memory CD4+ T cells specific for conserved epitope are protective against lethal challenge and can cross react with SARS-CoV and MERSCoV. [60] As neutrophils play a destructive role in all infections, the protective or destructive role of Th17 in human coronavirus infection remains unanswered.

Current evidences strongly indicated that Th1 type response is a key for successful control of SARS-CoV and MERSCoV and probably true for SARS-CoV-2 as well. CD8+ T cell response, even though crucial, needs to be well controlled in order not to cause lung pathology. Because most epitopes identified for both viruses concentrate on the viral structural proteins, it will be informative to map those epitopes identified with SARS-CoV/MERS-CoV with those of SARS-CoV-2. If overlapping epitopes among the three viruses can be identified, it will be beneficial for application in passive immunization using convalescent serum from recovered SARS or MERS patients. For T cell epitopes, it will help in designing cross reactive vaccine that protect against all three human coronaviruses in the future.

Current observations indicate that coronaviruses are particularly adapted to evade immune detection and dampen human immune responses. This partly explains why they tend to have a longer incubation period, 2-11 days on average compared to influenza, 1-4 days. The longer incubation period is probably due to their immune evasion properties, efficiently escaping host immune detection at the early stage of infection. As a member of the Betacoronavirus genus, immune evasion mechanism is potentially similar to those of SARS-CoV and MERS-CoV. The mechanisms of how SARS-CoV and MERSCoV modulate host immune responses were extensively reviewed and discussed. [61] [62] In brief, most mechanisms rely on the inhibition of innate immune responses, especially type I interferon recognition and signaling. The viral proteins including membrane (M) or nonstructural (NS) proteins (eg. NS4a, NS4b, NS15) are the key molecules in host immune modulation. In agreement with the aforementioned study, analysis of two MERS-CoV-infected individuals with different severity found that the type I interferon response in the poor outcome (death) patient was remarkably lower than the recovered patient. [63] For adaptive immune evasion, antigen presentation via MHC class I and MHC class II was downregulated when the macrophages or dendritic cells were infected with MERS-CoV, which would markedly diminish T cells activation. [61]

Coronaviruses interfere with multiple steps during initial innate immune response, including RNA sensing, signaling pathway of type I IFN production, and STAT1/2 activation downstream of IFN/IFNAR. This delayed or dampening type I IFN responses impinge upon adaptive immune activation. Prolonged viral persistence exacerbates inflammatory responses that may lead to immune exhaustion and immune suppression as a feedback regulatory mechanism. Biased Th2 type response also favors poor outcome of the disease.

Due to the rapid increase of SAR-CoV2 infections and affected countries, efforts toward developing an effective SARCoV2 vaccine have been ignited in many countries. By gaining knowledge from SARS and MERS vaccines development path, several research groups have been able to start SAR-CoV2 vaccine development within only a few weeks after the outbreak. The target antigen selection and vaccine platform are probably based on SARS-CoV and MERS-CoV vaccine studies. Full-length spike (S) or S1 which contains receptor binding domain (RDB) might be considered as a good vaccine antigen because it could induce neutralizing antibodies that prevent host cell attachment and infection. [64][65][66]

A nucleic acid-based vaccine, a DNA vaccine, showed the most advance platform in response to emerging pathogens. Moreover, during Zika virus outbreak, DNA vaccine was the first vaccine candidate that entered clinical trial (NCT02809443) (less than 1-year after the outbreak). According to the current technological advancement, mRNA vaccine, another nucleic acid-based vaccine, has been considered as disruptive vaccine technology. Recent mRNA vaccine designs have improved stability and protein translation efficiency thus it could induce robust immune responses. [67][68] Delivery system such as lipid nanoparticle, LNP was also well-optimized. [69]

By looking at the similarities and differences between the current SARS-CoV-2 and the previous outbreak of SARS and MERS, a striking similarity emerges with some unique features of its own. As the COVID-19 causes serious public health concerns across Asia and on the blink to affect world population, investigation into the characteristics of SARS-CoV-2, its interaction with the host immune responses may help provide a clearer picture of how the pathogen causes diseases in some individuals while most infected people only show mild or no symptoms at all. In addition, the study of the immune correlates of protection and the long-term immune memory from convalescent individuals may help in design prophylactic and therapeutic measures for future outbreak of similar coronaviruses.

SARS-CoV-2 has a genome size of ~30 kilobases which, like other coronaviruses, encodes for multiple structural and non-structural proteins. The structural proteins include the spike (S) protein, the envelope (E) protein, the membrane (M) protein, and the nucleocapsid (N) protein. With SARS-CoV-2 being discovered very recently, there is currently a lack of immunological information available about the virus (e.g., information about immunogenic epitopes eliciting antibody or T cell responses). Preliminary studies suggest that SARS-CoV-2 is quite similar to SARS-CoV based on the full-length genome phylogenetic analysis [70][71], and the putatively similar cell entry mechanism and human cell receptor usage [70][72][73]. Due to this apparent similarity between the two viruses, previous research that has provided an understanding of protective immune responses against SARS-CoV may potentially be leveraged to aid vaccine development for SARS-CoV-2. [84]

Various reports related to SARS-CoV suggest a protective role of both humoral and cell-mediated immune responses. For the former case, antibody responses generated against the S protein, the most exposed protein of SARS-CoV, have been shown to protect from infection in mouse models [70][71][72]. In addition, multiple studies have shown that antibodies generated against the N protein of SARS-CoV, a highly immunogenic and abundantly expressed protein during infection [73], were particularly prevalent in SARS-CoV-infected patients [74][75]. While being effective, the antibody response was found to be short-lived in convalescent SARS-CoV patients [21]. In contrast, T cell responses have been shown to provide long-term protection [76][77] [78], even up to 11 years post-infection [79], and thus have also attracted interest for a prospective vaccine against SARS-CoV [reviewed in [80]]. Among all SARS-CoV proteins, T cell responses against the structural proteins have been found to be the most immunogenic in peripheral blood mononuclear cells of convalescent SARS-CoV patients as compared to the non-structural proteins [81]. Further, of the structural proteins, T cell responses against the S and N proteins have been reported to be the most dominant and long-lasting [82].

The availability of the highly attenuated *Salmonella enterica Typhimurium* strain YS1646 that had been used in a phase 1 clinical cancer trial at doses up to $3 \times 10^8$ IV was attractive for many reasons. Although *S. enterica* species replicate in a membrane-bound host cell compartment or vacuole [85], foreign protein antigens can be efficiently exported from the vacuole into the cytoplasm using the organism's T3SS. Like all *Salmonella enterica* species, YS1646 has two distinct T3SS located in *Salmonella* pathogenicity islands 1 and 2 (SPI-I and SPI-II) [86] that are active at different phases of infection [87]. The SPI-I T3SS translocates proteins upon first contact of the bacterium with epithelium cells through to the stage of early cell invasion while SPI-II expression is induced once the bacterium has been phagocytosed [88]. These T3SS have been used by many groups to deliver heterologous antigens in *Salmonella*-based vaccine development programs [89, 90, reviewed by 91].

In recent years, live attenuated *Salmonella* has been increasingly used to express foreign antigens against infectious diseases and cancers. [92][93][94][95][96][97][98][99][101][102][103][104][105][106][107][108][109]

*Salmonella enterica* is a facultative intracellular pathogen that replicates in a unique membrane-bound host cell compartment, the *Salmonella*-containing vacuole [85]. Although this location limits exposure of both *Salmonella* and foreign proteins produced by the bacterium to the immune system, the organism's type III secretion systems (T3SS) can be exploited to translocate heterologous antigens into the host cell cytoplasm. *Salmonella enterica* encodes two distinct T3SS within the *Salmonella* pathogenicity islands 1 and 2 (SPI-I and SPI-II) that become active at different phases of infection [87]. The SPI-I T3SS translocates effector proteins upon first contact of the bacterium with epithelium cells through to the stage of early cell invasion. In contrast, SPI-II expression is induced when the bacterium has been phagocytosed. Several effector proteins translocated by these T3SSs have been tested in the promotion of heterologous antigen expression in *Salmonella*-based vaccine development programs but how effector protein-mediated secretion of heterologous antigens affects immune responses is still poorly understood. [89][111]

There is considerable experience in using the attenuated *S. typhi* vaccine strain (Ty21a: Vivotif™) in the delivery of heterologous antigens. [89] However, *S. typhimurium* YS1646 was selected as a candidate vector. This strain is attenuated by mutations in its msbB (LPS) and purI (purine biosynthesis pathway) genes and was originally developed as a non-specific 'cancer vaccine' for solid tumors. With a major investment from Vion Inc., YS1646 was carried through pre-clinical and toxicity testing in rodents, dogs and non-human primates before a phase I clinical trial where it ultimately failed [94]. More recently, YS1646 has been used to express a chimeric *Schistosoma japonicum* antigen that was tested in a murine model of schistosomiasis [112]. Repeated oral administration of one of the engineered strains in this study elicited a strong systemic IgG antibody response, induced antigen-specific T cells and provided up to 75% protection against *S. japonicum* challenge.

The present technology, according to various embodiments, consists of known and/or antigens, chimeric proteins, or combinations of proteins, that are expressed, secreted, surface displayed and/or released by bacteria and result in immunologic activity, and may optionally include the combination with secreted protease inhibitors. The bacterial delivery vector may be attenuated, non-pathogenic, low pathogenic (including wild type), or a probiotic bacterium. The bacteria are introduced either systemically (e.g., parentral, intravenous (IV), intramuscular (IM), intralymphatic (IL), intradermal (ID), subcutaneously (sub-q), local-regionally (e.g., intralesionally, intratumorally (IT), intrapaeritoneally (IP), topically, intrathecally (intrathecal), by inhaler or nasal spray) or to the mucosal system through oral, nasal, pulmonary intravessically, enema or suppository administration where they are able to undergo limited replication, express, surface display, secrete and/or release the anti-cancer inhibitory proteins or a combination thereof, and thereby provide a therapeutic or preventive benefit.

Promoters, i.e., genetic regulatory elements that control the expression of the genes encoding the therapeutic molecules described above that are useful in the present technology, according to various embodiments, include constitutive and inducible promoters. A preferred constitutive promoter is that from the vector pTrc99a (Promega). Preferred inducible promoters include the tetracycline inducible promoter (TET promoter), colicin promoters, *sulA* promoters and hypoxic-inducible promoters including but not limited to the PepT promoter (Bermudes et al., WO 01/25397), the arabinose inducible promoter (AraBAD) (Lossner et al., 2007, Cell Microbiol. 9: 1529-1537; WO/2006/048344) the salicylate (aspirin) derivatives inducible promoter (Royo et al., 2007, Nature Methods 4: 937-942; WO/2005/054477), or a quorum-sensing (autoinduction) promoter Anerson et al., 2006 Environmentally controlled invasion of cancer cells by engineered bacteria, J. Mol. Biol. 355: 619-627.

A single promoter may be used to drive the expression of more than one gene, such as an antigen and a protease inhibitor. The genes may be part of a single synthetic operon (polycistronic), or may be separate, monocystronic constructs, with separate individual promoters of the same type used to drive the expression of their respective genes. The promoters may also be of different types, with different genes expressed by different constitutive or inducible promoters. Use of two separate inducible promoters for more than one antigen or other effector type peptide allows, when sufficient tetracycline, arabinose or salicylic acid is administered following administration of the bacterial vector, their expression to occur simultaneously, sequentially, or alternatingly (i.e., repeated). An inducible promoter is not required, and a constitutive promoter may be employed.

The present technology, according to various embodiments, consists of known and/or antigens, chimeric proteins, or combinations of proteins, that are expressed, secreted, surface displayed and/or released by bacteria and result in immunologic activity, and may optionally include the combination with secreted protease inhibitors. The bacterial delivery vector may be attenuated, non-pathogenic, low pathogenic (including wild type), or a probiotic bacterium. The bacteria are introduced either systemically (e.g., parentral, intravenous (IV), intramuscular (IM), intralymphatic (IL), intradermal (ID), subcutaneously (sub-q), local-regionally (e.g., intralesionally, intratumorally (IT), intrapaeritoneally (IP), topically, intrathecally (intrathecal), by inhaler or nasal spray) or to the mucosal system through oral, nasal, pulmonary intravessically, enema or suppository administration where they are able to undergo limited replication, express, surface display, secrete and/or release the anti-cancer inhibitory proteins or a combination thereof, and thereby provide a therapeutic or preventive benefit.

The T3SS secretion system is discussed in U.S. 2019/0055569, 2010/0120124, 2012/0021517, 2015/0359909, U.S. Pat. Nos. 9,951,340, 6,306,387, expressly incorporated herein by reference.

Some bacterial pathogens comprise a type three secretion system (T3SS), which serves as a needle-like system for delivering bacterial polypeptides (effectors) into host cells. These effector polypeptides typically contribute to the virulence of the bacterial cell. In contrast, commensal microbes have not been described to comprise a T3SS.

A T3SS is a multi-protein structure found in gram negative bacteria. It moves polypeptides from the cytoplasm of the bacterial cell through the interior of the T3SS "needle" into the cytoplasm of a target cell. T3SS's are found in pathogenic strains and have been observed in pathogenic isolates of, e.g., Shigella, Salmonella, E. coli, Burkholderia, Yersinia, Chlamydia, Pseudomonas, Erwinia, Ralstonia, Rhizobium, Vibrio, and Xanthamonas. Further discussion of T3SS's can be found, e.g. in Izore et al. Structure 2011 19:603-612; Korotkov et al. Nature Reviews Microbiology 2012 10:336-351; Wooldridge, K. (ed) Bacterial Secreted Proteins. Caster Academic Press 2009; Snyder and Champness (eds.) Molecular Genetics of Bacteria. 3rd Ed. ASM Press: 2007; each of which is incorporated by reference herein in its entirety.

The suite of T3SS-related proteins in a given wild-type cell is typically divided into structural proteins (those proteins which form the needle itself), substrate proteins (those proteins which are transported through the needle to the host), and chaperones (those proteins that bind effectors in the cytoplasm to protect, process, and/or shuttle the effectors to the needle). As used herein, a "functional T3SS" refers, minimally, to the set of structural proteins which are required in order to transfer at least one polypeptide to a target cell. In some embodiments, a functional T3SS system can comprise one or more chaperone proteins. In some embodiments, a functional T3SS can comprise one or more, for example, two, three, or four, substrates which are not virulence factor (e.g. certain translocators). In some embodiments, a functional T3SS does not comprise a virulence factor which is delivered to the target cell.

Bacteriocins are a class of compounds produced by bacteria to control their relationship with other bacteria. Bacteriocins are proteinaceous or peptidic toxins produced by bacteria to inhibit the growth of similar or closely related bacterial strain(s). en.wikipedia.org/wiki/Bacteriocin.

Bacteriocins are categorized in several ways, including producing strain, common resistance mechanisms, and mechanism of killing. There are several large categories of bacteriocin which are only phenomenologically related. These include the bacteriocins from gram-positive bacteria, the colicins, the microcins, and the bacteriocins from Archaea. The bacteriocins from E. coli are called colicins.

Gram negative bacteriocins are typically classified by size. Microcins are less than 20 kDa in size, colicin-like bacteriocins are 20 to 90 kDa in size and tailocins or so called high molecular weight bacteriocins which are multi subunit bacteriocins that resemble the tails of bacteriophages. This size classification also coincides with genetic, structural and functional similarities.

Colicins are bacteriocins (CLBs) found in the Gram-negative E. coli. [113] Similar bacteriocins occur in other Gram-negative bacteria. These CLBs are distinct from Gram-positive bacteriocins. They are modular proteins between 20 and 90 kDa in size. They often consist of a receptor binding domain, a translocation domain and a cytotoxic domain. Combinations of these domains between different CLBs occur frequently in nature and can be created in the laboratory. Due to these combinations further sub-classification can be based on either import mechanism (group A and B) or on cytotoxic mechanism (nucleases, pore forming, M-type, L-type).

A colicin is a type of bacteriocin produced by and toxic to some strains of Escherichia coli. Colicins are released into the environment to reduce competition from other bacterial strains. Colicins bind to outer membrane receptors, using them to translocate to the cytoplasm or cytoplasmic membrane, where they exert their cytotoxic effect, including depolarisation of the cytoplasmic membrane, DNase activity, RNase activity, or inhibition of murein synthesis.

Channel-forming colicins (colicins A, B, E1, Ia, Ib, and N) are transmembrane proteins that depolarize the cytoplasmic membrane, leading to dissipation of cellular energy. These colicins contain at least three domains: an N-terminal translocation domain responsible for movement across the outer membrane and periplasmic space; a central domain responsible for receptor recognition; and a C-terminal cytotoxic domain responsible for channel formation in the cytoplasmic membrane. One domain regulates the target and binds to the receptor on the sensitive cell. The second is involved with translocation, co-opting the machinery of the target cell. The third is the 'killing' domain and may produce a pore in the target cell membrane, or act as a nuclease to chop up the DNA or RNA of the target cell.

Most colicins are able to translocate the outer membrane by a two-receptor system, where one receptor is used for the initial binding and the second for translocation. The initial binding is to cell surface receptors such as the outer membrane proteins OmpF, FepA, BtuB, Cir and FhuA; colicins have been classified according to which receptors they bind to. The presence of specific periplasmic proteins, such as TolA, TolB, TolC, or TonB, are required for translocation across the membrane. Cloacin DF13 is a bacteriocin that inactivates ribosomes by hydrolysing 16S RNA in 30S ribosomes at a specific site.

Because they target specific receptors and use specific translocation machinery, cells can make themselves resistant to the colicin by repressing or deleting the genes for these proteins. Such resistant cells may suffer the lack of a key nutrient (such as iron or a B vitamin), but benefit by not being killed. Pore-forming colicins depolarize the membrane and thus eliminate the energy source for the cell. The colicins are highly effective toxins.

Virtually all colicins are carried on plasmids. The two general classes of colicinogenic plasmids are large, low-copy-number plasmids, and small, high-copy-number plasmids. The larger plasmids carry other genes, as well as the colicin operon. The colicin operons are generally organized with several major genes. These include an immunity gene, a colicin structural gene, and a bacteriocin release protein (BRP), or lysis, gene. The immunity gene is often produced constitutively, while the BRP is generally produced only as a read-through of the stop codon on the colicin structural gene. The colicin itself is repressed by the SOS response and may be regulated in other ways, as well.

Retaining the colicin plasmid is very important for cells that live with their relatives, because if a cell loses the immunity gene, it quickly becomes subject to destruction by circulating colicin. At the same time, colicin is only released from a producing cell by the use of the lysis protein, which results in that cell's death. This suicidal production mechanism would appear to be very costly, except for the fact that it is regulated by the SOS response, which responds to significant DNA damage. In short, colicin production may only occur in terminally ill cells. [114] [115] [116] [117] [118]

As used herein, a "virulence factor" refers to those substrates which affect and/or manipulate a target cell in a manner which is beneficial to infection and deleterious to the target cell, i.e., they perturb the normal function of the target cell. Examples of actions of virulence factors include, but are not limited to, modulation of actin polymerization, induction of apoptosis, modulation of the cell cycle, modulation of gene transcription. Not all substrates are necessarily virulence factors. By way of non-limiting example, a T3SS (and a functional T3SS) can comprise proteins referred to as translocators. These substrates are secreted by the T3SS as it nears a complete form and create a pore in the target cell membrane, allowing further substrates to be delivered into the cytoplasm of the target cell, i.e., translocators are substrates in that they travel through the needle to the target cell and are also structural proteins in that they form part of the structure through which other substrates are delivered into the target cell. In some embodiments, a single polypeptide can be both a translocator and a virulence factor (e.g. IpaB of *Shigella*). A functional T3SS system can be introduced into a non-pathogenic bacterial cell.

Homologs of any given polypeptide or nucleic acid sequence can be found using, e.g., BLAST programs (freely available on the world wide web at blast.ncbi.nlm.nih.gov/), e.g. by searching freely available databases of sequence for homologous sequences, or by querying those databases for annotations indicating a homolog (e.g. search strings that comprise a gene name or describe the activity of a gene). The homologous amino acid or DNA sequence can be at least 90%, at least 95%, at least 96%, at least 97%, at least 98%, at least 99%, or more, identical to a reference sequence. The degree of homology (percent identity) between a reference and a second sequence can be determined, for example, by comparing the two sequences using freely available computer programs commonly employed for this purpose on the world wide web.

Examples of T3SS secretion signals and chaperone-binding domains are known in the art, see, e.g. Schmitz et al. Nat Methods 2009 6:500-2; which described the signals and domains of *Shigella* effectors and which is incorporated by reference herein in its entirety. Additional examples are known in the art, e.g. Sory et al. PNAS 1995 92:11998-20002; which is incorporated by reference herein in its entirety. It is contemplated that a T3SS signal may reduce the activity of the non-T3SS signal portion of the T3SS-compatible polypeptide once it is delivered to the target cell. Accordingly, in some embodiments, the T3SS-compatible polypeptide can comprise a cleavage site after the T3SS signal sequence. In some embodiments, the cleavage site is a site recognized by an endogenous component of the target cell, e.g. a calpain, sumo, and/or furin cleavage site. In some embodiments, instead of a cleavage site, the T3SS-compatible polypeptide can comprise an ubiquitin molecule after the T3SS signal sequence such that the ubiquitin molecule and the sequence N-terminal of it is removed from the remainder of the polypeptide by a eukaryotic target cell. In some embodiments, the first amino acid C-terminal of the ubiquitin molecule can be a methionine.

The T3SS-compatible polypeptide may be an antigen. An engineered microbial cell comprising a T3SS-compatible antigen polypeptide may be to a subject, e.g., orally.

In one aspect, described herein is a kit comprising an engineered microbial cell as described herein. In one aspect, described herein is a kit comprising an engineered microbial cell comprising a first nucleic acid sequence comprising genes encoding a functional type three secretion system (T3SS); and a second nucleic acid sequence encoding an T3SS-compatible polypeptide; wherein the engineered microbial cell is non-pathogenic with respect to a target cell. Citation or identification of any reference herein, in any section of this application, shall not be construed as an admission that such reference is available as prior art to the present application. The disclosures of each reference disclosed herein, whether U.S. or foreign patent literature, or non-patent literature, are hereby incorporated by reference in their entirety in this application, and shall be treated as if the entirety thereof forms a part of this application.

Such references are provided for their disclosure of technologies to enable practice of the present invention, to provide basis for claim language, to make clear applicant's possession of the invention with respect to the various aggregates, combinations, and subcombinations of the respective disclosures or portions thereof (within a particular reference or across multiple references). The citation of references is intended to be part of the disclosure of the invention, and not merely supplementary background information. The incorporation by reference does not extend to teachings which are inconsistent with the invention as expressly described herein, and is evidence of a proper interpretation by persons of ordinary skill in the art of the terms, phrase and concepts discussed herein, without being limiting as the sole interpretation available.

Genetically-engineered bacterial vectors represent a promising method of therapy for various diseases and as a biomolecule delivery system.

Tumor-targeted bacteria, especially those derived from wild type samples, are typically capable of producing a chronic infection without strong acute response. That is, these bacteria seem to have evolved to avoid triggering a debilitating immune response in the host while at the same time establishing long term colonization of tissues, in the case of tumor targeting bacteria, tissues which may include necrotic regions. According to some evolutionary theories, the attenuated host response to these bacteria may result from a survival benefit for the host in permitting the colonization. Indeed, there are at least anecdotal reports of successful eradication of tumors by bacterial therapy. This implies that bacteria derived from these strains can be pharmaceutically acceptable, for administration through various routes of administration.

Much research has been performed on bacterial therapies and bacterial delivery vectors. For example, tumor targeting bacteria offer tremendous potential advantages for the treatment of solid tumors, including the targeting from a distant inoculation site and the ability to express therapeutic agents directly within the tumor (Pawelek et al., 1997, Tumor-targeted *Salmonella* as a novel anticancer agent, Cancer Research 57: 4537-4544; Low et al., 1999, Lipid A mutant *salmonella* with suppressed virulence and TNF-alpha induction retain tumor-targeting in vivo, Nature Biotechnol. 17: 37-41). However, the primary shortcoming of tumor-targeted bacteria investigated in the human clinical trials (*Salmonella* strain VNP20009 also known as YS1646, and its derivative TAPET-CD; Toso et al., 2002, Phase I study of the intravenous administration of attenuated *Salmonella typhimurium* to patients with metastatic melanoma, J. Clin, Oncol. 20: 142-152; Meir et al., 2001, Phase 1 trial of a live, attenuated *Salmonella typhimurium* (VNP20009) administered by direct Intra-tumoral (IT) injection, Proc Am Soc Clin Oncol 20: abstr 1043); Nemunaitis et al., 2003, Pilot trial of genetically modified, attenuated *Salmonella* expressing the *E. coli* cytosine deaminase gene in refractory cancer patients, Cancer Gene Therapy 10: 737-744) is that no significant antitumor activity has been observed, even in patients where the bacteria was documented to target the tumor. One method of increasing the ability of the bacteria to kill tumor cells is to engineer the bacteria to express conventional bacterial toxins (e.g., WO 2009/126189, WO 03/014380, WO/2005/018332, WO/2008/073148, US 2003/0059400 U.S. Pat. Nos. 7,452,531, 7,354,592, 6,962,696, 6,923,972, 6,863,894, 6,685,935, 6,475,482, 6,447,784, 6,190,657 and 6,080,849, 8,241,623, 8,524,220 8,771,669, 8,524,220).

Use of secreted proteins in live bacterial vectors has been demonstrated by several authors. Holland et al. (U.S. Pat. No. 5,143,830) have illustrated the use of fusions with the C-terminal portion of the hemolysin A (hlyA) gene, a member of the type I secretion system. When co-expressed in the presence of the hemolysin protein secretion channel (hlyBD) and a functional TolC, heterologous fusions are readily secreted from the bacteria. The type I secretion system that has been utilized most widely, and although it is currently considered the best system available, is thought to have limitations for delivery by attenuated bacteria (Hahn and Specht, 2003, FEMS Immunology and Medical Microbiology, 37: 87-98). Those limitations include the amount of protein secreted and the ability of the protein fused to it to interfere with secretion. Improvements of the type I secretion system have been demonstrated by Sugamata and Shiba (2005 Applied and Environmental Microbiology 71: 656-662), using a modified hlyB, and by Gupta and Lee (2008 Biotechnology and Bioengineering, 101: 967-974), by addition of rare codons to the hlyA gene. Fusion to the gene ClyA (Galen et al., 2004, Infection and Immunity, 72: 7096-7106 and Type III secretion proteins have also been used. Surface display has been used to export proteins outside of the bacteria. For example, fusion of the Lpp protein amino acids 1-9 with the transmembrane region B3-B7 of OmpA has been used for surface display (Samuelson et al., 2002, Display of proteins on bacteria, J. Biotechnology 96: 129-154). The autotransporter surface display has been described by Berthet et al., WO/2002/070645.

Other heterologous protein secretion systems utilizing the autotransporter family can be modulated to result in either surface display or complete release into the medium (see Henderson et al., 2004, Type V secretion pathway: the autotransporter story, Microbiology and Molecular Biology Reviews 68: 692-744; Jose, 2006 Applied Microbiol. Biotechnol. 69: 607-614; Jose J, Zangen D (2005) Autodisplay of the protease inhibitor aprotinin in *Escherichia coli*. Biochem Biophys Res Commun 333:1218-1226 and Rutherford and Mourez 2006 Microbial Cell Factories 5: 22). For example, Veiga et al. (2003 Journal of Bacteriology 185: 5585-5590 and Klauser et al., 1990 EMBO Journal 9: 1991-1999), demonstrated hybrid proteins containing the b-autotransporter domain of the immunoglobulin A (IgA) protease of Nisseria gonorrhea. Fusions to flagellar proteins have been demonstrated. The peptide, usually of 15 to 36 amino acids in length, is inserted into the central, hypervariable region of the FliC gene such as that from *Salmonella* muenchen (Verma et al. 1995 Vaccine 13: 235-24; Wu et al., 1989 Proc. Natl. Acad. Sci. USA 86: 4726-4730; Cuadro et al., 2004 Infect. Immun. 72: 2810-2816; Newton et al., 1995, Res. Microbiol. 146: 203-216, each of which is expressly incorporated by reference in its entirety). Multi-hybrid FliC insertions of up to 302 amino acids have also been prepared (Tanskanen et al. 2000, Appl. Env. Microbiol. 66: 4152-4156). Trimerization of antigens and functional proteins can be achieved using the T4 fibritin foldon trimerization sequence (Wei et al. 2008 J. Virology 82: 6200-6208) and VASP tetramerization domains (Kühnel et al., 2004 PNAS 101: 17027-17032). The multimerization domains are used to create, bi-specific, tri-specific, and quatra-specific targeting agents, whereby each individual agent is expressed with a multimerization tag, each of which may have the same or separate targeting peptide, such that following expression, surface display, secretion and/or release, they form multimers with multiple targeting domains. Other secretion systems include C-terminal fusions to the protein YebF (Zhang et al., 2006, Extracellular accumulation of recombinant proteins fused to the carrier protein YebF in *Escherichia coli*, Nat Biotechnol 24: 100-104), which is commercially available as a kit (pAES40; AthenaES, Baltimore, Md.). Fusions to OmsY and other proteins are also capable of secreting proteins into the medium (Zian et al., 2008, Proteome-Based Identification of Fusion Partner for High-Level Extracellular Production of Recombinant Proteins in *Escherichia coli*, Biotechnol Bioegineer 101: 587-601). Other secretions systems usable according to the present invention include that of Kotzsch et al. 2011 (A secretory system for bacterial production of high-profile protein targets, Protein Science 20: 597-609) using OmpA, OmpF and OsmY, or those described by Yoon et al., 2010 (Secretory production of recombinant proteins in *Escherichia coli*, Recent Patents on Biotechnology 4: 23-29. See, US2006-7094579, WO2009021548, EP1402036, US2006-7070989, US2008/0193974, US2006-7052867, US2003-6605697, U.S. Pat. No. 5,470,719, US2007/0287171, US2009/0011995, US2008/0076157, US2006-7112434, US2005-6919198, US2002-6455279, US2007-7291325, US2008-7410788, US2000-6083715, EP1270730, US2004-6673569, US2001-6309861, U.S. Pat. No. 5,989,868, US2006-7056732, US2005-6852512, US2005-6861403, EP1407052, WO2008089132, U.S. Pat. No. 5,824,502, EP1068339B1, US2008/0166757, US2001-6329172, US2003-6596509, US2003-6642027, WO2006017929, US2003-6596510, US2008/0280346, US2007-7202059, US2008/0280346, US2007-7202059, US2009-7491528, US2008/0206814, US2008/0166764, US2008/0182295, US2008/0254511, US2008/0206818, US2006-7105327, US2004/0005695, U.S. Pat. No. 5,508,192, EP866132, U.S. Pat. Nos. 6,921,659, 6,828,121, US2008/0064062, EP786009, US2006/0270043, and U.S. Pat. No. 7,202,059.

Compositions described in accordance with various embodiments herein include, without limitation, *Salmonella enterica* serovar *Typhimurium* ("*S. typhimurium*"), *Salmonella* montevideo, *Salmonella enterica* serovar *Typhi* ("*S. typhi*"), *Salmonella enterica* serovar Paratyphi A, Paratyphi B ("*S. paratyphi 13*"), *Salmonella enterica* serovar Paratyphi C ("*S. paratyphi C*"), *Salmonella enterica* serovar Hadar ("*S. hadar*"), *Salmonella enterica* serovar *Enteriditis* ("*S. enteriditis*"), *Salmonella enterica* serovar Kentucky ("*S. kentucky*"), *Salmonella enterica* serovar *Infantis* ("*S. infantis*"), *Salmonella enterica* serovar *Pullorum* ("*S. pullorum*"), *Salmonella enterica* serovar *Gallinarum* ("*S. gallinarum*"), *Salmonella enterica* serovar Muenchen ("*S. muenchen*"), *Salmonella enterica* serovar *Anatum* ("*S. anatum*"), *Salmonella enterica* serovar Dublin ("*S. dublin*"), *Salmonella enterica* serovar Derby ("*S. derby*"), *Salmonella enterica* serovar *Choleraesuis* var. kunzendorf ("*S. cholerae* kunzendorf"), and *Salmonella enterica* serovar minnesota (*S. minnesota*).

By way of example, live bacteria in accordance with aspects of the invention include known strains of *S. enterica* serovar *Typhimurium* (*S. typhimurium*) and *S. enterica* serovar *Typhi* (*S. typhi*) which are further modified as provided by various embodiments of the invention. Such Strains include Ty21a, CMV906, CMV908, CMV906-htr, CMV908-htr, Ty800, aroA-/serC-, holavax, M01ZH09, VNP20009. These strains contain defined mutations within specific serotypes of bacteria. The technology also includes the use of these same (or different) mutational combinations contained within alternate serotypes or strains in order to avoid immune reactions which may occur in subsequent administrations. For example, *S. Typhimurium*, S. montevideo, and *S. typhi* which have non-overlapping O-antigen presentation (e.g., *S. typhimurium* is O-1, 4, 5, 12 and *S. typhi* is Vi, S. montevideo is O-6, 7) may be used. Thus, for example, *S. typhimurium* is a suitable serotype for a first administration and another serotype such as *S. typhi* or S. montevideo are used for a second administration and third administration. Likewise, the flagellar antigens are also selected for non-overlapping antigenicity between different administrations. The flagellar antigen may be H1 or H2 or no flagellar antigen, which, when combined with the three different O-antigen serotypes, provides three completely different antigenic profiles.

Novel strains are also encompassed that are, for example, attenuated in virulence by mutations in a variety of metabolic and structural genes. The invention therefore may provide a live composition for treating cancer comprising a live attenuated bacterium that is a serovar of *Salmonella enterica* comprising an attenuating mutation in a genetic locus of the chromosome of said bacterium that attenuates virulence of said bacterium and wherein said attenuating mutation is the Suwwan deletion (Murray et al., 2004. Hot spot for a large deletion in the 18-19 Cs region confers a multiple phenotype in *Salmonella enterica* serovar *Typhimurium* strain ATCC 14028. Journal of Bacteriology 186: 8516-8523 (2004)) or combinations with other known attenuating mutations. Other attenuating mutation useful in the *Salmonella* bacterial strains described herein may be in a genetic locus selected from the group consisting of phoP, phoQ, edt, cya, crp, poxA, rpoS, htrA, nuoG, pmi, pabA, pts, damA, met, cys, pur, purA, purB, purI, purF, zwf, aroA, aroB, aroC, aroD, serC, gua, cadA, rfc, rjb, rfa, ompR, msbB, leucine and arginine, pfkAB, crr, glk, ptsG, ptsHI, manXYZ and combinations thereof. Strains of *Salmonella* deleted in stn are particularly preferred.

Attenuated gram-positive bacteria are also available as delivery vectors. For example, *Staphylococcus epidermidis*, group B *Streptococcus* including *S. agalaciae*, and *Listeria* species including *L. monocytogenes* may be employed. It is known to those skilled in the art that variations in molecular biology techniques such as use of gram-positive origins of replication, gram-positive signal sequences and gram-positive promoters and filamentous phage (e.g., phage B5; Chopin et al., 2002 J. Bacteriol. 184: 2030-2033, described further below) may be employed and substituted as needed. Other bacterial strains may also be encompassed, including non-pathogenic bacteria of the gut skin (such as *Staphylococcus epidermidis*, Proprionibacteria) and other body locations known as the human microbiome (Grice et al., Topographical and temporal diversity of the human skin microbiome, Science 324: 1190-1192; A framework for human microbiome research; The Human Microbiome Project Consortium, 14 Jun. 2012 Nature 486, 215-221; Spor et al., 2011, Unravelling the effects of the environment and host genotype on the gut microbiome, Nature Reviews Microbiology 9: 279-290) such as *E. coli* strains, Bacteriodies, *Bifidobacterium* and *Bacillus*, attenuated pathogenic strains of *E. coli* including enteropathogenic and uropathogenic isolates, *Enterococcus* sp. and *Serratia* sp. as well as attenuated *Neisseria* sp., *Shigella* sp., *Staphylococcus* sp., *Staphylococcus* carnosis, *Yersinia* sp., *Streptococcus* sp. and *Listeria* sp. including *L. monocytogenes*. Bacteria of low pathogenic potential to humans and other mammals or birds or wild animals, pets and livestock, such as insect pathogenic *Xenorhabdus* sp., *Photorhabdus* sp. and human wound *Photorhabdus* (Xenorhabdus) are also encompassed. Probiotic strains of bacteria are also encompassed, including *Lactobacillus* sp. (e.g., *Lactobacillus acidophilus, Lactobacillus salivarius*) *Lactococcus* sp., (e.g., *Lactococcus lactis, Lactococcus casei*) *Leuconostoc* sp., *Pediococcus* sp., *Streptococcus* sp. (e.g., S. salivariu, *S. thermophilus*), *Bacillus* sp., *Bifidobacterium* sp., *Bacteroides* sp., and *Escherichia coli* such as the 1917 Nissel strain.

It is known to those skilled in the art that minor variations in molecular biology techniques such as use of gram-positive origins of replication, gram-positive signal sequences gram-positive promoters (e.g., *Lactococcus* expression, Mohamadzadeh et al., PNAS Mar. 17, 2009 vol. 106 no. 114331-4336) may be used and substituted as needed. The bacteria may be further modified to be internalized into the host cell (Guimaraes et al., 2006, Use of Native Lactococci as Vehicles for Delivery of DNA into Mammalian Epithelial Cells, Appl Environ Microbiol. 2006 November; 72(11): 7091-7097; Innocentin et al., 2009, *Lactococcus lactis* Expressing either *Staphylococcus aureus* Fibronectin-Binding Protein A or *Listeria monocytogenes* Internalin A Can Efficiently Internalize and Deliver DNA in Human Epithelial Cells Appl Environ Microbiol. 2009 July; 75(14): 4870-4878).

Recently developed approaches to delivery of therapeutic molecules (U.S. Pat. Nos. 8,241,623; 8,524,220; 8,771,669; and 8,524,220) have coupled a protease sensitive therapeutic molecule with co-expression of protease inhibitors, expressly incorporated by reference herein.

The autotransporter surface display has been described by Berthet et al., WO/2002/070645, expressly incorporated by reference herein. Other heterologous protein secretion systems utilizing the autotransporter family can be modulated to result in either surface display or complete release into the medium (see Henderson et al., 2004, Type V secretion pathway: the autotransporter story, Microbiology and Molecular Biology Reviews 68: 692-744; Jose, 2006 Applied Microbiol. Biotechnol. 69: 607-614; Jose J, Zangen D (2005) Autodisplay of the protease inhibitor aprotinin in *Escherichia coli*. Biochem Biophys Res Commun 333:1218-1226 and Rutherford and Mourez 2006 Microbial Cell Factories 5: 22). For example, Veiga et al. (2003 Journal of Bacteriology 185: 5585-5590 and Klauser et al., 1990 EMBO Journal 9: 1991-1999) demonstrated hybrid proteins containing the β-autotransporter domain of the immunoglobulin A (IgA) protease of Nisseria gonorrhea. Fusions to flagellar proteins have been demonstrated. The peptide, usually of 15 to 36 amino acids in length, is inserted into the central, hypervariable region of the FliC gene such as that from *Salmonella* muenchen (Verma et al. 1995 Vaccine 13: 235-24; Wu et al., 1989 Proc. Natl. Acad. Sci. USA 86: 4726-4730; Cuadro et al., 2004 Infect. Immun. 72: 2810-2816; Newton et al., 1995, Res. Microbiol. 146: 203-216, expressly incorporated by reference in their entirety herein).

Multihybrid FliC insertions of up to 302 amino acids have also been prepared (Tanskanen et al. 2000, Appl. Env. Microbiol. 66: 4152-4156, expressly incorporated by reference in its entirety herein).

Trimerization of antigens can be achieved using the T4 fibritin foldon trimerization sequence (Wei et al. 2008 J. Virology 82: 6200-6208) and VASP tetramerization domains (Kühnel et al., 2004 PNAS 101: 17027-17032), expressly incorporated by reference in their entirety herein. The multimerization domains are used to create, bi-specific, tri-specific, and quatra-specific targeting agents, whereby each individual agent is expressed with a multimerization tag, each of which may have the same or separate targeting peptide, such that following expression, surface display, secretion and/or release, they form multimers with multiple targeting domains. A fusion with the *Pseudomonas* ice nucleation protein (INP) wherein the N- and C-terminus of INP with an internal deletion consisting of the first 308 amino acids is followed by the mature sequence of the protein to be displayed (Jung et al., 1998, Surface display of *Zymomonas mobilis* levansucrase by using ice-nucleation protein of *Pseudomonas syringae*, Nature Biotechnology 16: 576-580; Kim et al., 2000, Bacterial surface display of an enzyme library for selective screening of improved cellulase variants, Applied and Environmental Microbiology 66: 788-793; Part:BBa_K811003 from www.iGEM.org; WO2005005630).

*Salmonella* are also encompassed that are, for example, attenuated in virulence by mutations in a variety of metabolic and structural genes. The technology therefore may provide a live composition for treating cancer comprising a live attenuated bacterium that is a serovar of *Salmonella enterica* comprising an attenuating mutation in a genetic locus of the chromosome of said bacterium that attenuates virulence of said bacterium and wherein said attenuating mutation is a combinations of other known attenuating mutations. The strain may also contain a mutation known as "Suwwan", which is an approximately 100 kB deletion between two IS200 elements. The strain may also carry a defective thioredoxin gene (trxA-; which may be used in combination with a TrxA fusion), a defective glutathione oxidoreductase (gor-) and optionally, overexpress a protein disulfide bond isomerase (DsbA). The strain may also be engineered to express invasion and/or escape genes tlyA, tlyC patI and pld from *Rickettsia*, whereby the bacteria exhibit enhanced invasion and/or escape from the phagolysosome (Witworth et al., 2005, Infect. Immun. 73:6668-6673), thereby enhancing the activity of the effector genes described below. The strain may also be engineered to be deleted in an avirulence (anti-virulence) gene, such as zirTS, grvA and/or pcgL, or express the *E. coli* lac repressor, which is also an avirulence gene in order to compensate for over-attenuation. The strain may also express SlyA, a known transcriptional activator. In a preferred embodiment, the *Salmonella* strains are msbB mutants (msbB-). In a more preferred embodiment, the strains are msbB- and Suwwan. In a more preferred embodiment the strains are msbB-, Suwwan and zwf-. Zwf has recently been shown to provide resistance to CO2, acidic pH and osmolarity (Karsten et al., 2009, BMC Microbiology August 18; 9:170). Use of the msbB zwf genetic combination is also particularly preferred for use in combination with administered carbogen (an oxygen carbon dioxide mixture that may enhance delivery of therapeutic agents to a tumor). In a more preferred embodiment, the strains are $msbB^-$, Suwwan, $zwf^-$ and $trxA^-$. In a most preferred embodiment, the strains are $msbB^-$, Suwwan, $zwf^-$, $trxA^-$ and $gor^-$.

The technology also provides, according to one embodiment, a process for preparing genetically stable therapeutic bacterial strains comprising genetically engineering the therapeutic genes of interest into a bacterially codon optimized expression sequence within a bacterial plasmid expression vector, endogenous virulence (VIR) plasmid (of *Salmonella* sp.), or chromosomal localization expression vector for any of the deleted genes or IS200 genes, defective phage or intergenic regions within the strain and further containing engineered restriction endonuclease sites such that the bacterially codon optimized expression gene contains subcomponents which are easily and rapidly exchangeable, and the bacterial strains so produced.

The present technology provides, for example, and without limitation, live bacterial compositions that are genetically engineered to express one or more protease inhibitors combined with antigens.

According to various embodiments, the technology provides pharmaceutical compositions comprising pharmaceutically acceptable carriers and one or more bacterial mutants. The technology also provides pharmaceutical compositions comprising pharmaceutically acceptable carriers and one or more bacterial mutants comprising nucleotide sequences encoding one or more peptides. Preferably, the bacterial mutants are attenuated by introducing one or more mutations in one or more genes in the lipopolysaccharide (LPS) biosynthetic pathway (for gram-negative bacteria), and optionally one or more mutations to auxotrophy for one or more nutrients or metabolites.

In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes. In one embodiment, a pharmaceutical composition comprises a pharmaceutically acceptable carrier and one or more bacterial mutants, wherein said attenuated bacterial mutants are facultative anaerobes or facultative aerobes. In another embodiment, a pharmaceutical composition comprises a pharmaceutically acceptable carrier and one or more attenuated bacterial mutants, wherein said attenuated bacterial mutants are facultative anaerobes or facultative aerobes.

A pharmaceutically effective dosage form may comprise between about $10^5$ to $10^{12}$ live bacteria, within a lyophilized medium for oral administration. In some embodiments, about $10^9$ live bacteria are administered.

Pharmaceutically acceptable formulations may be provided for delivery by other various routes e.g. by intramuscular injection, subcutaneous delivery, by intranasal delivery (e.g. WO 00/47222, U.S. Pat. No. 6,635,246), intradermal delivery (e.g. WO02/074336, WO02/067983, WO02/087494, WO02/0832149 WO04/016281, each of which is expressly incorporated herein by reference it its entirety) by transdermal delivery, by transcutaneous delivery, by topical routes, etc. Injection may involve a needle (including a microneedle), or may be needle-free. See, e.g., U.S. Pat. Nos. 7,452,531, 7,354,592, 6,962,696, 6,923,972, 6,863,894, 6,685,935, 6,475,482, 6,447,784, 6,190,657, 6,080,849 and US Pub. 2003/0059400, each of which is expressly incorporated herein by reference.

Bacterial vector vaccines are known, and similar techniques may be used for the present bacteria as for bacterial vaccine vectors (U.S. Pat. No. 6,500,419, Curtiss, In: New Generation Vaccines: The Molecular Approach, Ed., Marcel Dekker, Inc., New York, N.Y., pages 161-188 and 269-288 (1989); and Mims et al, In: Medical Microbiology, Eds., Mosby-Year Book Europe Ltd., London (1993)). These known vaccines can enter the host, either orally, intranasally or parenterally. Once gaining access to the host, the bacterial vector vaccines express an engineered prokaryotic expression cassette contained therein that encodes a foreign antigen(s). Foreign antigens can be any protein (or part of a protein) or combination thereof from a bacterial, viral, or parasitic pathogen that has vaccine properties (New Generation Vaccines: The Molecular Approach, supra; Vaccines and Immunotherapy, supra; Hilleman, Dev. Biol. Stand., 82:3-20 (1994); Formal et al, Infect. Immun. 34:746-751 (1981); Gonzalez et al, J. Infect. Dis., 169:927-931 (1994); Stevenson et al, FEMS Lett., 28:317-320 (1985); Aggarwal et al, J. Exp. Med., 172:1083-1090 (1990); Hone et al, Microbial. Path., 5:407-418 (1988); Flynn et al, Mol. Microbiol., 4:2111-2118 (1990); Walker et al, Infect. Immun., 60:4260-4268 (1992); Cardenas et al, Vacc., 11:126-135 (1993); Curtiss et al, Dev. Biol. Stand., 82:23-33 (1994); Simonet et al, Infect. Immun., 62:863-867 (1994); Charbit et al, Vacc., 11:1221-1228 (1993); Turner et al, Infect. Immun., 61:5374-5380 (1993); Schodel et al, Infect. Immun., 62:1669-1676 (1994); Schodel et al, J. Immunol., 145:4317-4321 (1990); Stabel et al, Infect. Immun., 59:2941-2947 (1991); Brown, J. Infect. Dis., 155:86-92 (1987); Doggett et al, Infect. Immun., 61:1859-1866 (1993); Brett et al, Immunol., 80:306-312 (1993); Yang et al, J. Immunol., 145:2281-2285 (1990); Gao et al, Infect. Immun., 60:3780-3789 (1992); and Chatfield et al, Bio/Technology, 10:888-892 (1992)). Delivery of the foreign antigen to the host tissue using bacterial vector vaccines results in host immune responses against the foreign antigen, which provide protection against the pathogen from which the foreign antigen originates (Mims, The Pathogenesis of Infectious Disease, Academic Press, London (1987); and New Generation Vaccines: The Molecular Approach, supra). See also: Formal et al, Infect. Immun., 34:746-751 (1981); Wick et al, Infect. Immun., 62:4542-4548 (1994)); Hone et al, Vaccine, 9:810-816 (1991); Tacket et al, Infect. Immun., 60:536-541 (1992); Hone et al, J. Clin. Invest., 90:412-420 (1992); Chatfield et al, Vaccine, 10:8-11 (1992); Tacket et al, Vaccine, 10:443-446 (1992); van Damme et al, Gastroenterol., 103:520-531 (1992) (*Yersinia pestis*), Noriega et al, Infect. Immun., 62:5168-5172 (1994) (*Shigella* spp), Levine et al, In: *Vibrio cholerae*, Molecular to Global Perspectives, Wachsmuth et al, Eds, ASM Press, Washington, D.C., pages 395-414 (1994) (*Vibrio cholerae*), Lagranderie et al, Vaccine, 11:1283-1290 (1993); Flynn, Cell. Molec. Biol., 40(Suppl. 1):31-36 (1994) (*Mycobacterium* strain BCG), Schafer et al, J. Immunol., 149:53-59 (1992)(*Listeria monocytogenes*), each of which is expressly incorporated herein by reference.

The bacteria are generally administered along with a pharmaceutically acceptable carrier and/or diluent. The particular pharmaceutically acceptable carrier and/or diluent employed is not critical to the present invention unless otherwise specific herein (or in a respective incorporated referenced relevant to the issue). Examples of diluents include a phosphate buffered saline, buffer for buffering against gastric acid in the stomach, such as citrate buffer (pH 7.0) containing sucrose, bicarbonate buffer (pH 7.0) alone (Levine et al, J. Clin. Invest., 79:888-902 (1987); and Black et al J. Infect. Dis., 155:1260-1265 (1987), expressly incorporated herein by reference), or bicarbonate buffer (pH 7.0) containing ascorbic acid, lactose, and optionally aspartame (Levine et al, Lancet, II:467-470 (1988), expressly incorporated herein by reference). Examples of carriers include proteins, e.g., as found in skim milk, sugars, e.g., sucrose, or polyvinylpyrrolidone. Typically, these carriers would be used at a concentration of about 0.1-30% (w/v) but preferably at a range of 1-10% (w/v).

Set forth below are other pharmaceutically acceptable carriers or diluents which may be used for delivery specific routes. Any such carrier or diluent can be used for administration of the bacteria of the invention, so long as the bacteria are still capable of invading a target cell. In vitro or in vivo tests for invasiveness can be performed to determine appropriate diluents and carriers. The compositions of the invention can be formulated for a variety of types of administration, including systemic and topical or localized administration. Lyophilized forms are also included, so long as the bacteria are invasive upon contact with a target cell or upon administration to the subject. Techniques and formulations generally may be found in Remington's Pharmaceutical Sciences, Meade Publishing Co., Easton, Pa., expressly incorporated herein by reference in its entirety. For systemic administration, injection is preferred, including intramuscular, intravenous, intraperitoneal, and subcutaneous. For injection, the composition, e.g., bacteria, of the invention can be formulated in liquid solutions, preferably in physiologically compatible buffers such as Hank's solution or Ringer's solution.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives. The preparations may also contain buffer salts, flavoring, coloring and sweetening agents as appropriate.

Preparations for oral administration may be suitably formulated to give controlled release or enteric release. For buccal administration the compositions may take the form of tablets or lozenges formulated in conventional manner.

For administration by inhalation, the pharmaceutical compositions for use according to the present invention are conveniently delivered in the form of an aerosol spray presentation from pressurized packs or a nebulizer, with the use of a suitable propellant, e.g., a hydrofluorocarbon (HFC), carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the composition, e.g., bacteria, and a suitable powder base such as lactose or starch.

The pharmaceutical compositions may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

See also U.S. Pat. No. 6,962,696, expressly incorporated herein by reference in its entirety.

The present invention provides a pharmaceutical composition comprising a pharmaceutically acceptable carrier and an attenuated tumor-targeted bacteria comprising one or more nucleic acid molecules encoding one or more primary effector molecules operably linked to one or more appropriate promoters. The present invention provides a pharmaceutical composition comprising a pharmaceutically acceptable carrier and an attenuated tumor-targeted bacteria comprising one or more nucleic acid molecules encoding one or more primary effector molecules and one or more secondary effector molecules operably linked to one or more appropriate promoters.

The present invention provides a pharmaceutical composition comprising a pharmaceutically acceptable carrier and a bacterium.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil, olive oil, and the like. Saline is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic attenuated tumor-targeted bacteria, in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a suspending agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the pharmaceutical composition of the invention which will be effective in the vaccination of a subject can be determined by standard clinical techniques. In addition, in vitro assays may optionally be employed to help identify optimal dosage ranges. The precise dose to be employed in the formulation will also depend on the route of administration, and should be decided according to the judgment of the practitioner and each patient's circumstances. However, suitable dosage ranges are generally from about 1.0 cfu/kg to about $1\times10^{10}$ cfu/kg; optionally from about 1.0 cfu/kg to about $1\times10^8$ cfu/kg; optionally from about $1\times10^2$ cfu/kg to about $1\times10^8$ cfu/kg; optionally from about 1 $10^4$ cfu/kg to about $1\times10^8$ cfu/kg; and optionally from about $1\times10^4$ cfu/kg to about $1\times10^{10}$ cfu/kg (cfu=colony forming unit). Effective doses may be extrapolated from dose-response curves derived from in vitro or animal model test systems.

Various delivery systems are known and can be used to administer a pharmaceutical composition of the present invention. Methods of introduction include but are not limited to intradermal, intramuscular, intraperitoneal, intravenous, subcutaneous, intranasal, and oral routes. The compositions may be administered by any convenient route, for example by infusion or bolus injection, by absorption through epithelial or mucocutaneous linings (e.g., oral mucosa, rectal and intestinal-mucosa, etc.) and may be administered together with other biologically active agents. Administration can be systemic or local. Pulmonary administration can also be employed, e.g., by use of an inhaler or nebulizer, and formulation with an aerosolizing agent.

The invention also provides a pharmaceutical pack or kit comprising one or more containers filled with one or more of the ingredients of the pharmaceutical compositions of the invention. Optionally associated with such container(s) can be a notice in the form prescribed by governmental agency regulating the manufacture, use or sale of pharmaceuticals or biological products, which notice reflects approval by the agency of manufacture, use or sale for human administration.

The compositions and methods described herein can be administered to a subject in need of treatment, e.g. in need of treatment for inflammation or cancer. In some embodiments, the methods described herein comprise administering an effective amount of compositions described herein, e.g. engineered microbial cells to a subject in order to alleviate a symptom. As used herein, "alleviating a symptom" is ameliorating any condition or symptom associated with a given condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, subcutaneous, transdermal, airway (aerosol), cutaneous, topical, or injection administration. Administration can be local or systemic.

The term "effective amount" as used herein refers to the amount of engineered microbial cells needed to alleviate at least one or more symptom of the disease or disorder, and relates to a sufficient amount of pharmacological composition to provide the desired effect. The term "therapeutically effective amount" therefore refers to an amount of engineered microbial cells that is sufficient to effect a particular effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the $ED_{50}$ (the dose therapeutically effective in 50% of the population). The dosage can vary depending upon the dosage form employed and the route of administration utilized. The dose ratio between toxic and therapeutic effects is the therapeutic index and can be expressed as the ratio $ED_{50}$. Compositions and methods that exhibit large therapeutic indices are preferred. A therapeutically effective dose can be estimated initially from cell culture assays. Also, a dose can be formulated in animal models to achieve a circulating plasma concentration range that includes the $IC_{50}$ (i.e., the concentration of an engineered microbial cell which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for inflammation, among others. The dosage can be determined by a physician and adjusted, as necessary, to suit observed effects of the treatment.

In some embodiments, the technology described herein relates to a pharmaceutical composition comprising an engineered microbial cell as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) glycols, such as propylene glycol; (10) polyols, such as glycerin, sorbitol, mannitol and polyethylene glycol (PEG); (11) esters, such as ethyl oleate and ethyl laurate; (12) agar; (13) buffering agents, such as magnesium hydroxide and aluminum hydroxide; (14) alginic acid; (15) pyrogen-free water; (16) isotonic saline; (17) Ringer's solution; (18) pH buffered solutions; (19) polyesters, polycarbonates and/or polyanhydrides; (20) bulking agents, such as polypeptides and amino acids (21) serum component, such as serum albumin, HDL and LDL; and (22) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Pharmaceutical compositions comprising an engineered microbial cell can be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

In certain embodiments, an effective dose of a composition comprising engineered microbial cells as described herein can be administered to a patient once. In certain embodiments, an effective dose of a composition comprising engineered microbial cells can be administered to a patient repeatedly. In some embodiments, the dose can be a daily administration, for example oral administration, of, e.g., a capsule comprising bacterial cells as described herein. In some embodiments, the dose can be, e.g. an injection or gavage of bacterial cells. In some embodiments, the dose can be administered systemically, e.g. by intravenous injection. In some embodiments, a dose can comprise from $10^6$ to $10^{12}$ cells. In some embodiments, a dose can comprise from about $10^8$ to $10^{10}$ cells. A composition comprising engineered microbial cells can be administered over a period of time, such as over a 5 minute, 10 minute, 15 minute, 20 minute, or 25 minute period. The administration can be repeated, for example, on a regular basis, such as every few days, once a week, or biweekly (i.e., every two weeks) for one month, two months, three months, four months or longer.

In some embodiments, after an initial treatment regimen, the treatments can be administered on a less frequent basis. For example, after treatment biweekly for three months, treatment can be repeated once per month, for six months or a year or longer.

The efficacy of engineered microbial cells in, e.g. the raising of an appropriate immune response to a specified disease, e.g., COVID-19, can be determined by the skilled clinician. However, a treatment is considered "effective treatment," as the term is used herein, clinically useful partial or complete immunity is achieved. Efficacy can be assessed, for example, by measuring a marker, indicator, population statistic, or any other measurable parameter appropriate.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, the terms "reduced", "reduction", "decrease", or "inhibit" can mean a decrease by at least 10% as compared to a reference level, for example a decrease by at least about 20%, or at least about 30%, or at least about 40%, or at least about 50%, or at least about 60%, or at least about 70%, or at least about 80%, or at least about 90% or more or any decrease of at least 10% as compared to a reference level. In some embodiments, the terms can represent a 100% decrease, i.e., a non-detectable level as compared to a reference level. In the context of a marker or symptom, a "decrease" is a statistically significant decrease in such level. The decrease can be, for example, at least 10%, at least 20%, at least 30%, at least 40% or more, and is preferably down to a level accepted as within the range of normal for an individual without such disorder. In some instances, the symptom can be essentially eliminated which means that the symptom is reduced, i.e., the individual is in at least temporary remission.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or non-human animal. Usually the non-human animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Animals also include armadillos, hedgehogs, and camels, top name a few. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, cow, or pig, but is not limited to these examples. Mammals other than humans can be advantageously used as subjects that represent animal models of a given condition. A subject can be male or female.

A subject can be one who has been previously diagnosed with or identified as suffering from or having a condition in need of treatment, and optionally, have already undergone treatment. Alternatively, a subject can also be one who has not been previously diagnosed as having a condition. For example, a subject can be one who exhibits one or more risk factors or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operatively linked to appropriate regulatory sequences. A gene may or may not include regions preceding and following the coding region, e.g. 5' untranslated (5'UTR) or "leader" sequences and 3' UTR or "trailer" sequences.

The term "operatively linked" includes having an appropriate start signal (e.g., ATG) in front of the polynucleotide sequence to be expressed, and maintaining the correct reading frame to permit expression of the polynucleotide sequence under the control of the expression control sequence, and, optionally, production of the desired polypeptide encoded by the polynucleotide sequence. In some examples, transcription of a nucleic acid is under the control of a promoter sequence (or other transcriptional regulatory sequence) which controls the expression of the nucleic acid in a cell-type in which expression is intended. It will also be understood that the nucleic acid can be under the control of transcriptional regulatory sequences which are the same or which are different from those sequences which control transcription of the naturally-occurring form of a protein.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated."

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. cancer or inflammation. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for all purposes, including, but not limited to, describing and disclosing, for example, the methodologies described in such publications that might be used in connection with the technology described herein.

SUMMARY OF THE INVENTION

The recent worldwide outbreak of SARS-CoV-2 has created an urgent need for protective vaccines. Major targets for vaccines against coronaviruses have been previously identified as the capsid, nucleoprotein, and the Spike or S glycoprotein. Among these, the receptor binding domain (RBD) of the spike protein of SARS-CoV plays a particularly important role because it is necessary for viral binding to the protein ACE2 linked to entry into the host. With the goal of eliciting neutralizing antibodies, and because the bat RBD differs from the SARS-CoV-2, and that the entire protein contains immunodominant epitopes that do not include the SARS-CoV-2 RBD, analysis was focused on predicted MHC Class II responses to the RBD itself. Based on these analyses, an attenuated bacterial delivery vector (VNP20009) that has previously been safely administered in human clinical studies, was selected to express secreted, YebF fusions to different portions of the RBD.

The present invention provides a vaccine directed toward the prevention of COVID19 caused by SARS-CoV-2. A DNA construct is provided in a live bacterium, such as *E. coli* Nissel 1917 or attenuated strains of *Salmonella* such as *Salmonella typhimurium* VNP20009. The DNA construct may uniquely represent the receptor binding domain (RBD) of SARS-Cov-2. The live bacterium carrying the DNA construct may be administered orally to a patient or an animal (such as a bat species that could be a host for SARS-CoV-2) in order to induce protective immunity.

A preferred embodiment of the design of the DNA construct is shown in FIG. 1.

Protective immunity through prior exposure is a natural mechanism that limits pandemic spread of emerging pathogens. However, as periodically seen with influenza, immune escape through antigenic drift, or more dramatically, through antigenic shift, allows reemergence of new broadly infective variants over time. These variants are shaped in part by preexisting immunity that limits the more immunologically similar variants and creates an evolutionary opportunity for immunologically dissimilar variants that retain transmissibility.

Severe acute respiratory syndrome (SARS) caused by SARS-CoV coronavirus emerged in 2003 as a new, high mortality respiratory infection. SARS-CoV is believed to have a zoonotic origin, as similar coronaviruses have been found in a number of animal species including bats, which have the highest sequence similarities (Lau et al., 2005; Li et al., 2005).

Antibodies against SARS-CoV S protein have been shown to be neutralizing (Kapada et al., 2005). Previous studies have shown that the spike protein of SARS-CoV induces long-term protective immunity (Du et al., 2007 Vaccine. 2007 Apr. 12; 25(15):2832-8). In that study, the receptor domain was fused with the human IgG1 Fc region. Others have included rhabdovirus-based vectors carrying the SARS-CoV spike protein (Faber et al., 2005), and baculovirus expressed proteins Zhou et al., 2006). Current approaches have recently been summarized (Le et al., 2020). As of that review, there were 78 different projects, most still in the exploratory stage. The mechanisms of immunization and/or antigen delivery include live attenuated viruses, inactivated viruses, non-replicating viral vectors, replicating viral vectors, recombinant proteins, peptide-based antigens, virus-like particles, DNA and RNA. Of the five projects that have moved to the clinic, three include vaccinating against the spike S glycoprotein: an mRNA to the entire 1273 amino acid sequence (Moderna; NCT04283461), an adenovirus type 5 vector (CanSino Biologics; NCT04313127), and a plasmid DNA vector (Inovio Pharmaceuticals; NCT04336410). In that review, the mechanisms of immunization and/or antigen delivery being investigated included live attenuated viruses, inactivated viruses, non-replicating viral vectors, replicating viral vectors, recombinant proteins, peptide-based antigens, virus-like particles, DNA and RNA, while bacterial vectors were not included.

Live attenuated bacterial vectors have been used to generate heterologous vaccines. In a recent study, the *Salmonella* vector VNP20009 (YS1646) that had been developed as a cancer therapeutic (Low et al., 2004) was employed as a delivery vector for an antigen from *Clostridium difficile* (Winter et al., 2019). *Clostridium difficile* is the causative agent for pseudomembranous enterocolitis, an often-fatal disease, yet protection of 82% was achieved with oral immunization and up to 100% using multimodal immunization. Live attenuated bacterial vaccines have many potential advantages, including rapid molecular engineering and rapid production due to cell-free replication competence, and low cost of production.

Alternative approaches to vaccine design continue to be explored. In a recent publication by Grifoni et al. (2020), sequence homology between SARS-CoV and SARS-CoV-2 was used to predict vaccine candidates. Although this approach may generate an immune response, there is only limited evidence that there is any cross protection of SARS-CoV and SARS-CoV-2, and thus the immune response may not be effective. Furthermore, Ou et al. (2020) have now shown that there the antibodies SARS-CoV show limited cross-neutralization of SARS-CoV-2. In addition, there is growing concern that infection by and SARS-CoV-2 does not protect against and SARS-CoV-2 reinfection. It may be that the dominant antibodies produced help with immune clearance, but don't prevent infection because they don't block internalization.

SARS-CoV and SARS-CoV-2 share amino acid sequence homology and therefore a common ancestor, although the closest homology is with bats (Wu 2020, https://doi.org/10.1101/2020.03.04.975995). It therefore seems most likely that SARS-CoV-2 emerged from bats rather than from SARS-CoV. While there are many sequence differences between SARS-CoV-2 and the bat coronavirus, there are a particularly striking number of differences within the receptor binding domain. These differences are likely to contribute to lack of cross-immunity between SARS-CoV and SARS-CoV-2 (Ou et al., 2020), and are also likely to contribute to the cross over to humans and the highly infectious nature of SARS-CoV-2 toward humans, which begins with its interaction with human ACE2 (hACE2). If true, the RBD alteration responsible for host specificity and antigen escape are linked. Three mutant types (V367F, W436R, and D364Y) in the RBD showed higher binding affinity to human ACE2 (Ou et al. Emergence of RBD mutations in circulating SARS-CoV-2 strains enhancing the structural stability and human ACE2 receptor affinity of the spike protein, bioRxiv preprint doi: https://doi.org/10.1101/2020.03.15.991844).

The present approach is guided by the following presumptions:

That and SARS-CoV-2 is derived from the bat coronavirus.

That the mutations in the RBD result in increased human specificity.

That the mutations in the RBD result in immune escape.

That antibodies against the SARS-CoV-2 RBD would have the greatest microneutralization potential.

That the SARS-CoV-2 spike protein contains immunodominant epitopes that may limit the immune response to the RBD.

That immunization with the RBD only removes the immunodominant epitopes and will result in an RBD-directed response.

Thus, immunization against the SARS-CoV-2 RBD would be more effective than the spike protein alone.

That the SARS-CoV-2 RBD can be expressed and secreted by an attenuated bacterial vector as a fusion protein such as with YebF or HlyA.

That the fusion protein is capable of eliciting a neutralizing MHC Class II response.

That an attenuated bacterial vector expressing the SARS-CoV-2 RBD, such as VNP20009 can be safe and effective for administration to humans.

It is therefore an object to provide a live genetically engineered bacterium, comprising a genetically engineered construct comprising a nucleic acid sequence encoding at least one portion of a SARS-CoV-2 antigen, the live genetically engineered bacterium being adapted for administration to a human or animal and colonization of at least one tissue under non-lethal conditions.

It is a further object to provide a genetically engineered bacterium selected from the group consisting of E. coli and Salmonella, comprising: a first genetically engineered construct comprising a nucleic acid sequence encoding at least one portion of a SARS-CoV-2 spike protein receptor binding domain, having an associated promoter; and a second genetically engineered construct comprising a nucleic acid sequence encoding an adjuvant peptide. The at least one portion of a SARS-CoV-2 spike protein receptor binding domain and the adjuvant petide may be together expressed as a fusion petide.

It is a still further object to provide a method of vaccinating a human against SARS-CoV-2, comprising: administering the live genetically engineered bacterium according to claim 1 orally, intranasally, or rectally to the human or animal; allowing the live genetically engineered bacterium to colonize a tissue of the human or animal; and clearing the live genetically engineered bacterium from the human or animal, wherein said administration, colonization, and clearance are non-lethal to the human or animal. The at least one portion of a SARS-CoV-2 antigen may comprise the SARS-Cov-2 spike protein, and the nucleic acid sequence encoding the SARS-CoV-2 spike protein may have an associated promoter.

The at least one portion of a SARS-CoV-2 antigen may comprise the SARS-Cov-2 spike protein.

The nucleic acid sequence encoding the SARS-CoV-2 spike protein may have an associated promoter.

The nucleic acid sequence may further encode a secretion signal.

The live genetically engineered bacterium may be E. coli, e.g., E. coli Nissel 1917, or Salmonella, e.g., Salmonella typhimurium or VNP20009/YS1646.

The at least one portion of the SARS-CoV-2 spike gene portion may be an antigenic subportion of the receptor binding domain.

The at least one portion of the SARS-CoV-2 spike gene portion may be fused in-frame with an adjuvant peptide encoding sequence.

The adjuvant peptide may be a dimer of at least a portion of p28.

The adjuvant peptide may be selected from the group consisting of flagellin, a subportion of flagellin that binds to a toll-like receptor, a combination of p28 and flagellin toll-like receptor binding region, a dimer of C3d p28, and a dimer of C3d p28 with an internal flagellin peptide.

The live genetically engineered bacterium may expresse a gut colonization factor.

The gut colonization factor may be selected from the group consisting of colicin A, E1, E2, E3, E4, E5, E6, E7, E8, E9, DF13, K, N, U, B, D, Ia, and M.

The nucleic acid sequence may further encode at least one of an angiotensin converting enzyme 2 binding peptide and a portion of angiotensin binding protein 2.

The nucleic acid sequence may encode a fusion protein further comprising a portion selected from the group consisting of YebF, ice nucleation protein, autodisplay proteins and HlyA.

The fusion protein may be a truncated portion containing a one or more disulfide bonds or lacking potential for such bonds.

The live genetically engineered bacterium may co-expresse a colicin immunity peptide and a colicin lysis peptide.

The nucleic acid sequence may be integrated with a bacterial chromosome.

The nucleic acid sequence may encode a secretion signal.

The nucleic acid sequence may encode a protease inhibitor, e.g., a serpin or furin inhibitor.

The colonization factor may enhance immunization. The colonization factor may be a colicin co-expressed with its immunity and lysis peptides. The colonization factor may be ColE3.

The bacteria may produce a fusion peptide comprising the antigen and an adjuvant peptide.

BRIEF DESCRIPTION OF THE DRAWINGS

FIG. 1 shows a plasmid vector for expression of SARS-CoV-2 Receptor Binding Domain in E. coli and Salmonella vaccine delivery vectors.

DETAILED DESCRIPTION OF THE PREFERRED EMBODIMENTS

DNA Sequence Analysis of RBD and its Mutations

Recently, a study of the global sequence variation within SARS-CoV-2 has been made available in an interactive format by NextStrain. Their analysis shows eight major strains circulating across the globe, with strong geographic preferences, suggesting the specific mutations they carry represent those of the progenitors for most of the strains in those regions.

The receptor binding domain of SARS-CoV-2, residues 488-525 (hereinafter "SARS-Cov-2 RBD 488-525")"

SEQ ID NO. 015
CYFPLQSYGFQPTNGVGYQPYRVVVLSFELL-HAPATVC

The receptor binding domain of SARS-CoV-2, with 4 added amino acids (CGPK) predicted to be antigenic using the online analysis tool EMBOSS. The additional cysteine may provide for disulfide bonding.

```
                                                   SEQ ID NO. 001
    NITNLCPFGEVFNATRFASVYAWNRKRISNCVADYSVLYNSAS

FSTFKCYGVSPTKLNDLCFTNVYADSFVIRGDEVRQIAPGQTG

KIADYNYKLPDDFTGCVIAWNSNNLDSKVGGNYNYLYRLFRKS

NLKPFERDISTEIYQAGSTPCNGVEGFNCYFPLQSYGFQPTNG

VGYQPYRVVVLSFELLHAPATVCGPK
```

A graphical representation of the modified portion of the circular plasmid pTrc99a (Genbank U13872.1). The lacI (repressor) has been partially deleted. Various portions of the receptor binding domain RBD of SARS-CoV-2 (Wuhan-Hu-1 NC_045512.2), e.g., 488-525, preceded by a flexible linker, are expressed under control of the ptrc promoter with an RBS as an in-frame fusion with YebF e.g., [128], followed by a stop codon. Receptor binding domain may include the cysteines for possible disulfide bonding. Optionally, and adjuvant peptide such as C3d-P28208-235 (SEQ ID NO. 004; [124]), or flagellin peptides (e.g., those of domains aD1a, aD1b, aD1C, [119]), may be inserted singly or at both sites to create repeats. A colonization enhancing factor, colicin E3 (E3) and its immunity factor (E3 immune) from Genbank KM287568 are optionally co-expressed.

Flexible linker with RBD 488-525
SEQ ID NO. 002
GGGGScyfplqsygfqptngvgygpyrvvvlsfellhapatvc FIG. 1 shows plasmid vector for expression of SARS-CoV-2 Receptor Binding Domain in *E. coli* and *Salmonella* vaccine delivery vectors. A graphical representation of the modified portion of the circular plasmid pTrc99a (Genbank U13872.1). The lacI (repressor) has been partially deleted. Various portions of the receptor binding domain RBD of SARS-CoV-2 (Wuhan-Hu-1 NC_045512.2), e.g., 488-525, preceded by a flexible linker, are expressed under control of the ptrc promoter with an RBS as an in-frame fusion with YebF (e.g., [128]), followed by a stop codon. Receptor binding domain may include the cysteines for possible disulfide bonding. Optionally, and adjuvant peptide such as C3d-P28$_{208-235}$. The flexible linker with RBD 488-528 may be, for example, SEQ ID NO. 003
GGGGScyfplqsygfqptngvgygpyrvvvlsfellhapatvcGPK
SEQ ID NO. 004
KFLTTAKDKNRWEDPGKQLYNVEATSYA a synthetic peptide corresponding to the CR2-binding site on C3d, P28 [124] or flagellin peptides (e.g., those of domains aD1a, aD1b, aD1C, [119]), may be inserted singly or at both sites to create repeats. A colonization enhancing factor, colicin E3 (E3) and its immunity factor (E3 immune) from Genbank KM287568 are optionally co-expressed.

Example 1

A yebF fusion with 41 amino acids of the RBD, expressed by an attenuated *Salmonella* VNP20009.

An expression plasmid, pTrc99a, with a YebF, containing an in-frame fusion with a portion of the RBD consisting of 41 amino acids, from a cysteine to a cysteine with added GPK and an added artificial lysine followed by a stop codon.

SEQ ID NO. 005
```
atggctaaaaaaagagggcgttttagggctgttgttggtttc
tgcctgcgcatcagtttcgctgccaataatgaaaccagcaagt
cggtcactttcccaaagtgtgaagatctggatgctgccggaatt
gccgcgagcgtaaaacgtgattatcaacaaatcgcgtggcgcg
ttgggcagatgatcaaaaaattgtcggtcaggccgatcccgtgg
cttgggtcagtttgcaggacattcagggtaaagatgataaatgg
tcagtaccgctaaccgtgcgtggtaaaagtgccgatattcatta
ccaggtcagcgtggactgcaaagcgggaatggcggaatatcagc
ggcgtctcgagGGTactagtGGCGGTGGTGGCAGTtgcTATTTT
CCACTGCAGTGTTATGGCTTTCAGCCGACTAACGGTGTGGGTTA
CCAACCGTACCGTGTGGTTGTACTGTCTTTCGAGCTGCTGCATG
CCCCGGCAACCGTATGCGgCCCGAAGAAATCTga
```

An example of a complete pTrc99a plasmid, with the YebF 41aa of RBD, and the ColE3 colicin, immunity and lysis protein:

SEQ ID NO. 006
```
GTTTGACAGCTTATCATCGACTGCACGGTGCACCAATGCTTCTGGCGTCAGGCAGC
CATCGGAAGCTGTGGTATGGCTGTGCAGGTCGTAAATCACTGCATAATTCGTGTCGCT
CAAGGCGCACTCCCGTTCTGGATAATGTTTTTTGCGCCGACATCATAACGGTTCTGGC
AAATATTCTGAAATGAGCTGTTGACAATTAATCATCCGGCTCGTATAATGTGTGGAAT
TGTGAGCGGATAACAATTTCACACAGGAAACAGACCatggctaaaaaagagggcgt
ttttagggctgttgttggtttctgcctgcgcatcagttttcgctgccaataatgaaac
cagcaagtcggtcactttcccaaagtgtgaagatctggatgctgccggaattgccgcg
agcgtaaaacgtgattatcaacaaatcgcgtggcgcgttgggcagatgatcaaaaaa
ttgtcggtcaggccgatcccgtggcttgggtcagtttgcaggacattcagggtaaaga
tgataaatggtcagtaccgctaaccgtgcgtggtaaaagtgccgatattcattaccag
gtcagcgtggactgcaaagcgggaatggcggaatatcagcggcgtctcgagGGTacta
gtGGCGGTGGTGGCAGTtgcTATTTTCCACTGCAGTCTTATGGCTTTCAGCCGACTAA
CGGTGTGGGTTACCAACCGTACCGTGTGGTTGTACTGTCTTTCGAGCTGCTGCATGCC
CCGGCAACCGTATGCGgCCCGAAGAAATCTgaTCTAGAGTCGACCTGCAGGCATGCA
AGCTTGGCTGTTTTGGCGGATGAGAGAAGATTTTCAGCCTGATACAGATTAAATCAGA
ACGCAGAAGCGGTCTGATAAAACAGAATTTGCCTGGCGGCAGTAGCGCGGTGGTCCCA
CCTGACCCCATGCCGAACTCAGAAGTGAAACGCCGTAGCGCCGATGGTAGTGTGGGGT
CTCCCCATGCGAGAGTAGGGAACTGCCAGGCATCAAATAAAACGAAAGGCTCAGTCGA
```

-continued

AAGACTGGGCCTTTCGTTTTATCTGTTGTTTGTCGGTGAACGCTCTCCTGAGTAGGAC

AAATCCGCCGGGAGCGGATTTGAACGTTGCGAAGCAACGGCCCGGAGGGTGGCGGGCA

GGACGCCCGCCATAAACTGCCAGGCATCAAATTAAGCAGAAGGCCATCCTGACGGATG

GCCTTTTTGCGTTTCTACAAACTCTTTTTGTTTATTTTTCTAAATACATTCAAATATG

TATCCGCTCATGAGACAATAACCCTGATAAATGCTTCAATAATATTGAAAAAGGAAGA

GTATGAGTATTCAACATTTCCGTGTCGCCCTTATTCCCTTTTTTGCGGCATTTTGCCT

TCCTGTTTTTGCTCACCCAGAAACGCTGGTGAAAGTAAAAGATGCTGAAGATCAGTTG

GGTGCACGAGTGGGTTACATCGAACTGGATCTCAACAGCGGTAAGATCCTTGAGAGTT

TTCGCCCCGAAGAACGTTTTCCAATGATGAGCACTTTTAAAGTTCTGCTATGTGGCGC

GGTATTATCCCGTGTTGACGCCGGGCAAGAGCAACTCGGTCGCCGCATACACTATTCT

CAGAATGACTTGGTTGAGTACTCACCAGTCACAGAAAAGCATCTTACGGATGGCATGA

CAGTAAGAGAATTATGCAGTGCTGCCATAACCATGAGTGATAACACTGCGGCCAACTT

ACTTCTGACAACGATCGGAGGACCGAAGGAGCTAACCGCTTTTTTGCACAACATGGGG

GATCATGTAACTCGCCTTGATCGTTGGGAACCGGAGCTGAATGAAGCCATACCAAACG

ACGAGCGTGACACCACGATGCCTACAGCAATGGCAACAACGTTGCGCAAACTATTAAC

TGGCGAACTACTTACTCTAGCTTCCCGGCAACAATTAATAGACTGGATGGAGGCGGAT

AAAGTTGCAGGACCACTTCTGCGCTCGGCCCTTCCGGCTGGCTGGTTTATTGCTGATA

AATCTGGAGCCGGTGAGCGTGGGTCTCGCGGTATCATTGCAGCACTGGGGCCAGATGG

TAAGCCCTCCCGTATCGTAGTTATCTACACGACGGGGAGTCAGGCAACTATGGATGAA

CGAAATAGACAGATCGCTGAGATAGGTGCCTCACTGATTAAGCATTGGTAACTGTCAG

ACCAAGTTTACTCATATATACTTTAGATTGATTTAAAACTTCATTTTTAATTTAAAAG

GATCTAGGTGAAGATCCTTTTTGATAATCTCATGACCAAAATCCCTTAACGTGAGTTT

TCGTTCCACTGAGCGTCAGACCCCGTAGAAAAGATCAAAGGATCTTCTTGAGATCCTT

TTTTTCTGCGCGTAATCTGCTGCTTGCAAACAAAAAAACCACCGCTACCAGCGGTGGT

TTGTTTGCCGGATCAAGAGCTACCAACTCTTTTTCCGAAGGTAACTGGCTTCAGCAGA

GCGCAGATACCAAATACTGTCCTTCTAGTGTAGCCGTAGTTAGGCCACCACTTCAAGA

ACTCTGTAGCACCGCCTACATACCTCGCTCTGCTAATCCTGTTACCAGTGGCTGCTGC

CAGTGGCGATAAGTCGTGTCTTACCGGGTTGGACTCAAGACGATAGTTACCGGATAAG

GCGCAGCGGTCGGGCTGAACGGGGGGTTCGTGCACACAGCCCAGCTTGGAGCGAACGA

CCTACACCGAACTGAGATACCTACAGCGTGAGCTATGAGAAAGCGCCACGCTTCCCGA

AGGGAGAAAGGCGGACAGGTATCCGGTAAGCGGCAGGGTCGGAACAGGAGAGCGCACG

AGGGAGCTTCCAGGGGGAAACGCCTGGTATCTTTATAGTCCTGTCGGGTTTCGCCACC

TCTGACTTGAGCGTCGATTTTTGTGATGCTCGTCAGGGGGCGGAGCCTATGGAAAAA

CGCCAGCAACGCGGCCTTTTTACGGTTCCTGGCCTTTTGCTGGCCTTTTGCTCACATG

TTCTTTCCTGCGTTATCCCCTGATTCTGTGGATAACCGTATTACCGCCTTTGAGTGAG

CTGATACCGCTCGCCGCAGCCGAACGACCGAGCGCAGCGAGTCAGTGAGCGAGGAAGC

GGAAGAGCGCCTGATGCGGTATTTTCTCCTTACGCATCTGTGCGGTATTTCACACCGc atatgcccgctctgcgttttctaagtgttatccctcctgatttctaaaaaattttcca cctgaacTTGACagaaaaaacgatgacgagtactttttgatctgtacataaacccagt ggttttatgtacagtatta atcgtgtaatcaattgttttaaCgCttaaaagagggaat -continued ttttatgagcggtggcgatggacgcggccataacacgggcgcgcatagcacaagtggt aacattaatggtggcccgaccgggcttggtgtaggtggtggtgcttctgatggctccg gatggagttcggaaaataacccgtggggtggtggttccggtagcggcattcactgggg tggtggttccggtcatggtaatggcggggggaatggtaattccggtggtggttcggga acaggcggtaatctgtcagcagtagctgcgccagtggcatttggttttccggcacttt ccactccaggagctggcggtctggcggtcagtatttcagcgggagcattatcggcagc tattgctgatattatggctgccctgaaaggaccgtttaaatttggtctttgggggtg gctttatatggtgtattgccatcacaaatagcgaaagatgaccccaatatgatgtcaa agattgtgacgtcattacccgcagatgatattactgaatcacctgtcagttcattacc tctcgataaggcaacagtaaacgtaaatgttcgtgttgttgatgatgtaaaagacgag cgacagaatatttcggttgtttcaggtgttccgatgagtgttccggtggttgatgcaa aacctaccgaacgtccgggtgtttttacggcatcaattccaggtgcacctgttctgaa tatttcagttaataacagtacgccagcagtacagacattaagcccaggtgttacaaat aatactgataaggatgttcgcccggcaggatttactcagggtggtaataccagggatg cagttattcgattcccgaaggacagcggtcataatgccgtatatgtttcagtgagtga tgttcttagccctgaccaggtaaaacaacgtcaagatgaagaaaatcgccgtcagcag gaatgggatgctacgcatccggttgaagcggctgagcgaaattatgaacgcgcgcgtg cagagctgaatcaggcaaatgaagatgttgccagaaatcaggagcgacaggctaaagc tgttcaggtttataattcgcgtaaaagcgaacttgatgcagcgaataaaactcttgct gatgcaatagctgaaataaaacaatttaatcgatttgcccatgacccaatggctggcg gtcacagaatgtggcaaatggccgggcttaaagcccagcgggcgcagacggatgtaaa taataagcaggctgcatttgatgctgctgcaaaagagaagtcagatgctgatgctgca ttgagttctgctatggaaagcaggaagaagaaagaagataagaaaaggagtgctgaaa ataatttaaacgatgaaaagaataagcccagaaaaggttttaaagattacgggcatga ttatcatccagctccgaaaactgagaatattaaagggcttggtgatcttaagcctggg ataccaaaaacaccaaagcagaatggtggtggaaaacgcaagcgctggactggagata aagggcgtaagatttatgagtgggattctcagcatggtgagcttgaggggtatcgtgc cagtgatggtcagcatcttggctcatttgaccctaaaacaggcaatcagttgaaaggt ccagatccgaaacgaaatatcaagaaatatctttgagaggaagttatgggacttaaat tggatttaacttggtttgataaaagtacagaagattttaagggtgaggagtattcaaa agattttggagatgacggttcagttatggaaagtctaggtgtgccttttaaggataat gttaataacggttgctttgatgttatagctgaatgggtacctttgctacaaccatact ttaatcatcaaattgatatttccgataatgagtattttgtttcgtttgatt<ins>atcgTGA</ins>
<ins>TGGTGATTGG</ins>TGAtcaaatattatcagggatgagttgatatacgggcttctagtgttc atggatgaacgctggagcctccaaatgtagaaatgttatatttttttattgagttcttg gttataattgctccgcaatgatttaaataagcattatttaaaacattctcaggagagg tgaaggtggagctaaaaaaagtattggtgattacactgaaaccgaattcaaaaaatt tattgaagacatcatcaattgtgaaggtgatgaaaaaaacaggatgataacctcgag tattttataaatgttactgagcatcctagtggttctgatctgatttattacccagaag gtaataatgatggtagccctgaaggtgttattaaagagattaaagaatggcgagccgc taacggtaagtcaggatttaaacagggctgaaatatgaatgccggttgtttatggatg -continued

```
aatggctggcattctttcacaacaaggagtcgttatgaaaaaataacagggattatt ttattgcttcttgcagtcattattctgtctgcatgtcaggcaaactatatccgggatg ttcagggcgggaccgtatctccgtcatcaacagctgaagtgaccggattagcaacgca gtaacccgaaatcctctttgacaaaaacaaagcgtgtcaggctGCGGCCGCCCATTGC

TGTGGAAGCTGCCTGCACTAATGTTCCGGCGTTATTTCTTGATGTCTCTGACCAGACA

CCCATCAACAGTATTATTTTCTCCCATGAAGACGGTACGCGACTGGGCGTGGAGCATC

TGGTCGCATTGGGTCACCAGCAAATCGCGCTGTTAGCGGGCCCATTAAGTTCTGTCTC

GGCGCGTCTGCGTCTGGCTGGCTGGCATAAATATCTCACTCGCAATCAAATTCAGCCG

ATAGCGGAACGGGAAGGCGACTGGAGTGCCATGTCCGGTTTTCAACAAACCATGCAAA

TGCTGAATGAGGGCATCGTTCCCACTGCGATGCTGGTTGCCAACGATCAGATGGCGCT

GGGCGCAATGCGCGCCATTACCGAGTCCGGCTGCGCGTTGGTGCGGATATCTCGGTA

GTGGGATACGACGATACCGAAGACAGCTCATGTTATATCCCGCCGTTAACCACCATCA

AACAGGATTTTCGCCTGCTGGGGCAAACCAGCGTGGACCGCTTGCTGCAACTCTCTCA

GGGCCAGGCGGTGAAGGGCAATCAGCTGTTGCCCGTCTCACTGGTGAAAAGAAAAACC

ACCCTGGCGCCCAATACGCAAACCGCCTCTCCCCGCGCGTTGGCCGATTCATTAATGC

AGCTGGCACGACAGGTTTCCCGACTGGAAAGCGGGCAGTGAGCGCAACGCAATTAATG

TGAGTTAGCGCGAATTGATCTG
```

The plasmid may further consist of an adjuvant peptide cloned in-frame into the XhoI and SpeI sites, such as the P28 peptide [122][123], SEQ ID NO 004, or a truncated p28 peptide. [124]

SEQ ID NO. 007
GKQLYNVEATSYA

An example of an alternative peptide adjuvant is a peptide, artificial sequence, containing P28 dimer, separated by a portion of the *Vibrio vulnificus* flagellin with flexible linkers. [119][125][126]

SEQ ID NO. 008
KFLTTAKDKNRWEDPGKQLYNVEATSYAGGGGSGGGGSGGGGSaqt
aegamnettnilqrmrdislqsangsnskservaiqeeitalndel
nGGGGSGGGGSGGGGSKFLTTAKDKNRWEDPGKQLYNVEATSYA Example 2

Colicin E3-CA38 Genbank KM287568. [127]
Colicin E3, E3, E8 immunity

SEQ ID NO. 009
```
catatgcccgctctgcgttttctaagtgttatccctcctgatttctaaaaaattttccac ctgaacTTGACagaaaaaacgatgacgagtacttttgatctgtacataaacccagtggt tttatgtacagtattaatcgtgtaatcaattgttttaacgcttaaaagagggaattttat gagcggtggcgatggacgcggccataacacgggcgcgcatagcacaagtggtaacatta atggtggcccgaccgggcttggtgtaggtggtggtgcttctgatggctccggatggagtt cggaaaataacccgtggggtggtggttccggtagcggcattcactggggtggtggttccg gtcatggtaatggcggggggaatggtaattccggtggtggttcgggaacaggcggtaatc tgtcagcagtagctgcgccagtggcatttggttttccggcactttccactccaggagctg gcggtctggcggtcagtatttcagcgggagcattatcggcagctattgctgatattatgg ctgccctgaaaggaccgtttaaatttggtctttgggggtggctttatatggtgtattgc catcacaaatagcgaaagatgacccaatatgatgtcaaagattgtgacgtcattacccg cagatgatattactgaatcacctgtcagttcattacctctcgataaggcaacagtaaacg taaatgttcgtgttgttgatgatgtaaaagacgagcgacagaatatttcggttgtttcag gtgttccgatgagtgttccggtggttgatgcaaaacctaccgaacgtccgggtgtttttac
```

-continued

```
ggcatcaattccaggtgcacctgttctgaatatttcagttaataacagtacgccagcag tacagacattaagcccaggtgttacaaataatactgataaggatgttcgcccggcaggat ttactcagggtggtaataccagggatgcagttattcgattcccgaaggacagcggtcata atgccgtatatgtttcagtgagtgatgttcttagccctgaccaggtaaaacaacgtcaag atgaagaaaatcgccgtcagcaggaatgggatgctacgcatccggttgaagcggctgagc gaaattatgaacgcgcgcgtgcagagctgaatcaggcaaatgaagatgttgccagaaatc aggagcgacaggctaaagctgttcaggtttataattcgcgtaaaagcgaacttgatgcag cgaataaaactcttgctgatgcaatagctgaaataaaacaatttaatcgatttgcccatg acccaatggctggcggtcacagaatgtggcaaatggccgggcttaaagcccagcgggcgc agacggatgtaaataataagcaggctgcatttgatgctgctgcaaaagagaagtcagatg ctgatgctgcattgagttctgctatggaaagcaggaagaagaaagaagataagaaaagga gtgctgaaaataatttaaacgatgaaaagaataagcccagaaaaggttttaaagattacg ggcatgattatcatccagctccgaaaactgagaatattaaagggcttggtgatcttaagc ctgggataccaaaaacaccaaagcagaatggtggtggaaaacgcaagcgctggactggag ataaagggcgtaagatttatgagtgggattctcagcatggtgagcttgaggggtatcgtg ccagtgatggtcagcatcttggctcatttgaccctaaaacaggcaatcagttgaaaggtc cagatccgaaacgaaatatcaagaaatatctttgagaggaagtATGGGACTTAAATTGG

ATTTAACTTGGTTTGATAAAAGTACAGAAGATTTTAAGGGTGAGGAGTATTCAAAAGATT

TTGGAGATGACGGTTCAGTTATGGAAAGTCTAGGTGTGCCTTTTAAGGATAATGTTAATA

ACGGTTGCTTTGATGTTATAGCTGAATGGGTACCTTTGCTACAACCATACTTTAATCATC

AAATTGATATTTCCGATAATGAGTATTTTGTTTCGTTTGATTATCGTGATGGTGATTGGT

GAGCGGCCGCCCATTGCTGTGG
```

Colicin E3, E3, E8 immunity+lysis

```
                                                      SEQ ID NO. 009
cccgctctgcgttttctaagtgttatccctcctgatttctaaaaaattttccacctgaac TTGACagaaaaaacgatgacgagtacttttgatctgtacataaacccagtggttttatg tacagtattaatcgtgtaatcaattgttttaacgcttaaaagagggaattttttatgagcg gtggcgatggacgcggccataacacgggcgcgcatagcacaagtggtaacattaatggtg gcccgaccgggcttggtgtaggtggtggtgcttctgatggctccggatggagttcggaaa ataacccgtggggtggtggttccggtagcggcattcactggggtggtggttccggtcatg gtaatggcgggggaatggtaattccggtggtggttcgggaacaggcggtaatctgtcag cagtagctgcgccagtggcatttggttttccggcacttccactccaggagctggcggtc tggcggtcagtatttcagcgggagcattatcggcagctattgctgatattatggctgccc tgaaaggaccgtttaaatttggtctttgggggtggctttatatggtgtattgccatcac aaatagcgaaagatgaccccaatatgatgtcaaagattgtgacgtcattacccgcagatg atattactgaatcacctgtcagttcattacctctcgataaggcaacagtaaacgtaaatg ttcgtgttgttgatgatgtaaaagacgagcgacagaatatttcggttgtttcaggtgttc cgatgagtgttccggtggttgatgcaaaacctaccgaacgtccgggtgttttttacggcat caattccaggtgcacctgttctgaatatttcagttaataacagtacgccagcagtacaga cattaagcccaggtgttacaaataatactgataaggatgttcgcccggcaggatttactc
```

-continued

```
agggtggtaataccagggatgcagttattcgattcccgaaggacagcggtcataatgccg
tatatgtttcagtgagtgatgttcttagccctgaccaggtaaaacaacgtcaagatgaag
aaaatcgccgtcagcaggaatgggatgctacgcatccggttgaagcggctgagcgaaatt
atgaacgcgcgcgtgcagagctgaatcaggcaaatgaagatgttgccagaaatcaggagc
gacaggctaaagctgttcaggtttataattcgcgtaaaagcgaacttgatgcagcgaata
aaactcttgctgatgcaatagctgaaataaaacaatttaatcgatttgcccatgacccaa
tggctggcggtcacagaatgtggcaaatggccgggcttaaagcccagcgggcgcagacgg
atgtaaataataagcaggctgcatttgatgctgctgcaaaagagaagtcagatgctgatg
ctgcattgagttctgctatggaaagcaggaagaagaaagaagataagaaaaggagtgctg
aaaataatttaaacgatgaaaagaataagcccagaaaaggttttaaagattacgggcatg
attatcatccagctccgaaaactgagaatattaaagggcttggtgatcttaagcctggga
taccaaaaacaccaaagcagaatggtggtggaaaacgcaagcgctggactggagataaag
ggcgtaagatttatgagtgggattctcagcatggtgagcttgaggggtatcgtgccagtg
atggtcagcatcttggctcatttgaccctaaaacaggcaatcagttgaaaggtccagatc
cgaaacgaaatatcaagaaatatctttgagaggaagttatgggacttaaattggatttaa
cttggtttgataaaagtacagaagattttaagggtgaggagtattcaaaagattttggag
atgacggttcagttatggaaagtctaggtgtgccttttaaggataatgttaataacggtt
gctttgatgttatagctgaatgggtacccttgctacaaccatactttaatcatcaaattg
atatttccgataatgagtattttgtttcgtttgattatcgTGATGGTGATTGGTGAtcaa
atattatcagggatgagttgatatacgggcttctagtgttcatggatgaacgctggagcc
tccaaatgtagaaatgttatatttttattgagttcttggttataattgctccgcaatga
tttaaataagcattatttaaaacattctcaggagaggtgaaggtggagctaaaaaaagt
attggtgattacactgaaaccgaattcaaaaaatttattgaagacatcatcaattgtgaa
ggtgatgaaaaaaacaggatgataacctcgagtattttataaatgttactgagcatcct
agtggttctgatctgatttattacccagaaggtaataatgatggtagccctgaaggtgtt
attaaagagattaaagaatggcgagccgctaacggtaagtcaggatttaaacagggctga
aatatgaatgccggttgtttatggatgaatggctggcattctttcacaacaaggagtcgt
tatgaaaaaataacagggattattttattgcttcttgcagtcattattctgtctgcatg
tcaggcaaactatatccgggatgttcagggcgggaccgtatctccgtcatcaacagctga
agtgaccggattagcaacgcagtaacccgaaatcctctttgacaaaaacaaagcgtgtca
ggct
```

Wuhan seafood market pneumonia virus isolate Wuhan-Hu-1, complete genome
NCBI Reference Sequence: NC_045512.2 IDC-27DNA

SEQ ID NO. 010

MFVFLVLLPLVSSQCVNLTTRTQLPPAYTNSFTRGVYYPDKVFRSSVLH

STQDLFLPFFSNVTWFHAIHVSGTNGTKRFDNPVLPFNDGVYFASTEKS

NIIRGWIFGTTLDSKTQSLLIVNNATNVVIKVCEFQFCNDPFLGVYYHK

NNKSWMESEFRVYSSANNCTFEYVSQPFLMDLEGKQGNFKNLREFVFKN

IDGYFKIYSKHTPINLVRDLPQGFSALEPLVDLPIGINITRFQTLLALH

RSYLTPGDSSSGWTAGAAAYYVGYLQPRTFLLKYNENGTITDAVDCALD

PLSETKCTLKSFTVEKGIYQTSNFRVQPTESIVRFPNITNLCPFGEVFN

ATRFASVYAWNRKRISNCVADYSVLYNSASFSTFKCYGVSPTKLNDLCF

TNVYADSFVIRGDEVRQIAPGQTGKIADYNYKLPDDFTGCVIAWNSNNL

DSKVGGNYNYLYRLFRKSNLKPFERDISTEIYQAGSTPCNGVEGFNCYF

PLQSYGFQPTNGVGYQPYRVVVLSFELLHAPATVCGPKKSTNLVKNKCV

NFNFNGLTGTGVLTESNKKFLPFQQFGRDIADTTDAVRDPQTLEILDIT

PCSFGGVSVITPGTNTSNQVAVLYQDVNCTEVPVAIHADQLTPTWRVYS

TGSNVFQTRAGCLIGAEHVNNSYECDIPIGAGICASYQTQTNSPRRARS

-continued

VASQSIIAYTMSLGAENSVAYSNNSIAIPTNFTISVTTEILPVSMTKTS

VDCTMYICGDSTECSNLLLQYGSFCTQLNRALTGIAVEQDKNTQEVFAQ

VKQIYKTPPIKDFGGFNFSQILPDPSKPSKRSFIEDLLFNKVTLADAGF

IKQYGDCLGDIAARDLICAQKFNGLTVLPPLLTDEMIAQYTSALLAGTI

TSGWTFGAGAALQIPFAMQMAYRFNGIGVTQNVLYENQKLIANQFNSAI

GKIQDSLSSTASALGKLQDVVNQNAQALNTLVKQLSSNFGAISSVLNDI

LSRLDKVEAEVQIDRLITGRLQSLQTYVTQQLIRAAEIRASANLAATKM

SECVLGQSKRVDFCGKGYHLMSFPQSAPHGVVFLHVTYVPAQEKNFTTA

PAICHDGKAHFPREGVFVSNGTHWFVTQRNFYEPQIITTDNTFVSGNCD

VVIGIVNNTVYDPLQPELDSFKEELDKYFKNHTSPDVDLGDISGINASV

VNIQKEIDRLNEVAKNLNESLIDLQELGKYEQYIKWPWYIWLGFIAGLI

AIVMVTIMLCCMTSCCSCLKGCCSCGSCCKFDEDDSEPVLKGVKLHYT

Wuhan spike protein Receptor Binding Domain (RBD) with 4 additional amino acids

SEQ ID NO. 011
NITNLCPFGEVFNATRFASVYAWNRKRISNCVADYSVLYNSASFSTF

KCYGVSPTKLNDLCFTNVYADSFVIRGDEVRQIAPGQTGKIADYNYK

LPDDFTGCVIAWNSNNLDSKVGGNYNYLYRLFRKSNLKPFERDISTE

IYQAGSTPCNGVEGFNCYFPLQSYGFQPTNGVGYQPYRVVVLSFELL

HAPATVCGPKP

Wang et al., 2004 (Contribution of C3d-P28 repeats to enhancement of immune responses against HBV-preS2/S induced by gene immunization, World J Gastroenterol 10: 2070-2077.

A peptide, artificial sequence, containing P28 dimer, separated by a portion of the *Vibrio vulnificus* flagellin with flexible linkers. [119][120][121] A SEQ ID NO. 012
KFLTTAKDKNRWEDPGKQLYNVEATSYAGGGGSGGGGSGGGGSa qtaegamnettnilqrmrdlslqsangsnskservaiqeeital ndelnGGGGSGGGGSGGGGSKFLTTAKDKNRWEDPGKQLYNVEA

TSYA

Example 3

A yebF fusion with 38 amino acids of the RBD, expressed by an attenuated *Salmonella* VNP20009. An expression plasmid, pTrc99a, with a YebF, containing an in-frame fusion with a portion of the RBD consisting of 38 amino acids, from a cysteine to a cysteine.

SEQ ID NO. 013
atggctaaaaaagaggggcgttttagggctgttgttggtttctgcc tgcgcatcagttttcgctgccaataatgaaaccagcaagtcggtcact ttcccaaagtgtgaagatctggatgctgccggaattgccgcgagcgta aaacgtgattatcaacaaaatcgcgtggcgcgtttgggcagatgatcaa aaaattgtcggtcaggccgatcccgtggcttgggtcagtttgcaggac attcagggtaaagatgataaatggtcagtaccgctaaccgtgcgtggt aaaagtgccgatattcattaccaggtcagcgtggactgcaaagcggga atggcggaatatcagcggcgtctcgagGGTactagtGGCGGTGGTGGC AGTtgcTATTTTCCACTGCAGTCTTATGGCTTTCAGCCGACTAACGGT

GTGGGTTACCAACCGTACCGTGTGGTTGTACTGTCTTTCGAGCTGCTG

CATGCCCCGGCAACCGTATGCtaatctaga

The plasmid may further consist of an adjuvant peptide cloned in-frame into the XhoI and SpeI sites. The plasmid may further comprise a colicin expression operon, such as that consisting of colicin E3, E3 immunity, E8 immunity, and E3 lysis protein. The complete sequence of a plasmid is containing a YebF with in-frame fusions of a truncated p28 (p13), a 38 amino acid portion of the spike protein RBD, with co-expression of E3, E3 immunity, E8 immunity, and E3 lysis protein.

SEQ ID NO. 014
GTTTGACAGCTTATCATCGACTGCACGGTGCACCAATGCTTCTGGCGTC

AGGCAGCCATCGGAAGCTGTGGTATGGCTGTGCAGGTCGTAAATCACTG

CATAATTCGTGTCGCTCAAGGCGCACTCCCGTTCTGGATAATGTTTTTT

GCGCCGACATCATAACGGTTCTGGCAAATATTCTGAAATGAGCTGTTGA

CAATTAATCATCCGGCTCGTATAATGTGTGGAATTGTGAGCGGATAACA

ATTTCACACAGGAAACAGACCatggctaaaaaagaggggcgttttag ggctgttgttggtttctgcctgcgcatcagttttcgctgccaataatga aaccagcaagtcggtcactttcccaaagtgtgaagatctggatgctgcc ggaattgccgcgagcgtaaaacgtgattatcaacaaaatcgcgtggcgc gtttgggcagatgatcaaaaaattgtcggtcaggccgatcccgtggcttg ggtcagtttgcaggacattcagggtaaagatgataaatggtcagtaccg ctaaccgtgcgtggtaaaagtgccgatattcattaccaggtcagcgtgg actgcaaagcgggaatggcggaatatcagcggcgtctcgagGGCGGTGG

TGGCAGTGGAAAACAATTATACAATGTGGAAGCAACTTCGTACGCAGGC

GGCGGTGGTAGCGGCGGCGGCGGAAGCGGCGGTGGCGGTTCTGGCAAGC

AACTCTACAATGTCGAGGCCACTTCATACGGCGGTGGTGGCAGTactag tGGCGGTGGTGGCAGTtgcTATTTTCCACTGCAGTCTTATGGCTTTCAG

CCGACTAACGGTGTGGGTTACCAACCGTACCGTGTGGTTGTACTGTCTT

TCGAGCTGCTGCATGCCCCGGCAACCGTATGCtaatctagaGTCGACCT

GCAGGCATGCAAGCTTGGCTGTTTTGGCGGATGAGAGAAGATTTTCAGC

CTGATACAGATTAAATCAGAACGCAGAAGCGGTCTGATAAAACAGAATT

TGCCTGGCGGCAGTAGCGCGGTGGTCCCACCTGACCCCATGCCGAACTC

AGAAGTGAAACGCCGTAGCGCCGATGGTAGTGTGGGGTCTCCCCATGCG

AGAGTAGGGAACTGCCAGGCATCAAATAAAACGAAAGGCTCAGTCGAAA

GACTGGGCCTTTCGTTTTATCTGTTGTTTGTCGGTGAACGCTCTCCTGA

GTAGGACAAATCCGCCGGGAGCGGATTTGAACGTTGCGAAGCAACGGCC

-continued

```
CGGAGGGTGGCGGGCAGGACGCCCGCCATAAACTGCCAGGCATCAAATT
AAGCAGAAGGCCATCCTGACGGATGGCCTTTTTGCGTTTCTACAAACTC
TTTTTGTTTATTTTTCTAAATACATTCAAATATGTATCCGCTCATGAGA
CAATAACCCTGATAAATGCTTCAATAATATTGAAAAAGGAAGAGTATGA
GTATTCAACATTTCCGTGTCGCCCTTATTCCCTTTTTTGCGGCATTTTG
CCTTCCTGTTTTTGCTCACCCAGAAACGCTGGTGAAAGTAAAAGATGCT
GAAGATCAGTTGGGTGCACGAGTGGGTTACATCGAACTGGATCTCAACA
GCGGTAAGATCCTTGAGAGTTTTCGCCCCGAAGAACGTTTTCCAATGAT
GAGCACTTTTAAAGTTCTGCTATGTGGCGCGGTATTATCCCGTGTTGAC
GCCGGGCAAGAGCAACTCGGTCGCCGCATACACTATTCTCAGAATGACT
TGGTTGAGTACTCACCAGTCACAGAAAAGCATCTTACGGATGGCATGAC
AGTAAGAGAATTATGCAGTGCTGCCATAACCATGAGTGATAACACTGCG
GCCAACTTACTTCTGACAACGATCGGAGGACCGAAGGAGCTAACCGCTT
TTTTGCACAACATGGGGGATCATGTAACTCGCCTTGATCGTTGGGAACC
GGAGCTGAATGAAGCCATACCAAACGACGAGCGTGACACCACGATGCCT
ACAGCAATGGCAACAACGTTGCGCAAACTATTAACTGGCGAACTACTTA
CTCTAGCTTCCCGGCAACAATTAATAGACTGGATGGAGGCGGATAAAGT
TGCAGGACCACTTCTGCGCTCGGCCCTTCCGGCTGGCTGGTTTATTGCT
GATAAATCTGGAGCCGGTGAGCGTGGGTCTCGCGGTATCATTGCAGCAC
TGGGGCCAGATGGTAAGCCCTCCCGTATCGTAGTTATCTACACGACGGG
GAGTCAGGCAACTATGGATGAACGAAATAGACAGATCGCTGAGATAGGT
GCCTCACTGATTAAGCATTGGTAACTGTCAGACCAAGTTTACTCATATA
TACTTTAGATTGATTTAAAACTTCATTTTTAATTTAAAAGGATCTAGGT
GAAGATCCTTTTTGATAATCTCATGACCAAAATCCCTTAACGTGAGTTT
TCGTTCCACTGAGCGTCAGACCCCGTAGAAAAGATCAAAGGATCTTCTT
GAGATCCTTTTTTTCTGCGCGTAATCTGCTGCTTGCAAACAAAAAAACC
ACCGCTACCAGCGGTGGTTTGTTTGCCGGATCAAGAGCTACCAACTCTT
TTTCCGAAGGTAACTGGCTTCAGCAGAGCGCAGATACCAAATACTGTCC
TTCTAGTGTAGCCGTAGTTAGGCCACCACTTCAAGAACTCTGTAGCACC
GCCTACATACCTCGCTCTGCTAATCCTGTTACCAGTGGCTGCTGCCAGT
GGCGATAAGTCGTGTCTTACCGGGTTGGACTCAAGACGATAGTTACCGG
ATAAGGCGCAGCGGTCGGGCTGAACGGGGGGTTCGTGCACACAGCCCAG
CTTGGAGCGAACGACCTACACCGAACTGAGATACCTACAGCGTGAGCTA
TGAGAAAGCGCCACGCTTCCCGAAGGGAGAAAGGCGGACAGGTATCCGG
TAAGCGGCAGGGTCGGAACAGGAGAGCGCACGAGGGAGCTTCCAGGGGG
AAACGCCTGGTATCTTTATAGTCCTGTCGGGTTTCGCCACCTCTGACTT
GAGCGTCGATTTTTGTGATGCTCGTCAGGGGGCGGAGCCTATGGAAAA
ACGCCAGCAACGCGGCCTTTTTACGGTTCCTGGCCTTTTGCTGGCCTTT
TGCTCACATGTTCTTTCCTGCGTTATCCCCTGATTCTGTGGATAACCGT
ATTACCGCCTTTGAGTGAGCTGATACCGCTCGCCGCAGCCGAACGACCG
AGCGCAGCGAGTCAGTGAGCGAGGAAGCGGAAGAGCGCCTGATGCGGTA

TTTTCTCCTTACGCATCTGTGCGGTATTTCACACCGCATATGcccgctc
tgcgttttctaagtgttatccctcctgatttctaaaaaattttccacct
gaacTTGACagaaaaaacgatgacgagtacttttgatctgtacataaa
cccagtggrntatgtacagtattaatcgtgtaatcaattgttttaacgc
ttaaaagagggaattttatgagcggtggcgatggacgcggccataaca
cgggcgcgcatagcacaagtggtaacattaatggtggcccgaccggct
tggtgtaggtggtggtgcttctgatggctccggatggagttcggaaaat
aacccgtggggtggtggttccggtagcggcattcactggggtggtggtt
ccggtcatggtaatggcggggggaatggtaattccggtggtggttcggg
aacaggcggtaatctgtcagcagtagctgcgccagtggcatttggtttt
ccggcacttccactccaggagctggcggtctggcggtcagtatttcag
cgggagcattatcggcagctattgctgatattatggctgccctgaaagg
accgtttaaatttggtcttgggggtggctttatatggtgtattgcca
tcacaaatagcgaaagatgacccaatatgatgtcaaagattgtgacgt
cattacccgcagatgatattactgaatcacctgtcagttcattacctct
cgataaggcaacagtaaacgtaaatgttcgtgttgttgatgatgtaaaa
gacgagcgacagaatatttcggttgtttcaggtgttccgatgagtgttc
cggtggttgatgcaaaacctaccgaacgtccgggtgtttttacggcatc
aattccaggtgcacctgttctgaatatttcagttaataacagtacgcca
gcagtacagacattaagcccaggtgttacaaataatactgataaggatg
ttcgcccggcaggatttactcaggtggtaataccagggatgcagttat
tcgattcccgaaggacagcggtcataatgccgtatatgtttcagtgagt
gatgttcttagccctgaccaggtaaaacaacgtcaagatgaagaaaatc
gccgtcagcaggaatgggatgctacgcatccggttgaagcggctgagcg
aaattatgaacgcgcgcgtgcagagctgaatcaggcaaatgaagatgtt
gccagaaatcaggagcgacaggctaaagctgttcaggtttataattcgc
gtaaaagcgaacttgatgcagcgaataaaactcttgctgatgcaatagc
tgaaataaaacaatttaatcgatttgcccatgacccaatggctggcggt
cacagaatgtggcaaatggccgggcttaaagcccagcgggcgcagacgg
atgtaaataataagcaggctgcatttgatgctgctgcaaaagagaagtc
agatgctgatgctgcattgagttctgctatggaaagcaggaagaagaaa
gaagataagaaaaggagtgctgaaaataatttaaacgatgaaaagaata
agcccagaaaaggttttaaagattacgggcatgattatcatccagctcc
gaaaactgagaatattaaagggcttggtgatcttaagcctgggatacca
aaaacaccaaagcagaatggtggtggaaaacgcaagcgctggactggag
ataaagggcgtaagatttatgagtgggattctcagcatggtgagcttga
ggggtatcgtgccagtgatggtcagcatcttggctcatttgaccctaaa
acaggcaatcagttgaaaggtccagatccgaaacgaaatatcaagaaat
atctttgagaggaagttatgggacttaaattggatttaacttggtttga
taaaagtacagaagattttaagggtgaggagtattcaaaagattttgga
```

```
-continued
gatgacggttcagttatggaaagtctaggtgtgccttttaaggataatg ttaataacggttgctttgatgttatagctgaatgggtacctttgctaca accatactttaatcatcaaattgatatttccgataatgagtattttgtt tcgtttgattatcgTGATGGTGATTGGTGAtcaaatattatcagggatg agttgatatacgggcttctagtgttcatggatgaacgctggagcctcca aatgtagaaatgttatattttttattgagttcttggttataattgctcc gcaatgatttaaataagcattatttaaaacattctcaggagaggtgaag gtggagctaaaaaaagtattggtgattacactgaaaccgaattcaaaa aatttattgaagacatcatcaattgtgaaggtgatgaaaaaaaacagga tgataacctcgagtattttataaatgttactgagcatcctagtggttct gatctgatttattacccagaaggtaataatgatggtagccctgaaggtg ttattaaagagattaaagaatggcgagccgctaacggtaagtcaggatt taaacagggctgaaatatgaatgccggttgtttatggatgaatggctgg cattctttcacaacaaggagtcgttatgaaaaaaataacagggattatt ttattgcttcttgcagtcattattctgtctgcatgtcaggcaaactata tccgggatgttcagggcgggaccgtatctccgtcatcaacagctgaagt gaccggattagcaacgcagtaacccgaaatcctctttgacaaaaacaaa gcgtgtcaggctGCGGCCGCCCATTGCTGIGGAAGCTGCCTGCACTAAT

GTTCCGGCGTTATTTCTTGATGTCTCTGACCAGACACCCATCAACAGTA

TTATTTTCTCCCATGAAGACGGTACGCGACTGGGCGTGGAGCATCTGGT

CGCATTGGGTCACCAGCAAATCGCGCTGTTAGCGGGCCCATTAAGTTCT

GTCTCGGCGCGTCTGCGTCTGGCTGGCTGGCATAAATATCTCACTCGCA

ATCAAATTCAGCCGATAGCGGAACGGGAAGGCGACTGGAGTGCCATGTC

CGGTTTTCAACAAACCATGCAAATGCTGAATGAGGGCATCGTTCCCACT

GCGATGCTGGTTGCCAACGATCAGATGGCGCTGGGCGCAATGCGCGCCA

TTACCGAGTCCGGGCTGCGCGTTGGTGCGGATATCTCGGTAGTGGGATA

CGACGATACCGAAGACAGCTCATGTTATATCCCGCCGTTAACCACCATC

AAACAGGATTTTCGCCTGCTGGGGCAAACCAGCGTGGACCGCTTGCTGC

AACTCTCTCAGGGCCAGGCGGTGAAGGGCAATCAGCTGTTGCCCGTCTC

ACTGGTGAAAAGAAAAACCACCCTGGCGCCCAATACGCAAACCGCCTCT

CCCCGCGCGTTGGCCGATTCATTAATGCAGCTGGCACGACAGGTTTCCC

GACTGGAAAGCGGGCAGTGAGCGCAACGCAATTAATGTGAGTTAGCGCG

AATTGATCTG
```

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

REFERENCES

Each of the references cited herein is expressly incorporated herein by reference in its entirety.
1. Guan W J, Ni Z Y, Hu Y, Liang W H, Ou C Q, He J X, et al. (April 2020). "Clinical Characteristics of Coronavirus Disease 2019 in China". The New England Journal of Medicine. Massachusetts Medical Society. 382 (18): 1708-1720. doi:10.1056/nejmoa2002032. PMC 7092819. PMID 32109013.
2. Wei X S, Wang X, Niu Y R, Ye L L, Peng W B, Wang Z H, et al. (26 Feb. 2020). "Clinical Characteristics of SARS-CoV-2 Infected Pneumonia with Diarrhea". doi: 10.2139/ssrn.3546120.
3. Huang C, Wang Y, Li X, Ren L, Zhao J, Hu Y, et al. (February 2020). "Clinical features of patients infected with 2019 novel coronavirus in Wuhan, China". Lancet. 395 (10223): 497-506. doi:10.1016/S0140-6736(20) 30183-5. PMC 7159299. PMID 31986264.
4. Lai C C, Shih T P, Ko W C, Tang H J, Hsueh P R (March 2020). "Severe acute respiratory syndrome coronavirus 2 (SARS-CoV-2) and coronavirus disease-2019 (COVID-19): The epidemic and the challenges". International Journal of Antimicrobial Agents. 55 (3): 105924. doi: 10.1016/j.ijantimicag.2020.105924. PMC 7127800. PMID 32081636.
5. To K K, Tsang O T, Chik-Yan Yip C, Chan K H, Wu T C, Chan J M, et al. (February 2020). "Consistent detection of 2019 novel coronavirus in saliva". Clinical Infectious Diseases. Oxford University Press. doi:10.1093/cid/ciaa149. PMC 7108139. PMID 32047895.
6. Zhu N, Zhang D, Wang W, Li X, Yang B, Song J, et al. (February 2020). "A Novel Coronavirus from Patients with Pneumonia in China, 2019". The New England Journal of Medicine. 382 (8): 727-733. doi:10.1056/NEJMoa2001017. PMC 7092803. PMID 31978945.
7. Cyranoski D (March 2020). "Mystery deepens over animal source of coronavirus". Nature. 579 (7797): 18-19. Bibcode:2020Natur.579 . . . 18C. doi:10.1038/d41586-020-00548-w. PMID 32127703.
8. Letko M, Marzi A, Munster V (April 2020). "Functional assessment of cell entry and receptor usage for SARS-CoV-2 and other lineage B betacoronaviruses". Nature Microbiology. 5 (4): 562-569. doi:10.1038/s41564-020-0688-y. PMC 7095430. PMID 32094589.
9. Zhang H, Penninger J M, Li Y, Zhong N, Slutsky A S (April 2020). "Angiotensin-converting enzyme 2 (ACE2) as a SARS-CoV-2 receptor: molecular mechanisms and potential therapeutic target". Intensive Care Medicine. 46 (4): 586-590. doi:10.1007/s00134-020-05985-9. PMC 7079879. PMID 32125455.
10. Xu H, Zhong L, Deng J, Peng J, Dan H, Zeng X, et al. (February 2020). "High expression of ACE2 receptor of 2019-nCoV on the epithelial cells of oral mucosa". International Journal of Oral Science. 12 (1): 8. doi:10.1038/s41368-020-0074-x. PMC 7039956. PMID 32094336.
11. Gurwitz D (March 2020). "Angiotensin receptor blockers as tentative SARS-CoV-2 therapeutics". Drug Development Research. doi:10.1002/ddr.21656. PMID 32129518.
12. Gu J, Han B, Wang J (May 2020). "COVID-19: Gastrointestinal Manifestations and Potential Fecal-Oral Transmission". Gastroenterology. 158 (6): 1518-1519. doi:10.1053/j.gastro.2020.02.054. PMC 7130192. PMID 32142785.
13. Hamming I, Timens W, Bulthuis M L, Lely A T, Navis G, van Goor H (June 2004). "Tissue distribution of ACE2 protein, the functional receptor for SARS coronavirus. A first step in understanding SARS pathogenesis". The Journal of Pathology. 203 (2): 631-7. doi:10.1002/path.1570. PMC 7167720. PMID 15141377.
14. Zheng Y Y, Ma Y T, Zhang J Y, Xie X (May 2020). "COVID-19 and the cardiovascular system". Nature Reviews. Cardiology. 17(5): 259-260. doi:10.1038/s41569-020-0360-5. PMC 7095524. PMID 32139904.
15. Turner A J, Hiscox J A, Hooper N M (June 2004). "ACE2: from vasopeptidase to SARS virus receptor". Trends in Pharmacological Sciences. 25 (6): 291-4. doi:10.1016/j.tips.2004.04.001. PMC 7119032. PMID 15165741.
16. Zhang C, Wu Z, Li J W, Zhao H, Wang G Q (March 2020). "The cytokine release syndrome (CRS) of severe COVID-19 and Interleukin-6 receptor (IL-6R) antagonist Tocilizumab may be the key to reduce the mortality". International Journal of Antimicrobial Agents: 105954. doi:10.1016/j.ijantimicag.2020.105954. PMC 7118634. PMID 32234467.
17. Zhou Y, Fu B, Zheng X, Wang D, Zhao C, Qi Y, et al. (2020). "Aberrant pathogenic GM-CSF+ T cells and inflammatory CD14+CD16+ monocytes in severe pulmonary syndrome patients of a new coronavirus". bioRxiv Pre-print: 2020.02.12.945576. doi:10.1101/2020.02.12.945576.
18. "BSI open letter to Government on SARS-CoV-2 outbreak response". immunology.org. British Society for Immunology. Archived from the original on 14 Mar. 2020. Retrieved 15 Mar. 2020.
19. Schraer, Rachel (25 Apr. 2020). "Coronavirus: Immunity passports 'could increase virus spread'". Retrieved 26 Apr. 2020.
20. "Can you get coronavirus twice or does it cause immunity?". The Independent. 13 Mar. 2020. Archived from the original on 14 Mar. 2020. Retrieved 15 Mar. 2020.
21. Politi D (11 Apr. 2020). "WHO Investigating Reports of Coronavirus Patients Testing Positive Again After Recovery". Slate. Retrieved 11 Apr. 2020.
22. "They survived the coronavirus. Then they tested positive again. Why?". Los Angeles Times. 13 Mar. 2020. Archived from the original on 14 Mar. 2020. Retrieved 15 Mar. 2020.
23. "14% of Recovered Covid-19 Patients in Guangdong Tested Positive Again". caixinglobal.com. Caixin Global. Archived from the original on 3 Mar. 2020. Retrieved 15 Mar. 2020.
24. Omer S B, Malani P, Del Rio C (April 2020). "The COVID-19 Pandemic in the US: A Clinical Update". Jama. doi:10.1001/jama.2020.5788. PMID 32250388.
25. Parry R L (30 Apr. 2020), "Coronavirus patients can't relapse, South Korean scientists believe", The Times
26. "What if immunity to covid-19 doesn't last?". MIT Technology Review. Retrieved 1 May 2020.
27. "Direct observation of repeated infections with endemic coronaviruses" (PDF). Columbia University in the City of New York. Department of Environmental Health Sciences, Mailman School of Public Health, Columbia University. 15 Apr. 2020. Retrieved 2 May 2020.
28. Chen W H, Strych U, Hotez P J, Bottazzi M E (March 2020). "The SARS-CoV-2 Vaccine Pipeline: an Overview". Current Tropical Medicine Reports: 1-4. doi: 10.1007/s40475-020-00201-6. PMC 7094941. PMID 32219057.
29. Peeples L (April 2020). "News Feature: Avoiding pitfalls in the pursuit of a COVID-19 vaccine". Proceedings of the National Academy of Sciences of the United States of America. Proceedings of the National Academy of Sciences. 117 (15): 8218-8221. doi:10.1073/pnas.2005456117. PMC 7165470. PMID 32229574.
30. Yao X, Ye F, Zhang M, Cui C, Huang B, Niu P, et al. (March 2020). "In Vitro Antiviral Activity and Projection of Optimized Dosing Design of Hydroxychloroquine for the Treatment of Severe Acute Respiratory Syndrome Coronavirus 2 (SARS-CoV-2)". Clinical Infectious Diseases. doi:10.1093/cid/ciaa237. PMC 7108130. PMID 32150618.
31. Liu R, Miller J (3 Mar. 2020). "China approves use of Roche drug in battle against coronavirus complications". Reuters. Archived from the original on 12 Mar. 2020. Retrieved 14 Mar. 2020.
32. "Effective Treatment of Severe COVID-19 Patients with Tocilizumab". ChinaXiv.org. 5 Mar. 2020. doi:10.12074/202003.00026 (inactive 26 Apr. 2020). Archived from the original on 19 Mar. 2020. Retrieved 14 Mar. 2020.
33. Ovadia D, Agenzia Z. "COVID-19—Italy launches an independent trial on tocilizumab". Univadis from Medscape. Aptus Health. Retrieved 22 Apr. 2020.
34. "Tocilizumab in COVID-19 Pneumonia (TOCIVID-19) (TOCIVID-19)". www.clinicaltrials.gov. National Library of Medicine. Retrieved 22 Apr. 2020.
35. "How doctors can potentially significantly reduce the number of deaths from Covid-19". Vox. 12 Mar. 2020. Archived from the original on 19 Mar. 2020. Retrieved 14 Mar. 2020.
36. Ruan Q, Yang K, Wang W, Jiang L, Song J (March 2020). "Clinical predictors of mortality due to COVID-19 based on an analysis of data of 150 patients from Wuhan, China". Intensive Care Medicine. doi:10.1007/s00134-020-05991-x. PMC 7080116. PMID 32125452.
37. Mehta P, McAuley D F, Brown M, Sanchez E, Tattersall R S, Manson J J (March 2020). "COVID-19: consider cytokine storm syndromes and immunosuppression". Lancet. 395 (10229): 1033-1034. doi:10.1016/S0140-6736(20) 30628-0. PMID 32192578.
38. Slater H (26 Mar. 2020). "FDA Approves Phase III Clinical Trial of Tocilizumab for COVID-19 Pneumonia". www.cancernetwork.com. Cancer Network. Retrieved 22 Apr. 2020.

39. Sterner R M, Sakemura R, Cox M J, Yang N, Khadka R H, Forsman C L, et al. (February 2019). "GM-CSF inhibition reduces cytokine release syndrome and neuroinflammation but enhances CAR-T cell function in xenografts". Blood. 133 (7): 697-709. doi:10.1182/blood-2018-10-881722. PMC 6376281. PMID 30463995.
40. "Northwell Health Initiates Clinical Trials of 2 COVID-19 Drugs". 21 Mar. 2020. Archived from the original on 23 Mar. 2020. Retrieved 23 Mar. 2020.
41. Casadevall A, Pirofski L A (April 2020). "The convalescent sera option for containing COVID-19". The Journal of Clinical Investigation. 130 (4): 1545-1548. doi: 10.1172/JCI138003. PMC 7108922. PMID 32167489.
42. Pearce K (13 Mar. 2020). "Antibodies from COVID-19 survivors could be used to treat patients, protect those at risk: Infusions of antibody-laden blood have been used with reported success in prior outbreaks, including the SARS epidemic and the 1918 flu pandemic". The Hub at Johns Hopkins University. Archived from the original on 14 Mar. 2020. Retrieved 14 Mar. 2020.
42. Wu F, Zhao S, Yu B, Chen Y M, Wang W, Song Z G, et al. A new coronavirus associated with human respiratory disease in China. Nature [Preprint]. 2020 [cited 2020 Feb. 16]: [19 p.]. Available from: doi.org/10.1038/s41586-020-2008-3.
43. Lu R, Zhao X, Li J, Niu P, Yang B, Wu H, et al. Genomic characterisation and epidemiology of 2019 novel coronavirus: implications for virus origins and receptor binding. Lancet. 2020; 395:565-74.
44. Hoffmann M K-W H, Krüger N, Müller M, Drosten C, Pöhlmann S. The novel coronavirus 2019 (2019-nCoV) uses the SARS-coronavirus receptor ACE2 and the cellular protease TMPRSS2 for entry into target cells. bioRxiv [Preprint]. 2020 [cited 2020 Feb. 16]: [23 p.]. Available from: www.biorxiv.org/content/10.1101/2020.01.31.929042v1
45. Zhou P, Yang X L, Wang X G, Hu B, Zhang L, Zhang W, et al. A pneumonia outbreak associated with a new coronavirus of probable bat origin. Nature [Preprint]. 2020 [cited 2020 Feb. 15]: [15 p.]. Available from: doi.org/10.1038/s41586-020-2012-7
46. Huang C, Wang Y, Li X, Ren L, Zhao J, Hu Y, et al. Clinical features of patients infected with 2019 novel coronavirus in Wuhan, China. Lancet. 2020; 395:497-506.
47. Mahallawi W H, Khabour O F, Zhang Q, Makhdoum H M, Suliman B A. MERS-CoV infection in humans is associated with a pro-inflammatory Th1 and Th17 cytokine profile. Cytokine. 2018; 104:8-13.
48. Wong C K, Lam C W, Wu A K, Ip W K, Lee N L, Chan I H, et al. Plasma inflammatory cytokines and chemokines in severe acute respiratory syndrome. Clin Exp Immunol. 2004; 136:95-103.
49. Perlman S, Dandekar A A. Immunopathogenesis of coronavirus infections: implications for SARS. Nat Rev Immunol. 2005; 5(12):917-27.
50. Zhu N, Zhang D, Wang W, Li X, Yang B, Song J, et al. A Novel Coronavirus from Patients with Pneumonia in China, 2019. N Engl J Med. 2020; 382:727-33.
51. de Wit E, van Doremalen N, Falzarano D, Munster V J. SARS and MERS: recent insights into emerging coronaviruses. Nat Rev Microbiol. 2016; 14: 523-34.
52. Kindler E, Thiel V, Weber F. Interaction of SARS and MERS Coronaviruses with the Antiviral Interferon Response. Adv Virus Res. 2016; 96:219-43.
53. Perlman S, Dandekar A A. Immunopathogenesis of coronavirus infections: implications for SARS. Nat Rev Immunol. 2005; 5(12):917-27.
54. Zumla A, Hui D S, Perlman S. Middle East respiratory syndrome. Lancet. 2015; 386:995-1007.
55. Channappanavar R, Perlman S. Pathogenic human coronavirus infections: causes and consequences of cytokine storm and immunopathology. Semin Immunopathol. 2017; 39:529-39.
56. Liu W J, Zhao M, Liu K, Xu K, Wong G, Tan W, et al. T-cell immunity of SARS-CoV: Implications for vaccine development against MERS-CoV. Antiviral Res. 2017; 137:82-92.
57. Liu W, Fontanet A, Zhang P H, Zhan L, Xin Z T, Baril L, et al. Two-year prospective study of the humoral immune response of patients with severe acute respiratory syndrome. J Infect Dis. 2006; 193:792-5.
58. Li C K, Wu H, Yan H, Ma S, Wang L, Zhang M, et al. T cell responses to whole SARS coronavirus in humans. J Immunol. 2008; 181:5490-500.
59. Shin H S, Kim Y, Kim G, Lee J Y, Jeong I, Joh J S, et al. Immune Responses to Middle East Respiratory Syndrome Coronavirus During the Acute and Convalescent Phases of Human Infection. Clin Infect Dis. 2019; 68: 984-92.
60. Zhao J, Zhao J, Mangalam A K, Channappanavar R, Fett C, Meyerholz D K, et al. Airway Memory CD4(+) T Cells Mediate Protective Immunity against Emerging Respiratory Coronaviruses. Immunity. 2016; 44:1379-91.
61. Shokri S, Mahmoudvand S, Taherkhani R, Farshadpour F. Modulation of the immune response by Middle East respiratory syndrome coronavirus. J Cell Physiol. 2019; 234:2143-51.
62. Kikkert M. Innate Immune Evasion by Human Respiratory RNA Viruses. J Innate Immun. 2020; 12:4-20.
63. Faure E, Poissy J, Goffard A, Fournier C, Kipnis E, Titecat M, et al. Distinct immune response in two MERS-CoV-infected patients: can we go from bench to bedside? PLoS One. 2014; 9:e88716.
64. Al-Amri S S, Abbas A T, Siddiq L A, Alghamdi A, Sanki M A, Al-Muhanna M K, et al. Immunogenicity of Candidate MERS-CoV DNA Vaccines Based on the Spike Protein. Sci Rep. 2017; 7:44875.
65. Du L, He Y, Zhou Y, Liu S, Zheng B J, Jiang S. The spike protein of SARS-CoV—a target for vaccine and therapeutic development. Nat Rev Microbiol. 2009; 7:226-36.
66. Du L, Zhao G, He Y, Guo Y, Zheng B J, Jiang S, et al. Receptor-binding domain of SARS-CoV spike protein induces long-term protective immunity in an animal model. Vaccine. 2007; 25:2832-8.
67. Tebas P, Roberts C C, Muthumani K, Reuschel E L, Kudchodkar S B, Zaidi F I, et al. Safety and Immunogenicity of an Anti-Zika Virus DNA Vaccine Preliminary Report. N Engl J Med [Preprint]. 2017[cited 2020 Feb. 10]:[16 p.]. Available from: doi.org/10.1056/NEJMoa1708120
68. Pardi N, Hogan M J, Porter F W, Weissman D. mRNA vaccines a new era in vaccinology. Nat Rev Drug Discov. 2018; 17:261-79.
69. Maruggi G, Zhang C, Li J, Ulmer J B, Yu D. mRNA as a Transformative Technology for Vaccine Development to Control Infectious Diseases. Mol Ther. 2019; 27:757-72.
70. Zhou, P.; Yang, X.-L.; Wang, X.-G.; Hu, B.; Zhang, L.; Zhang, W.; Si, H.-R.; Zhu, Y.; Li, B.; Huang, C.-L.; et al. A pneumonia outbreak associated with a new coronavirus of probable bat origin. Nature 2020.

71. Lu, R.; Zhao, X.; Li, J.; Niu, P.; Yang, B.; Wu, H.; Wang, W.; Song, H.; Huang, B.; Zhu, N.; et al. Genomic characterisation and epidemiology of 2019 novel coronavirus: Implications for virus origins and receptor binding. Lancet 2020, 6736, 1-10.
72. Letko, M.; Munster, V. Functional assessment of cell entry and receptor usage for lineage B β-coronaviruses, including 2019-nCoV. bioRxiv 2020, 2020.01.22.915660.
73. Hoffmann, M.; Kleine-Weber, H.; Kruger, N.; Muller, M.; Drosten, C.; Pohlmann, S. The novel coronavirus 2019 (2019-nCoV) uses the SARS-coronavirus receptor ACE2 and the cellular protease TMPRSS2 for entry into target cells. bioRxiv 2020, 2020.01.31.929042.
74. Yang, Z.-Y.; Kong, W.-P.; Huang, Y.; Roberts, A.; Murphy, B. R.; Subbarao, K.; Nabel, G. J. A DNA vaccine induces SARS coronavirus neutralization and protective immunity in mice. Nature 2004, 428, 561-564.
75. Deming, D.; Sheahan, T.; Heise, M.; Yount, B.; Davis, N.; Sims, A.; Suthar, M.; Harkema, J.; Whitmore, A.; Pickles, R.; et al. Vaccine efficacy in senescent mice challenged with recombinant SARS-CoV bearing epidemic and zoonotic spike variants. PLoS Med. 2006, 3, e525.
76. Graham, R. L.; Becker, M. M.; Eckerle, L. D.; Bolles, M.; Denison, M. R.; Baric, R. S. A live, impaired-fidelity coronavirus vaccine protects in an aged, immunocompromised mouse model of lethal disease. Nat. Med. 2012, 18, 1820-1826.
77. Lin, Y.; Shen, X.; Yang, R. F.; Li, Y. X.; Ji, Y. Y.; He, Y. Y.; De Shi, M.; Lu, W.; Shi, T. L.; Wang, J.; et al. Identification of an epitope of SARS-coronavirus nucleocapsid protein. Cell Res. 2003, 13, 141-145.
78. Wang, J.; Wen, J.; Li, J.; Yin, J.; Zhu, Q.; Wang, H.; Yang, Y.; Qin, E.; You, B.; Li, W.; et al. Assessment of immunoreactive synthetic peptides from the structural proteins of severe acute respiratory syndrome coronavirus. Clin. Chem. 2003, 49, 1989-1996.
79. Liu, X.; Shi, Y.; Li, P.; Li, L.; Yi, Y.; Ma, Q.; Cao, C. Profile of antibodies to the nucleocapsid protein of the severe acute respiratory syndrome (SARS)-associated coronavirus in probable SARS patients. Clin. Vaccine Immunol. 2004, 11, 227-228.
80. Tang, F.; Quan, Y.; Xin, Z.-T.; Wrammert, J.; Ma, M.-J.; Lv, H.; Wang, T.-B.; Yang, H.; Richardus, J. H.; Liu, W.; et al. Lack of peripheral memory B cell responses in recovered patients with severe acute respiratory syndrome: A six-year follow-up study. J. Immunol. 2011, 186, 7264-7268.
81. Peng, H.; Yang, L.-T.; Wang, L.-Y.; Li, J.; Huang, J.; Lu, Z.-Q.; Koup, R. A.; Bailer, R. T.; Wu, C.-Y. Long-lived memory T lymphocyte responses against SARS coronavirus nucleocapsid protein in SARS-recovered patients. Virology 2006, 351, 466-475.
82. Fan, Y.-Y.; Huang, Z.-T.; Li, L.; Wu, M.-H.; Yu, T.; Koup, R. A.; Bailer, R. T.; Wu, C.-Y. Characterization of SARS-CoV-specific memory T cells from recovered individuals 4 years after infection. Arch. Virol. 2009, 154, 1093-1099.
83. Prompetchara, Eakachai, Chutitorn Ketloy, and Tanapat Palaga. "Immune responses in COVID-19 and potential vaccines: Lessons learned from SARS and MERS epidemic." Asian Pac J Allergy Immunol 38, no. 1 (2020): 1-9.
84. Ahmed, Syed Faraz, Ahmed A. Quadeer, and Matthew R. McKay. "Preliminary identification of potential vaccine targets for the COVID-19 coronavirus (SARS-CoV-2) based on SARS-CoV immunological studies." Viruses 12, no. 3 (2020): 254.
85. Ibarra J A, Steele-Mortimer O. 2009. *Salmonella*—the ultimate insider. *Salmonella* virulence factors that modulate intracellular survival. Cell Microbiol 11:1579-1586.
86. Haraga A, Ohlson M B, Miller S I. Salmonellae interplay with host cells. Nature reviews Microbiology. 2008; 6(1): 53-66. 10.1038/nrmicro1788
87. Gerlach R G, Hensel M. *Salmonella* pathogenicity islands in host specificity, host pathogen-interactions and antibiotics resistance of *Salmonella enterica*. Berliner und Munchener tierarztliche Wochenschrift. 2007; 120(7-8): 317-27.
88. Lee A K, Detweiler C S, Falkow S. OmpR regulates the two-component system SsrA-ssrB in *Salmonella* pathogenicity island 2. Journal of bacteriology. 2000; 182(3): 771-81. 10.1128/jb.182.3.771-781.2000
89. Panthel K, Meinel K M, Sevil Domenech V E, Trulzsch K, Russmann H. *Salmonella* type III-mediated heterologous antigen delivery: a versatile oral vaccination strategy to induce cellular immunity against infectious agents and tumors. International journal of medical microbiology: IJMM. 2008; 298(1-2):99-103. 10.1016/j.ijmm.2007.07.002
90. Xiong G, Husseiny M I, Song L, Erdreich-Epstein A, Shackleford G M, Seeger R C, et al. Novel cancer vaccine based on genes of *Salmonella* pathogenicity island 2. International journal of cancer. 2010; 126(11):2622-34. 10.1002/ijc.24957
91. Galen J E, Buskirk A D, Tennant S M, Pasetti M F, "Live Attenuated Human *Salmonella* Vaccine Candidates: Tracking the Pathogen in Natural Infection and Stimulation of Host Immunity", EcoSal Plus. 2016 November; 7(1). doi: 10.1128/ecosalplus.ESP-0010-2016.
92. Clark-Curtiss J E, Curtiss R. 2018. *Salmonella* Vaccines: Conduits for Protective Antigens. Journal of immunology (Baltimore, Md.: 1950) 200:39-48
93. Galen J E, Buskirk A D, Tennant S M, Pasetti M F. 2016. Live Attenuated Human *Salmonella* Vaccine Candidates: Tracking the Pathogen in Natural Infection and Stimulation of Host Immunity. EcoSal Plus 7
94. Clairmont C, Lee K C, Pike J, Ittensohn M, Low K B, Pawelek J, Bermudes D, Brecher S M, Margitich D, Turnier J, Li Z, Luo X, King I, Zheng L M. 2000. Biodistribution and genetic stability of the novel antitumor agent VNP20009, a genetically modified strain of *Salmonella typhimurium*. The Journal of infectious diseases 181:1996-2002.
95. Bolhassani, Azam, and Farnaz Zahedifard. "Therapeutic live vaccines as a potential anticancer strategy." International journal of cancer 131, no. 8 (2012): 1733-1743.
96. Medina, Eva, and Carlos Alberto Guzmin. "Use of live bacterial vaccine vectors for antigen delivery: potential and limitations." Vaccine 19, no. 13-14 (2001): 1573-1580.
97. Seegers, Jos F M L. "Lactobacilli as live vaccine delivery vectors: progress and prospects." Trends in biotechnology 20, no. 12 (2002): 508-515.
98. Shams, Homayoun. "Recent developments in veterinary vaccinology." The veterinary journal 170, no. 3 (2005): 289-299; Kang, Ho Young, Jay Srinivasan, and Roy Curtiss. "Immune responses to recombinant pneumococcal PspA antigen delivered by live attenuated *Salmonella enterica* serovar *Typhimurium* vaccine." Infection and immunity 70, no. 4 (2002): 1739-1749.

99. Cardenas, Lucia, and J. D. Clements. "Oral immunization using live attenuated *Salmonella* spp. as carriers of foreign antigens." Clinical microbiology reviews 5, no. 3 (1992): 328-342.

100. Buckley, Anthony M., Jinhong Wang, Debra L. Hudson, Andrew J. Grant, Michael A. Jones, Duncan J. Maskell, and Mark P. Stevens. "Evaluation of live-attenuated *Salmonella* vaccines expressing *Campylobacter* antigens for control of *C. jejuni* in poultry." Vaccine 28, no. 4 (2010): 1094-1105.

101. Dougan, G., C. E. Hormaeche, and D. J. Maskell. "Live oral *Salmonella* vaccines: potential use of attenuated strains as carriers of heterologous antigens to the immune system." Parasite immunology 9, no. 2 (1987): 151-160.

102. Mastroeni, Pietro, Bernardo Villarreal-Ramos, and Carlos E. Hormaeche. "Role of T cells, TNFα and IFNγ in recall of immunity to oral challenge with virulent salmonellae in mice vaccinated with live attenuated aro-*salmonella* vaccines." Microbial pathogenesis 13, no. 6 (1992): 477-491

103. Galen, James E., Oscar G. Gomez-Duarte, Genevieve A. Losonsky, Jane L. Halpern, Carol S. Lauderbaugh, Shevon Kaintuck, Mardi K. Reymann, and Myron M. Levine. "A murine model of intranasal immunization to assess the immunogenicity of attenuated *Salmonella typhi* live vector vaccines in stimulating serum antibody responses to expressed foreign antigens." Vaccine 15, no. 6-7 (1997): 700-708.

104. Shahabi, Vafa, Paulo C. Maciag, Sandra Rivera, and Anu Wallecha. "Live, attenuated strains of *Listeria* and *Salmonella* as vaccine vectors in cancer treatment." Bioengineered bugs 1, no. 4 (2010): 237-245.

105. Fraillery, Dominique, David Baud, Susana Yuk-Ying Pang, John Schiller, Martine Bobst, Nathalie Zosso, Frangoise Ponci, and Denise Nardelli-Haefliger. "*Salmonella enterica* serovar *Typhi* Ty21a expressing human papillomavirus type 16 L1 as a potential live vaccine against cervical cancer and typhoid fever." Clin. Vaccine Immunol. 14, no. 10 (2007): 1285-1295.

106. Paterson, Yvonne, Patrick D. Guirnalda, and Laurence M. Wood. "*Listeria* and *Salmonella* bacterial vectors of tumor-associated antigens for cancer immunotherapy." In Seminars in immunology, vol. 22, no. 3, pp. 183-189. Academic Press, 2010.

107. Wieckowski, Sébastien, Lilli Podola, Marco Springer, Iris Kobl, Zina Koob, Caroline Mignard, Amine Adda Berkane et al. "Immunogenicity and antitumor efficacy of live attenuated *Salmonella typhimurium*-based oral T-cell vaccines VXMO1m, VXM04m and VXM06m." (2017): 4558-4558.

108. Wieckowski, Sébastien, Lilli Podola, Marco Springer, Iris Kobl, Zina Koob, Caroline Mignard, Alan Broadmeadow et al. "Non-clinical safety, immunogenicity and antitumor efficacy of live attenuated *Salmonella Typhimurium*-based oral T-cell vaccines VXMOlm, VXM04m and VXM06m." In Molecular Therapy, vol. 25, no. 5, pp. 360-360. 50 Hampshire St, Floor 5, Cambridge, Mass. 02139 USA: Cell Press, 2017.

109. Wieckowski, Sébastien, Lilli Podola, Heiko Smetak, Anne-Lucie Nugues, Philippe Slos, Amine Adda Berkane, Ming Wei et al. "Modulating T cell immunity in tumors by targeting PD-L1 and neoantigens using a live attenuated oral *Salmonella* platform." (2018): 733-733

110. Vendrell, Alejandrina, Claudia Mongini, María José Gravisaco, Andrea Canellada, Agustina Inés Tesone, Juan Carlos Goin, and Claudia Inés Waldner. "An oral *salmonella*-based vaccine inhibits liver metastases by promoting tumor-specific T-cell-mediated immunity in celiac and portal lymph nodes: a preclinical study." Frontiers in Immunology 7 (2016): 72.)

111. Xiong G, Husseiny M I, Song L, Erdreich-Epstein A, Shackleford G M, Seeger R C, et al. Novel cancer vaccine based on genes of *Salmonella* pathogenicity island 2. International journal of cancer. 2010; 126(11):2622-34.

112. Toso J F, Gill V J, Hwu P, Marincola F M, Restifo N P, Schwartzentruber D J, Sherry R M, Topalian S L, Yang J C, Stock F, Freezer L J, Morton K E, Seipp C, Haworth L, Mavroukakis S, White D, MacDonald S, Mao J, Sznol M, Rosenberg S A. 2002. Phase I study of the intravenous administration of attenuated *Salmonella typhimurium* to patients with metastatic melanoma. Journal of clinical oncology: official journal of the American Society of Clinical Oncology 20:142-152.

113. Cascales, Eric, Susan K. Buchanan, Denis Duch6, Colin Kleanthous, Roland Lloubes, Kathleen Postle, Margaret Riley, Stephen Slatin, and Daniele Cavard. "Colicin biology." Microbiol. Mol. Biol. Rev. 71, no. 1 (2007): 158-229.

114. Feldgarden M, Riley M A (1999). "The phenotypic and fitness effects of colicin resistance in *Escherichia coli* K-12". Evolution. 53 (4): 1019-27. doi:10.2307/2640807. JSTOR 2640807.

115. Kang C, Postle K, Chen G, Park H, Youn B, Hilsenbeck J L (2004). "Crystal structure of the cytotoxic bacterial protein colicin B at 2.5 A resolution". Mol. Microbiol. 51 (3): 711-20. doi:10.1111/j.1365-2958.2003.03884.x. PMID 14731273.

116. Cramer W A, Zakharov S D, Antonenko Y N, Kotova E A (2004). "On the role of lipid in colicin pore formation". Biochim. Biophys. Acta. 1666 (1): 239-49. doi: 10.1016/j.bbamem.2004.07.001. PMID 15519318.

117. Cao Z, Klebba P E (2002). "Mechanisms of colicin binding and transport through outer membrane porins". Biochimie. 84 (5-6): 399-412. doi:10.1016/S0300-9084 (02)01455-4. PMID 12423783.

118. van den Elzen P J, Veltkamp E, Nijkamp H J, Walters H H (1983). "Molecular structure and function of the bacteriocin gene and bacteriocin protein of plasmid Clo DF13". Nucleic Acids Res. 11 (8): 2465-2477. doi: 10.1093/nar/11.8.2465. PMC 325896. PMID 6344017.

119. Song et al., A conserved TLR5 binding and activation hot spot on flagellin, Scientific Reports 7, Article number: 40878 (2017).

120. Lei et al., Application of built-in adjuvants for epitope-based vaccines. PeerJ 2019 Jan. 14; 6:e6185. doi: 10.7717/peerj.6185 (2018).

121. Mizel and Bates, Flagellin as an adjuvant: Cellular Mechanisms and Potential, J Immunol. 2010 Nov. 15; 185(10): 5677-5682. doi:10.4049/jimmunol.1002156.

122. Servis and Lambris, C3 synthetic peptides support growth of human Cr2-positive lymphoblastoid B cells. J Immunol 142: 2207-2212 (1989).

123. Wang et al., Contribution of C3d-P28 repeats to enhancement of immune responses against HBV-preS2/S induced by gene immunization, World J Gastroenterol 10: 2070-2077 (2004).

124. de Groot et al. 2015 *Immunol Cell Biol* 93: 189-197. doi:10.1038/icb.2014.89.

125. Lei et al., Application of built-in adjuvants for epitope-based vaccines. PeerJ 2019 Jan. 14; 6:e6185. doi: 10.7717/peerj.6185 (2018).

126. Mizel and Bates, Flagellin as an adjuvant: Cellular Mechanisms and Potential, J Immunol. 2010 Nov. 15; 185(10): 5677-5682. doi:10.4049/jimmunol.1002156 (2010).
127. Morales et al., Accumulation of single-stranded DNA in *Escherichia coli* carrying the colicin plasmid pColE3-CA3, Plasmid 77: 7-16 (2014).
128. Quintero et al., 2018, Co-expression of a chimeric protease inhibitor secreted by a tumor-targeted *Salmonella* protects therapeutic proteins from proteolytic degradation, J Microbiol Biotechnol 2018 Dec. 28; 28(12): 2079-2094. doi: 10.4014/jmb.1807.08036.
129. Amdekar, Sarika, Deepak Dwivedi, Purabi Roy, Sapna Kushwah, and Vinod Singh. "Probiotics: multifarious oral vaccine against infectious traumas." FEMS Immunology & Medical Microbiology 58, no. 3 (2010): 299-306.
130. Arnold, Heinz, Dirk Burann, Melanie Felies, Britta Gewecke, Meike Sörensen, J. Engelbert Gessner, Joachim Freihorst, Bernd Ulrich Von Specht, and Ulrich Baumann. "Enhanced immunogenicity in the murine airway mucosa with an attenuated *Salmonella* live vaccine expressing OprF-OprI from *Pseudomonas aeruginosa*." Infection and immunity 72, no. 11 (2004): 6546-6553.
131. Baud, David, Françoise Ponci, Martine Bobst, Pierre De Grandi, and Denise Nardelli-Haefliger. "Improved efficiency of a *Salmonella*-based vaccine against human papillomavirus type 16 virus-like particles achieved by using a codon-optimized version of L1." Journal of virology 78, no. 23 (2004): 12901-12909.
132. Bermúdez-Humarán, Luis G. "*Lactococcus lactis* as a live vector for mucosal delivery of therapeutic proteins." Human vaccines 5, no. 4 (2009): 264-267.
133. Blisnick, Thierry, Patrick Ave, Michel Huerre, Elisabeth Carniel, and Christian E. Demeure. "Oral vaccination against bubonic plague using a live avirulent *Yersinia pseudotuberculosis* strain." Infection and immunity 76, no. 8 (2008): 3808-3816.
134. Bolhassani, Azam, and Farnaz Zahedifard. "Therapeutic live vaccines as a potential anticancer strategy." International journal of cancer 131, no. 8 (2012): 1733-1743.
135. Branger, Christine G., Roy Curtiss III, Robert D. Perry, and Jacqueline D. Fetherston. "Oral vaccination with different antigens from *Yersinia pestis* KIM delivered by live attenuated *Salmonella typhimurium* elicits a protective immune response against plague." In The Genus *Yersinia*, pp. 387-399. Springer, New York, N.Y., 2007.
136. Bruhn, Kevin W., Noah Craft, and Jeff F. Miller. "*Listeria* as a vaccine vector." Microbes and infection 9, no. 10 (2007): 1226-1235.
137. Bumann, Dirk. "In vivo visualization of bacterial colonization, antigen expression, and specific T-cell induction following oral administration of live recombinant *Salmonella enterica* serovar *Typhimurium*." Infection and immunity 69, no. 7 (2001): 4618-4626.
138. Cardenas, Lucia, and J. D. Clements. "Oral immunization using live attenuated *Salmonella* spp. as carriers of foreign antigens." Clinical microbiology reviews 5, no. 3 (1992): 328-342.
139. Chabalgoity, José A., Gordon Dougan, Pietro Mastroeni, and Richard J. Aspinall. "Live bacteria as the basis for immunotherapies against cancer." Expert review of vaccines1, no. 4 (2002): 495-505.
140. Cheminay, Cédric, Annette Möhlenbrink, and Michael Hensel. "Intracellular *Salmonella* inhibit antigen presentation by dendritic cells." The Journal of Immunology 174, no. 5 (2005):2892-2899.
141. Chen G, Dai Y, Chen J, Wang X, Tang B, Zhu Y, et al. Oral delivery of the Sj23LHD-GST antigen by *Salmonella typhimurium* type III secretion system protects against *Schistosoma japonicum* infection in mice. PLoS neglected tropical diseases. 2011; 5(9):e1313.
142. Chen, Inês, Theresa M. Finn, Liu Yanqing, Qi Guoming, Rino Rappuoli, and Mariagrazia Pizza. "A Recombinant Live Attenuated Strain of *Vibrio cholerae* Induces Immunity against Tetanus Toxin and *Bordetella pertussis* Tracheal Colonization Factor." Infection and immunity 66, no. 4 (1998): 1648-1653.
143. Clairmont C, Lee K C, Pike J, Ittensohn M, Low K B, Pawelek J, Bermudes D, Brecher S M, Margitich D, Turnier J, Li Z, Luo X, King I, Zheng L M. 2000. Biodistribution and genetic stability of the novel antitumor agent VNP20009, a genetically modified strain of *Salmonella typhimurium*. The Journal of infectious diseases 181:1996-2002.
144. Clark-Curtiss, J. E. & Curtiss, R. *Salmonella* Vaccines: Conduits for Protective Antigens. Journal of immunology (Baltimore, Md.: 1950) 200, 39-48, doi:10.4049/jimmunol.1600608 (2018).
145. Cote-Sierra, Javier, Erik Jongert, Amin Bredan, Dinesh C. Gautam, M. Parkhouse, Pierre Cornelis, Patrick De Baetselier, and Hilde Revets. "A new membrane-bound OprI lipoprotein expression vector: high production of heterologous fusion proteins in Gram (−) bacteria and the implications for oral vaccination." Gene 221, no. 1 (1998): 25-34.
146. Cuburu N, Kim R, Guittard G C, Thompson C D, Day P M, Hamm D E, et al. A Prime-Pull-Amplify Vaccination Strategy To Maximize Induction of Circulating and Genital-Resident Intraepithelial CD8(+) Memory T Cells. Journal of immunology (Baltimore, Md.: 1950). 2019; 202(4):1250-64.
147. Darji, Ayub, Carlos A. Guzmán, Birgit Gerstel, Petra Wachholz, Kenneth N. Timmis, Jürgen Wehland, Trinad Chakraborty, and Siegfried Weiss. "Oral somatic transgene vaccination using attenuated *S. typhimurium*." Cell 91, no. 6 (1997): 765-775.
148. Del Rio, Beatriz, Raymond J. Dattwyler, Miguel Aroso, Vera Neves, Luciana Meirelles, Jos F M L Seegers, and Maria Gomes-Solecki. "Oral immunization with recombinant *Lactobacillus plantarum* induces a protective immune response in mice with Lyme disease." Clinical and Vaccine Immunology 15, no. 9 (2008): 1429-1435.
149. Detmer, Ann, and Jacob Glenting. "Live bacterial vaccines-a review and identification of potential hazards." Microbial cell factories 5, no. 1 (2006): 23.
150. Du, Aifang, and Suhua Wang. "Efficacy of a DNA vaccine delivered in attenuated *Salmonella typhimurium* against *Eimeria tenella* infection in chickens." International Journal for Parasitology 35, no. 7 (2005): 777-785.
151. Du, Lanying, Guangyu Zhao, Yuxian He, Yan Guo, Bo-Jian Zheng, Shibo Jiang, and Yusen Zhou. "Receptor-binding domain of SARS-CoV spike protein induces long-term protective immunity in an animal model." Vaccine 25, no. 15 (2007): 2832-2838.
152. Faber, Milosz, Elaine W. Lamirande, Anjeanette Roberts, Amy B. Rice, Hilary Koprowski, Bernhard Dietzschold, and Matthias J. Schnell. "A single immunization with a rhabdovirus-based vector expressing severe acute respiratory syndrome coronavirus (SARS-CoV) S protein results in the production of high levels of SARS-CoV-neutralizing antibodies." The Journal of general virology 86, no. Pt 5 (2005): 1435-1440.

153. Fayolle, C., D. O'Callaghan, P. Martineau, A. Charbit, J. M. Clément, M. Hofnung, and C. Leclerc. "Genetic control of antibody responses induced against an antigen delivered by recombinant attenuated *Salmonella typhimurium*." Infection and immunity 62, no. 10(1994):4310-4319.

154. Gahan, Michelle E., Diane E. Webster, Steven L. Wesselingh, and Richard A. Strugnell. "Impact of plasmid stability on oral DNA delivery by *Salmonella enterica* serovar *Typhimurium*." Vaccine 25, no. 8 (2007): 1476-1483.

155. Galen J E, Buskirk A D, Tennant S M, Pasetti M F. Live Attenuated Human *Salmonella* Vaccine Candidates: Tracking the Pathogen in Natural Infection and Stimulation of Host Immunity. EcoSal Plus. 2016; 7(1).

156. Galen, J. E., Buskirk, A. D., Tennant, S. M. & Pasetti, M. F. Live Attenuated Human *Salmonella* Vaccine Candidates: Tracking the Pathogen in Natural Infection and Stimulation of Host Immunity. EcoSal Plus 7, doi:10.1128/ecosalplus.ESP-0010-2016 (2016).

157. Garmory, Helen S., Sophie E C Leary, Kate F. Griffin, E. Diane Williamson, Katherine A. Brown, and Richard W. Titball. "The use of live attenuated bacteria as a delivery system for heterologous antigens." Journal of drug targeting 11, no. 8-10 (2003): 471-479.

158. Gentschev, Ivaylo, Simone Spreng, Heike Sieber, Jose Ures, Fabian Mollet, Andre Collioud, Jon Pearman et al. "Vivotif®-a 'magic shield' for protection against typhoid fever and delivery of heterologous antigens." Chemotherapy 53, no. 3 (2007): 177-180.

159. Georgiou, George, Christos Stathopoulos, Patrick S. Daugherty, Amiya R. Nayak, Brent L. Iverson, and Roy Curtiss III. "Display of heterologous proteins on the surface of microorganisms: from the screening of combinatorial libraries to live recombinant vaccines." Nature biotechnology 15, no. 1 (1997): 29-34.

160. Gerlach, Roman G., and Michael H-ensel. "*Salmonella* pathogenicity islands in host specificity, host pathogen-interactions and antibiotics resistance of *Salmonella enterica*." Berliner und Munchener tierarztliche Wochenschrift 120, no. 7/8 (2007): 317-327.

161. Glenting J, Wessels S. Ensuring safety of DNA vaccines. Microbial cell factories. 2005; 4:26.

162. Grangette, Corinne, Heide Müller-Alouf, Denise Goudercourt, Marie-Claude Geoffroy, Mireille Turneer, and Annick Mercenier. "Mucosal immune responses and protection against tetanus toxin after intranasal immunization with recombinant *Lactobacillus plantarum*." Infection and immunity69, no. 3 (2001): 1547-1553.

163. Grangette, Corinne, Heide Müller-Alouf, Marie-Claude Geoffroy, Denise Goudercourt, Mireille Turneer, and Annick Mercenier. "Protection against tetanus toxin after intragastric administration of two recombinant lactic acid bacteria: impact of strain viability and in vivo persistence." Vaccine 20, no. 27-28 (2002): 3304-3309.

164. Grifoni, Alba, John Sidney, Yun Zhang, Richard H. Scheuermann, Bjoern Peters, and Alessandro Sette. "A sequence homology and bioinformatic approach can predict candidate targets for immune responses to SARS-CoV-2." Cell host & microbe (2020).

165. Guo, Shanguang, Weiwei Yan, Sean P. McDonough, Nengfeng Lin, Katherine J. Wu, Hongxuan He, Hua Xiang, Maosheng Yang, Maira Aparecida S. Moreira, and Yung-Fu Chang. "The recombinant *Lactococcus lactis* oral vaccine induces protection against *C. difficile* spore challenge in a mouse model." Vaccine 33, no. 13 (2015): 1586-1595, doi:10.1016/j.vaccine.2015.02.006.

166. Guzman, Carlos A., Stefan Borsutzky, Monika Griot-Wenk, Ian C. Metcalfe, Jon Pearman, Andre Collioud, Didier Favre, and Guido Dietrich. "Vaccines against typhoid fever." Vaccine 24, no. 18 (2006): 3804-3811.

167. Hahn, Heinz P., and Bernd-Ulrich von Specht. "Secretory delivery of recombinant proteins in attenuated *Salmonella* strains: potential and limitations of Type I protein transporters." FEMS Immunology & Medical Microbiology 37, no. 2-3 (2003): 87-98.

168. Hansson, Marianne, and Stefan Sta. "Design and production of recombinant subunit vaccines." Biotechnology and applied biochemistry 32, no. 2 (2000): 95-107.

169. Haraga A, Ohlson M B, Miller S I. Salmonellae interplay with host cells. Nature reviews Microbiology. 2008; 6(1):53-66.

170. Harrison, J. A., B. Villarreal-Ramos, P. Mastroeni, R. Demarco de Hormaeche, and C. E. Hormaeche. "Correlates of protection induced by live Aro-*Salmonella typhimurium* vaccines in the murine typhoid model." Immunology 90, no. 4 (1997): 618-625.

171. Haselbeck, A. H. et al. Current perspectives on invasive nontyphoidal *Salmonella* disease. Curr. Opin. Infect Dis. 30, 498-503, doi:10.1097/QCO.0000000000000398 (2017).

172. Hayashi F, Smith K D, Ozinsky A, Hawn T R, Yi E C, Goodlett D R, et al. The innate immune response to bacterial flagellin is mediated by Toll-like receptor 5. Nature. 2001; 410(6832):1099-103.

173. He, Yuxian, Jingjing Li, Susanne Heck, Sara Lustigman, and Shibo Jiang. "Antigenic and immunogenic characterization of recombinant baculovirus-expressed severe acute respiratory syndrome coronavirus spike protein: implication for vaccine design." Journal of virology 80, no. 12 (2006): 5757-5767.

174. Hindle Z, Chatfield S N, Phillimore J, Bentley M, Johnson J, Cosgrove C A, et al. Characterization of *Salmonella enterica* derivatives harboring defined aroC and *Salmonella* pathogenicity island 2 type III secretion system (ssaV) mutations by immunization of healthy volunteers. Infection and immunity. 2002; 70(7):3457-67.

175. Hohmann E L, Oletta C A, Loomis W P, Miller S I. Macrophage-inducible expression of a model antigen in *Salmonella typhimurium* enhances immunogenicity. Proceedings of the National Academy of Sciences of the United States of America. 1995; 92(7):2904-8.

176. Huang, Jen-Min, Michela Sali, Matthew W. Leckenby, David S. Radford, Hong A. Huynh, Giovanni Delogu, Rocky M. Cranenburgh, and Simon M. Cutting. "Oral delivery of a DNA vaccine against tuberculosis using operator-repressor titration in a *Salmonella enterica* vector." Vaccine 28, no. 47 (2010): 7523-7528.

177. Husseiny, Mohamed I., and Michael Hensel. "Evaluation of an intracellular-activated promoter for the generation of live *Salmonella* recombinant vaccines." Vaccine 23, no. 20 (2005): 2580-2590.

178. Jabbar, Ibtissam A., Germain J P Fernando, Nick Saunders, Anne Aldovini, Richard Young, Karen Malcolm, and Ian H. Frazer. "Immune responses induced by BCG recombinant for human papillomavirus Li and E7 proteins." Vaccine 18, no. 22 (2000): 2444-2453.

179. Jensen, Eric R., Hao Shen, Felix O. Wettstein, Rafi Ahmed, and Jeff F. Miller. "Recombinant *Listeria monocytogenes* as a live vaccine vehicle and a probe for studying cell-mediated immunity." Immunological reviews 158, no. 1 (1997): 147-157.

180. Jepson M A, Clark M A. The role of M cells in *Salmonella* infection. Microbes and infection. 2001; 3(14-15):1183-90.
181. Kapadia, Sagar U., John K. Rose, Elaine Lamirande, Leatrice Vogel, Kanta Subbarao, and Anjeanette Roberts. "Long-term protection from SARS coronavirus infection conferred by a single immunization with an attenuated VSV-based vaccine." Virology 340, no. 2 (2005): 174-182.
182. Kardani, K., Bolhassani, A. & Vaccine, S.-S. Prime-boost vaccine strategy against viral infections: Mechanisms and benefits. Vaccine (2016).
183. Karsten, Verena, Sean I. Murray, Jeremy Pike, Kimberly Troy, Martina Ittensohn, Manvel Kondradzhyan, K. Brooks Low, and David Bermudes. "msbB deletion confers acute sensitivity to CO2 in *Salmonella enterica* serovar Typhinurium that can be suppressed by a loss-of-function mutation in zwf." BMC microbiology 9, no. 1 (2009): 170.
184. Killeen, K., D. Spriggs, and J. Mekalanos. "Bacterial mucosal vaccines: *Vibrio cholerae* as a live attenuated vaccine/vector paradigm." In Defense of Mucosal Surfaces: Pathogenesis, Immunity and Vaccines, pp. 237-254. Springer, Berlin, Heidelberg, 1999.
185. Kim, K. S., M. C. Jenkins, and HYUN S. Lillehoj. "Immunization of chickens with live *Escherichia coli* expressing *Eimeria acervulina* merozoite recombinant antigen induces partial protection against coccidiosis." Infection and immunity 57, no. 8 (1989): 2434-2440.
186. Kotton, Camille N., and Elizabeth L. Hohmann. "Enteric pathogens as vaccine vectors for foreign antigen delivery." Infection and immunity 72, no. 10 (2004): 5535-5547.
187. Kuipers, Kirsten, Maria H. Daleke-Schermerhorn, Wouter S P Jong, M. Corinne, Fred van Opzeeland, Elles Simonetti, Joen Luirink, and Marien I. de Jonge. "*Salmonella* outer membrane vesicles displaying high densities of pneumococcal antigen at the surface offer protection against colonization." Vaccine 33, no. 17 (2015): 2022-2029.
188. Lau, Susanna K P, Patrick C Y Woo, Kenneth S M Li, Yi Huang, Hoi-Wah Tsoi, Beatrice H L Wong, Samson S Y Wong, Suet-Yi Leung, Kwok-Hung Chan, and Kwok-Yung Yuen. "Severe acute respiratory syndrome coronavirus-like virus in Chinese horseshoe bats." Proceedings of the National Academy of Sciences 102, no. 39 (2005): 14040-14045.
189. Lee A K, Detweiler C S, Falkow S. OmpR regulates the two-component system SsrA-ssrB in *Salmonella* pathogenicity island 2. Journal of bacteriology. 2000; 182(3): 771-81.
190. Lee, Jong-Soo, Kwang-Soon Shin, Jae-Gu Pan, and Chul-Joong Kim. "Surface-displayed viral antigens on *Salmonella* carrier vaccine." Nature biotechnology 18, no. 6 (2000): 645.
191. Li, Long, Weihuan Fang, Jianrong Li, Li Fang, Yaowei Huang, and Lian Yu. "Oral DNA vaccination with the polyprotein gene of infectious bursal disease virus (IBDV) delivered by attenuated *Salmonella* elicits protective immune responses in chickens." Vaccine 24,no.33-34(2006):5919-5927.
192. Li, Wendong, Zhengli Shi, Meng Yu, Wuze Ren, Craig Smith, Jonathan H. Epstein, Hanzhong Wang et al. "Bats are natural reservoirs of SARS-like coronaviruses." Science 310, no. 5748 (2005): 676-679.
193. Liljeqvist, Sissela, and Stefan Ståhl. "Production of recombinant subunit vaccines: protein immunogens, live delivery systems and nucleic acid vaccines." Journal of biotechnology 73, no. 1 (1999): 1-33.
194. Loessner, Holger, and Siegfried Weiss. "Bacteria-mediated DNA transfer in gene therapy and vaccination." Expert opinion on biological therapy 4, no. 2 (2004): 157-168.
195. Loessner, Holger, Anne Endmann, Sara Leschner, Heike Bauer, Andrea Zelmer, Susanne zur Lage, Kathrin Westphal, and Siegfried Weiss. "Improving live attenuated bacterial carriers for vaccination and therapy." International Journal of Medical Microbiology 298, no. 1-2 (2008):21-26.
196. Low, Kenneth Brooks, Martina Ittensohn, Xiang Luo, Li-Mou Zheng, Ivan King, John M. Pawelek, and David Bermudes. "Construction of VNP20009." In Suicide Gene Therapy, pp. 47-59. Humana Press, 2004.
197. Luke, C. J. & review of vaccines, S.-K. Improving pandemic H5N1 influenza vaccines by combining different vaccine platforms. Expert review of vaccines, doi: 10.1586/14760584.2014.922416 (2014).
198. Makvandi, Manoochehr, Ali Teimoori, Mehdi Parsa Nahad, Ali Khodadadi, and Milad Zandi. "Expression of *Salmonella typhimurium* and *Escherichia coli* flagellin protein and its functional characterization as an adjuvant." Microbial pathogenesis 118 (2018): 87-90.
199. McSorley, Stephen J., Damo Xu, and FYs Liew. "Vaccine efficacy of *Salmonella* strains expressing glycoprotein 63 with different promoters." Infection and immunity 65, no. 1 (1997): 171-178.
200. Metzger, Wolfram G., E. Mansouri, M. Kronawitter, Susanne Diescher, Meike Soerensen, Robert Hurwitz, Dirk Bumann, Toni Aebischer, B-U. Von Specht, and Thomas F. Meyer. "Impact of vector-priming on the immunogenicity of a live recombinant *Salmonella enterica* serovar *typhi* Ty21a vaccine expressing urease A and B from *Helicobacter pylori* in human volunteers." Vaccine 22, no. 17-18 (2004): 2273-2277.
201. Mielcarek, Nathalie, Sylvie Alonso, and Camille Locht. "Nasal vaccination using live bacterial vectors." Advanced drug delivery reviews 51, no. 1-3 (2001): 55-69.
202. Miller S I, Pulkkinen W S, Selsted M E, Mekalanos J J. Characterization of defensin resistance phenotypes associated with mutations in the phoP virulence regulon of *Salmonella typhimurium*. Infection and immunity. 1990; 58(11):3706-10.
203. Mohamadzadeh, Mansour, Tri Duong, Timothy Hoover, and Todd R. Klaenhammer. "Targeting mucosal dendritic cells with microbial antigens from probiotic lactic acid bacteria." Expert review of vaccines 7, no. 2 (2008): 163-174.
204. Nagarajan, Arvindhan G., Sudhagar V. Balasundaram, Jessin Janice, Guruswamy Karnam, Sandeepa M. Eswarappa, and Dipshikha Chakravortty. "SopB of *Salmonella enterica* serovar *Typhimurium* is a potential DNA vaccine candidate in conjugation with live attenuated bacteria." Vaccine 27, no. 21 (2009): 2804-2811.
205. Niedergang, Florence, Jean-Claude Sirard, Corinne Tallichet Blanc, and Jean-Pierre Kraehenbuhl. "Entry and survival of *Salmonella typhimurium* in dendritic cells and presentation of recombinant antigens do not require macrophage-specific virulence factors." Proceedings of the National Academy of Sciences 97, no. 26 (2000): 14650-14655.
206. Oggioni, Marco R., Riccardo Manganelli, Mario Contorni, Massimo Tommasino, and Gianni Pozzi. "Immunization of mice by oral colonization with live recombinant commensal streptococci." Vaccine 13, no. 8 (1995): 775-779.

207. Okan, Nihal A., Patricio Mena, Jorge L. Benach, James B. Bliska, and A. Wali Karzai. "The smpB-ssrA mutant of *Yersinia pestis* functions as a live attenuated vaccine to protect mice against pulmonary plague infection." Infection and immunity 78, no. 3 (2010): 1284-1293.

208. Ou, Junxian, Zhonghua Zhou, Jing Zhang, Wendong Lan, Shan Zhao, Jianguo Wu, Donald Seto, Gong Zhang, and Qiwei Zhang. "RBD mutations from circulating SARS-CoV-2 strains enhance the structural stability and human ACE2 affinity of the spike protein." bioRxiv (2020).

209. Ou, X., Liu, Y., Lei, X. et al. Characterization of spike glycoprotein of SARS-CoV-2 on virus entry and its immune cross-reactivity with SARS-CoV. Nat Commun 11, 1620 (2020). doi.org/10.1038/s41467-020-15562-9

210. Pace, John Lee, Richard Ives Walker, and Steven Michael Frey. "Methods for producing enhanced antigenic *campylobacter* bacteria and vaccines." U.S. Pat. No. 5,679,564, issued Oct. 21, 1997.

211. Paglia, Paola, Ivano Arioli, Nicole Frahm, Trinad Chakraborty, Mario P. Colombo, and Carlos A. Guzmàn. "The defined attenuated *Listeria monocytogenes* Ampl2 mutant is an effective oral vaccine carrier to trigger a long-lasting immune response against a mouse fibrosarcoma." European journal of immunology 27, no. 6 (1997): 1570-1575.

212. Panthel, K., Meinel, K. M., Sevil Domenech, V. E. E., Trülzsch, K. & Riissmann, H. *Salmonella* type III-mediated heterologous antigen delivery: a versatile oral vaccination strategy to induce cellular immunity against infectious agents and tumors. International journal of medical microbiology: IJMM 298, 99-103, doi:10.1016/j.ijmm.2007.07.002 (2008).

213. Pasetti, Marcela F., Myron M. Levine, and Marcelo B. Sztein. "Animal models paving the way for clinical trials of attenuated *Salmonella enterica* serovar *Typhi* live oral vaccines and live vectors." Vaccine 21, no. 5-6 (2003): 401-418.

214. Paterson, Yvonne, Patrick D. Guirnalda, and Laurence M. Wood. "*Listeria* and *Salmonella* bacterial vectors of tumor-associated antigens for cancer immunotherapy." In Seminars in immunology, vol. 22, no. 3, pp. 183-189. Academic Press, 2010.

215. Paterson, Yvonne. "Specific immunotherapy of cancer using a live recombinant bacterial vaccine vector." U.S. Pat. No. 6,051,237, issued Apr. 18, 2000.

216. Patyar, S., R. Joshi, D S Prasad Byrav, A. Prakash, B. Medhi, and B. K. Das. "Bacteria in cancer therapy: a novel experimental strategy." Journal of biomedical science 17, no. 1 (2010): 21.

217. Pawelek, John M., K. Brooks Low, and David Bermudes. "Tumor-targeted *Salmonella* as a novel anticancer vector." Cancer research 57, no. 20 (1997): 4537-4544.

218. Poltorak A, He X, Smirnova I, Liu M Y, Van Huffel C, Du X, et al. Defective LPS signaling in C3H/HeJ and C57BL/10ScCr mice: mutations in Tlr4 gene. Science (New York, N.Y.). 1998; 282(5396):2085-8.

219. Prisco, A. & concepts, D. P. Memory immune response: a major challenge in vaccination. Biomolecular concepts (2012).

220. Qu, Daofeng, Suhua Wang, Weiming Cai, and Aifang Du. "Protective effect of a DNA vaccine delivered in attenuated *Salmonella typhimurium* against *Toxoplasma gondii* infection in mice." Vaccine 26, no. 35 (2008): 4541-4548.

221. Reveneau, Nathalie, Marie-Claude Geoffroy, Camille Locht, Patrice Chagnaud, and Annick Mercenier. "Comparison of the immune responses induced by local immunizations with recombinant *Lactobacillus plantarum* producing tetanus toxin fragment C in different cellular locations." Vaccine 20, no. 13-14 (2002): 1769-1777.

222. Robinson, Karen, Lisa M. Chamberlain, Karin M. Schofield, Jeremy M. Wells, and Richard W F Le Page. "Oral vaccination of mice against tetanus with recombinant *Lactococcus lactis*." Nature biotechnology 15, no. 7 (1997): 653.

223. Rosenkranz, Claudia D., Damasia Chiara, Caroline Agorio, Adriana Baz, Marcela F. Pasetti, Fernanda Schreiber, Silvia Dematteis, Miguel Martinez, Marcelo B. Sztein, and Jose A. Chabalgoity. "Towards new immunotherapies: targeting recombinant cytokines to the immune system using live attenuated *Salmonella*." Vaccine 21, no. 7-8 (2003): 798-801.

224. Ross, Bruce C., Larissa Czajkowski, Dianna Hocking, Mai Margetts, Elizabeth Webb, Linda Rothel, Michelle Patterson et al. "Identification of vaccine candidate antigens from a genomic analysis of *Porphyromonas gingivalis*." Vaccine 19, no. 30 (2001): 4135-4142.

225. Rota P A, Khan A S, Durigon E, Yuran T, Villamarzo Y S, Bellini W J. 1995. Detection of measles virus RNA in urine specimens from vaccine recipients. J Clin Microbiol 33:2485-2488.

226. Ryan, Edward T., Joan R. Butterton, Rex Neal Smith, Patricia A. Carroll, Thomas I. Crean, and Stephen B. Calderwood. "Protective immunity against *Clostridium difficile* toxin A induced by oral immunization with a live, attenuated *Vibrio cholerae* vector strain." Infection and immunity 65, no. 7 (1997): 2941-2949.

227. Santos, Renato L., Shuping Zhang, Renée M. Tsolis, Robert A. Kingsley, L. Garry Adams, and Andreas J. Bäumler. "Animal models of *Salmonella* infections: enteritis versus typhoid fever." Microbes and Infection 3, no. 14-15 (2001): 1335-1344.

228. Sbrogio-Almeida, M. E., Tainá Mosca, L. M. Massis, I. A. Abrahamsohn, and L. C. S. Ferreira. "Host and bacterial factors affecting induction of immune responses to flagellin expressed by attenuated *Salmonella* vaccine strains." Infection and immunity 72, no. 5 (2004): 2546-2555.

229. Schorr, Joachim, Bernhard Knapp, Erika Hundt, Hans A. Küpper, and Egon Amann. "Surface expression of malarial antigens in *Salmonella typhimurium*: induction of serum antibody response upon oral vaccination of mice." Vaccine 9, no. 9 (1991): 675-681.

230. Seegers, Jos F M L. "Lactobacilli as live vaccine delivery vectors: progress and prospects." Trends in biotechnology 20, no. 12 (2002): 508-515.

231. Shams, Homayoun, Fernando Poblete, Holger Rüssmann, Jorge E. Galán, and Ruben O. Donis. "Induction of specific CD8+ memory T cells and long lasting protection following immunization with *Salmonella typhimurium* expressing a lymphocytic choriomeningitis MHC class I-restricted epitope." Vaccine 20, no. 3-4 (2001): 577-585.

232. Shen, Hao, Mark K. Slifka, Mehrdad Matloubian, Eric R. Jensen, Rafi Ahmed, and Jeff F. Miller. "Recombinant *Listeria monocytogenes* as a live vaccine vehicle for the induction of protective anti-viral cell-mediated immunity." Proceedings of the National Academy of Sciences 92, no. 9 (1995): 3987-3991.

233. Silin, Dmytro S., Oksana V. Lyubomska, Vichai Jirathitikal, and Aldar S. Bourinbaiar. "Oral vaccination: where we are?." Expert opinion on drug delivery 4, no. 4 (2007): 323-340.

234. Silva, Adilson José da, Teresa Cristina Zangirolami, Maria Teresa Marques Novo-Mansur, Roberto de Campos Giordano, and Elizabeth Angélica Leme Martins. "Live bacterial vaccine vectors: an overview." Brazilian Journal of Microbiology 45, no. 4 (2014): 1117-1129.

235. Sjöstedt, A., G. Sandström, and A. Tärnvik. "Humoral and cell-mediated immunity in mice to a 17-kilodalton lipoprotein of *Francisella tularensis* expressed by *Salmonella typhimurium*." Infection and immunity 60, no. 7 (1992): 2855-2862.

236. Spreng, Simone, Guido Dietrich, and Gerald Weidinger. "Rational design of *Salmonella*-based vaccination strategies." Methods 38, no. 2 (2006): 133-143.

237. Srinivasan, Aparna, Joseph Foley, and Stephen J. McSorley. "Massive number of antigen-specific CD4 T cells during vaccination with live attenuated *Salmonella* causes interclonal competition." The Journal of Immunology 172, no. 11 (2004): 6884-6893.

238. Ståhl, Stefan, and Mathias Uhlén. "Bacterial surface display: trends and progress." Trends in biotechnology 15, no. 5 (1997): 185-192.

239. Stevenson, Gordon, and Paul A. Manning. "Galactose epimeraseless (GalE) mutant G30 of *Salmonella typhimurium* is a good potential live oral vaccine carrier for fimbrial antigens." FEMS microbiology letters 28, no. 3 (1985): 317-321.

240. Stocker, Bruce A D, and Salete M C Newton. "Immune responses to epitopes inserted in *Salmonella* flagellin." International reviews of immunology 11, no. 2 (1994): 167-178.

241. Stocker, Bruce A D. "Novel non-reverting *Salmonella* live vaccines." U.S. Pat. No. 4,735,801, issued Apr. 5, 1988.

242. Strindelius, Lena, Malin Filler, and Ingvar Sjöholm. "Mucosal immunization with purified flagellin from *Salmonella* induces systemic and mucosal immune responses in C3H/HeJ mice." Vaccine 22, no. 27-28 (2004): 3797-3808.

243. Su F, Patel G B, Hu S, Chen W. Induction of mucosal immunity through systemic immunization: Phantom or reality? Human vaccines & immunotherapeutics. 2016; 12(4):1070-9.

244. Sztein M B. Cell-mediated immunity and antibody responses elicited by attenuated *Salmonella enterica* Serovar *Typhi* strains used as live oral vaccines in humans. Clinical infectious diseases: an official publication of the Infectious Diseases Society of America. 2007; 45 Suppl 1:S15-9.

245. Takata, Tetsuo, Toshiro Shirakawa, Yoshiko Kawasaki, Shohiro Kinoshita, Akinobu Gotoh, Yasunobu Kano, and Masato Kawabata. "Genetically engineered *Bifidobacterium animalis* expressing the *Salmonella* flagellin gene for the mucosal immunization in a mouse model." The Journal of Gene Medicine: A cross-disciplinary journal for research on the science of gene transfer and its clinical applications 8, no. 11 (2006): 1341-1346.

246. Thanh Le T, Andreadakis Z., A. Kumar, R. Gomez Roman, S. Tollefsen, M. Saville, and S. Mayhew. "The COVID-19 vaccine development landscape." Nat Rev Drug Discov (2020): 10-10.

247. Thatte, Jayant, Satyajit Rath, and Vineeta Bal. "Immunization with live versus killed *Salmonella typhimurium* leads to the generation of an IFN-γ-dominant versus an IL-4-dominant immune response." International immunology 5, no. 11 (1993): 1431-1436.

248. Tite, J. P., X. M. Gao, C. M. Hughes-Jenkins, M. Lipscombe, D. O'Callaghan, G. Dougan, and F. Y. Liew. "Anti-viral immunity induced by recombinant nucleoprotein of influenza A virus. III. Delivery of recombinant nucleoprotein to the immune system using attenuated *Salmonella typhimurium* as a live carrier." Immunology 70, no. 4 (1990): 540.

249. Toussaint, Bertrand, Xavier Chauchet, Yan Wang, Benoit Polack, and Audrey Le Gouëllec. "Live-attenuated bacteria as a cancer vaccine vector." Expert review of vaccines 12, no.10(2013):1139-1154.

250. Van Immerseel, Filip, U. Methner, I. Rychlik, B. Nagy, P. Velge, G. Martin, N. Foster, Richard Ducatelle, and Paul A. Barrow. "Vaccination and early protection against non-host-specific *Salmonella* serotypes in poultry: exploitation of innate immunity and microbial activity." Epidemiology & Infection 133, no. 6 (2005): 959-978.

251. Wahid R, Pasetti M F, Maciel M, Jr., Simon J K, Tacket C O, Levine M M, et al. Oral priming with *Salmonella Typhi* vaccine strain CVD 909 followed by parenteral boost with the S. *Typhi* Vi capsular polysaccharide vaccine induces CD27+IgD-S. *Typhi*-specific IgA and IgG B memory cells in humans. Clinical immunology (Orlando, Fla.). 2011; 138(2):187-200.

252. Walker, Mark J., Manfred Rohde, Kenneth N. Timmis, and Carlos A. Guzman. "Specific lung mucosal and systemic immune responses after oral immunization of mice with *Salmonella typhimurium* aroA, *Salmonella typhi* Ty21a, and invasive *Escherichia coli* expressing recombinant pertussis toxin S1 subunit." Infection and immunity 60, no. 10 (1992): 4260-4268.

253. Wang J Y, Harley R H, Galen J E. Novel methods for expression of foreign antigens in live vector vaccines. Human vaccines & immunotherapeutics. 2013; 9(7): 1558-64.

254. Wang, Shifeng, Qingke Kong, and Roy Curtiss III. "New technologies in developing recombinant attenuated *Salmonella* vaccine vectors." Microbial pathogenesis 58 (2013): 17-28.

255. Wang, Shifeng, Yuhua Li, Huoying Shi, Wei Sun, Kenneth L. Roland, and Roy Curtiss. "Comparison of a regulated delayed antigen synthesis system with in vivo-inducible promoters for antigen delivery by live attenuated *Salmonella* vaccines." Infection and immunity 79,no.2(2011):937-949.

256. Wells, J. M., K. Robinson, L. M. Chamberlain, K. M. Schofield, and R. W. F. Le Page. "Lactic acid bacteria as vaccine delivery vehicles." Antonie Van Leeuwenhoek 70, no. 2-4 (1996):317-330.

257. Winter, Kaitlin, Li Xing, Audrey Kassardjian, and Brian J. Ward. "Vaccination against *Clostridium difficile* by use of an attenuated *Salmonella enterica* serovar *Typhimurium* vector (YS1646) protects mice from lethal challenge." Infection and immunity 87, no. 8 (2019): e00089-19.

258. Wu, Jane Y., Salete Newton, Amrit Judd, Bruce Stocker, and William S. Robinson. "Expression of immunogenic epitopes of hepatitis B surface antigen with hybrid flagellin proteins by a vaccine strain of *Salmonella*." Proceedings of the National Academy of Sciences 86, no. 12 (1989): 4726-4730.

259. Wyszyńska, Agnieszka, Patrycja Kobierecka, Jacek Bardowski, and Elżbieta Katarzyna Jagusztyn-Krynicka. "Lactic acid bacteria-20 years exploring their potential as 260. Xu, Fengfeng, Mei Hong, and Jeffrey B. Ulmer. "Immunogenicity of an HIV-1 gag DNA vaccine carried by attenuated *Shigella*." Vaccine 21, no. 7-8 (2003): 644-648.
261. Xu, Yigang, and Yijing Li. "Induction of immune responses in mice after intragastric administration of *Lactobacillus casei* producing porcine parvovirus VP2 protein." Applied and environmental microbiology 73, no. 21 (2007): 7041-7047.
262. Zegers, N. D., E. Kluter, H. van Der Stap, E. Van Dura, P. Van Dalen, M. Shaw, and L. Baillie. "Expression of the protective antigen of *Bacillus anthracis* by *Lactobacillus casei*: towards the development of an oral vaccine against anthrax." Journal of applied microbiology 87, no. 2 (1999): 309-314.
263. Zhang, Ling, Lifang Gao, Lijuan Zhao, Baofeng Guo, Kun Ji, Yong Tian, Jinguo Wang et al. "Intratumoral delivery and suppression of prostate tumor growth by attenuated *Salmonella enterica* serovar *typhimurium* carrying plasmid-based small interfering RNAs." Cancer research 67, no. 12 (2007): 5859-5864.
264. Zhao, Zhanqin, Yun Xue, Bin Wu, Xibiao Tang, Ruiming Hu, Yindi Xu, Aizhen Guo, and Huanchun Chen. "Subcutaneous vaccination with attenuated *Salmonella enterica* serovar *Choleraesuis* C500 expressing recombinant filamentous hemagglutinin and pertactin antigens protects mice against fatal infections with both *S. enterica* serovar *Choleraesuis* and *Bordetella bronchiseptica*." Infection and immunity 76, no. 5 (2008): 2157-2163.
265. Zhou, Zhimin, Penny Post, Rick Chubet, Katherine Holtz, Clifton McPherson, Martin Petric, and Manon Cox. "A recombinant baculovirus-expressed S glycoprotein vaccine elicits high titers of SARS-associated coronavirus (SARS-CoV) neutralizing antibodies in mice." Vaccine 24, no. 17 (2006): 3624-3631.

U.S. 20190017057; 20180271787; 20170157239; 20170051260; 20160222393; 20160028148; 20150017204; 20140220661; 20120142080; 20110223241; 20100136048; 20100135961; 20090169517; 20080124355; 20070009489; 20050255088; 20050249706; 20050052892; 20050036987; 20040219169; 20040042274; 20040037117; 20030170276; 20030113293; 20030109026; 20020026655; U.S. Pat. Nos. 10,286,051; 10,188,722; 10,141,626; 10,087,451; 9,878,023; 9,739,773; 9,737,592; 9,657,085; 9,616,114; 9,597,379; 9,593,339; 9,486,513; 9,421,252; 9,365,625; 9,315,817; 9,200,289; 9,200,251; 9,068,187; 8,956,859; 8,771,669; 8,647,642; 8,623,350; 8,524,220; 8,440,207; 8,241,623; 7,514,089; 7,452,531; 7,354,592; 7,211,843; 6,962,696; 6,934,176; 6,923,972; 6,863,894; 6,798,684; 6,685,935; 6,475,482; 6,447,784; 6,190,657; 6,080,849; 6,548,287; 20140256922; 20120108640; 20110318308; 20090215754; 20090169517; 20070298012; 20070110752; 20070004666; 20060115483; 20060104955; 20060089350; 20060025387; 20050267103; 20050249706; 20050112642; 20050009750; 20040229338; 20040219169; 20040058849; 20030143676; 20030113293; 20030031628; 20030022835; 20020151063; 20140220661; 20140212396; 20140186401; 20140178341; 20140155343; 20140093885; 20130330824; 20130295054; 20130209405; 20130130292; 20120164687; 20120142080; 20120128594; 20120093773; 20120020883; 20110275585; 20110111496; 20110111481; 20100239546; 20100189691; 20100136048; 20100135973; 20100135961; 20100092438; 20090300779; 20090180955; 20090175829; 20090123426; 20090053186; 20080311081; 20080124355; 20080038296; 20070110721; 20070104689; 20060083716; 20050026866; 20050008618; 20040202663; 20050255088; 20030109026; 20020026655; 20110223241; 20070009489; 20050036987; 20030170276; 20140148582; 20130345114; 20130287810; 20130164380; 20130164307; 20130078275; 20120225454; 20120177682; 20120148601; 20120144509; 20120083587; 20120021517; 20110274719; 20110268661; 20110165680; 20110091493; 20110027349; 20100172976; 20090317404; 20090220540; 20090123382; 20090117049; 20090117048; 20090117047; 20090068226; 20080249013; 20080206284; 20070202591; 20070191262; 20070134264; 20060127408; 20060057152; 20050118193; 20050069491; 20050064526; 20040234455; 20040202648; 20040054142; 20030170211; 20030059400; 20030036644; 20030009015; 20030008839; 20020176848; 20020102242; 20140205538; 20140112951; 20140086950; 20120244621; 20120189572; 20110104196; 20100233195; 20090208534; 20090136542; 20090028890; 20080260769; 20080187520; 20070031382; 20060140975; 20050214318; 20050214317; 20050112140; 20050112139; 20040266003; 20040115174; 20040009936; 20030153527; 20030125278; 20030045492; 8,828,681; 8,822,194; 8,784,836; 8,771,669; 8,734,779; 8,722,668; 8,715,641; 8,703,153; 8,685,939; 8,663,634; 8,647,642; 8,642,257; 8,623,350; 8,604,178; 8,591,862; 8,586,022; 8,568,707; 8,551,471; 8,524,220; 8,440,207; 8,357,486; 8,343,509; 8,323,959; 8,282,919; 8,241,623; 8,221,769; 8,198,430; 8,137,904; 8,066,987; 8,021,662; 8,008,283; 7,998,461; 7,955,600; 7,939,319; 7,915,218; 7,887,816; 7,842,290; 7,820,184; 7,803,531; 7,790,177; 7,786,288; 7,763,420; 7,754,221; 7,740,835; 7,736,898; 7,718,180; 7,700,104; 7,691,383; 7,687,474; 7,662,398; 7,611,883; 7,611,712; 7,588,771; 7,588,767; 7,514,089; 7,470,667; 7,452,531; 7,404,963; 7,393,525; 7,354,592; 7,344,710; 7,247,296; 7,195,757; 7,125,718; 7,084,105; 7,083,791; 7,015,027; 6,962,696; 6,923,972; 6,916,918; 6,863,894; 6,770,632; 6,685,935; 6,682,729; 6,506,550; 6,500,419; 6,475,482; 6,447,784; 6,207,648; 6,190,657; 6,150,170; 6,080,849; 6,030,624; 5,877,159, 4,190,495; 4,888,170; 4,968,619; 5,066,596; 5,098,998; 5,294,441; 5,330,753; 5,387,744; 5,424,065; 5,468,485; 5,527,678; 5,627,067; 5,628,996; 5,643,771; 5,654,184; 5,656,488; 5,662,905; 5,672,345; 5,679,880; 5,686,079; 5,695,983; 5,717,071; 5,731,196; 5,736,367; 5,747,028; 5,770,214; 5,773,007; 5,811,105; 5,824,538; 5,830,702; 5,837,509; 5,837,541; 5,840,483; 5,843,426; 5,855,879; 5,855,880; 5,869,066; 5,874,088; 5,877,159; 5,888,799; 6,024,961; 6,051,416; 6,077,678; 6,080,849; 6,100,388; 6,129,917; 6,130,082; 6,150,170; 6,153,203; 6,177,083; 6,190,657; 6,207,167; 6,245,338; 6,254,875; 6,284,477; 6,294,655; 6,337,072; 6,339,141; 6,365,163; 6,365,723; 6,365,726; 6,372,892; 6,383,496; 6,410,012; 6,413,523; 6,426,191; 6,444,445; 6,447,784; 6,471,964; 6,475,482; 6,495,661; 6,500,419; 6,506,550; 6,511,666; 6,531,313; 6,537,558; 6,541,623; 6,566,121; 6,593,147; 6,599,509; 6,610,300; 6,610,529; 6,653,128; 6,682,729; 6,685,935; 6,719,980; 6,737,521; 6,749,831; 6,752,994; 6,780,405; 6,825,028; 6,855,814; 6,863,894; 6,872,547; 6,887,483; 6,905,691; 6,913,753; 6,916,478; 6,923,958; 6,923,972; 6,962,696; 6,992,237; 6,994,860; 7,005,129; 7,018,835; 7,026,155; 7,045,336; 7,056,700; 7,063,850; 7,083,794; 7,094,410; 7,115,269; 7,144,580; 7,144,982; 7,183,105; 7,195,757; 7,226,588; 7,235,234; 7,264,812; 7,279,464; 7,341,725; 7,341,841; 7,341,860; 7,354,592; 7,393,525; 7,407,790; 7,425,438; 7,452,531; 7,459,161; 7,473,247; 7,510,717; 7,514,089; 7,514,415; 7,531,723; 7,541,043; 7,569,219; 7,569,552; 7,569,682; 7,588,767; 7,588,771; 7,601,804.; 7,622,107; 7,625,572; 7,657,380; 7,662,398; 7,666,656; 7,691,393; 7,695,725; 7,700,091; 7,700,104; 7,718,179; 7,732,187;

7,754,221; 7,758,876; 7,763,420; 7,772,386; 7,776,527; 7,794,734; 7,803,531; 7,803,990; 7,807,184; 7,807,456; 7,820,184; 7,829,104; 7,833,775; 7,842,289; 7,842,290; 7,850,958; 7,850,970; 7,871,604; 7,871,815; 7,871,816; 7,887,816; 7,919,081; 7,927,606; 7,930,107; 7,951,386; 7,951,786; 7,955,600; 7,960,518; 7,972,604; 7,985,573; 7,993,651; 8,012,466; 8,021,662; 8,021,848; 8,034,359; 8,043,857; 8,048,428; 8,049,000; 8,053,181; 8,053,421; 8,066,987; 8,071,084; 8,071,319; 8,076,099; 8,101,396; 8,114,409; 8,114,414; 8,124,068; 8,124,408; 8,133,493; 8,137,904; 8,147,820; 8,168,421; 8,173,773; 8,187,610; 8,202,516; 8,207,228; 8,211,431; 8,221,769; 8,227,584; 8,241,623; 8,241,631; 8,241,637; 8,257,713; 8,273,361; 8,287,883; 8,288,359; 8,318,661; 8,323,668; 8,323,959; 8,329,685; 8,337,832; 8,337,861; 8,343,509; 8,343,512; 8,349,586; 8,357,486; 8,357,533; 8,361,707; 8,367,055; 8,399,618; 8,440,207; 8,445,254; 8,445,426; 8,445,662; 8,460,666; 8,465,755; 8,470,551; 8,481,055; 8,501,198; 8,524,220; 8,551,497; 8,557,789; 8,568,707; 8,580,280; 8,586,022; 8,591,862; 8,609,114; 8,623,350; 8,628,776; 8,632,783; 8,633,305; 8,642,257; 8,642,656; 8,647,642; 8,658,350; 8,663,940; 8,669,355; 8,673,311; 8,679,505; 8,703,153; 8,715,929; 8,716,254; 8,716,343; 8,722,064; 8,748,150; 8,758,766; 8,771,669; 8,772,013; 8,778,683; 8,784,829; 8,784,836; 8,790,909; 8,840,908; 8,853,382; 8,859,256; 8,877,212; 8,883,147; 8,889,121; 8,889,150; 8,895,062; 8,916,372; 8,926,993; 8,937,074; 8,951,531; 8,956,618; 8,956,621; 8,956,859; 8,961,989; 8,980,279; 8,992,943; 9,005,665; 9,011,870; 9,012,213; 9,017,986; 9,023,635; 9,040,059; 9,040,233; 9,045,528; 9,045,742; 9,050,285; 9,050,319; 9,051,574; 9,056,909; 9,062,297; 9,068,187; 9,107,864; 9,140,698; 9,161,974; 9,163,219; 9,169,302; 9,173,930; 9,173,935; 9,173,936; 9,180,183; 9,181,546; 9,198,960; 9,200,251; 9,200,289; 9,205,142; 9,220,764; 9,248,177; 9,255,149; 9,255,283; 9,265,804; 9,267,108; 9,289,481; 9,297,015; 9,303,264; 9,309,493; 9,315,817; 9,320,787; 9,320,788; 9,333,251; 9,339,533; 9,358,283; 9,364,528; 9,365,625; 9,376,686; 9,408,880; 9,415,077; 9,415,098; 9,421,252; 9,428,572; 9,441,204; 9,453,227; 9,457,074; 9,457,077; 9,463,238; 9,474,831; 9,480,740; 9,481,884; 9,481,888; 9,486,513; 9,487,577; 9,492,534; 9,499,606; 9,504,750; 950692, 9,526,778; 9,529,005; 9,539,313; 9,540,407; 9,546,199; 9,549,956; 9,556,442; 9,561,270; 9,562,080; 9,562,837; 9,566,321; 9,566,322; 9,567,375; 9,580,478; 9,580,718; 9,592,283; 9,593,339; 9,597,379; 9,598,697; 9,603,799; 9,610,342; 9,616,114; 9,622,486; 9,636,386; 9,642,881; 9,642,904; 9,649,345; 9,651,559; 9,655,815; 9,657,085; 9,657,327; 9,662,385; 9,663,758; 9,670,270; 9,695,229; 9,714,426; 9,717,782; 9,730,996; 9,737,592; 9,737,601; 9,739,773; 9,750,802; 9,758,572; 9,764,021; 9,775,896; 9,795,641; 9,796,762; 9,801,930; 9,808,517; 9,814,772; 9,827,305; 9,844,592; 9,845,342; 9,855,336; 9,856,311; 9,867,785; 9,872,898; 9,878,023; 9,878,024; 9,878,043; 9,884,108; 9,885,051; 9,889,165; 9,901,082; 9,907,755; 9,907,845; 9,913,893; 9,925,257; 9,950,063; 9,986,724; 9,987,355; 9,994,809; 9,999,660; 20010014673; 20020025325; 20020028215; 20020044938; 20020068068; 20020076417; 20020077272; 20020081317; 20020086032; 20020086332; 20020090376; 20020132789; 20020146430; 20020151462; 20020156009; 20020176848; 20030017162; 20030023075; 20030045492; 20030065039; 20030068328; 20030100100; 20030108562; 20030108957; 20030124516; 20030125278; 20030130827; 20030152589; 20030153527; 20030157637; 20030166099; 20030166279; 20030170211; 20030170613; 20030176377; 20030180260; 20030180304; 20030180320; 20030185802; 20030186908; 20030190601; 20030190683; 20030190749; 20030194714; 20030194755; 20030194798; 20030198995; 20030198996; 20030199005; 20030199088; 20030199089; 20030202937; 20030203411; 20030203481; 20030207833; 20030211086; 20030211103; 20030211461; 20030211476; 20030211599; 20030219408; 20030219888; 20030224369; 20030224444; 20030232335; 20030235577; 20040005700; 20040009540; 20040009936; 20040013658; 20040013689; 20040023310; 20040033539; 20040052817; 20040053209; 20040077067; 20040121307; 20040121474; 20040126871; 20040131641; 20040132678; 20040137003; 20040156865; 20040192631; 20040202663; 20040213804; 20040228877; 20040229338; 20040237147; 20040258703; 20040258707; 20040265337; 20050008618; 20050010032; 20050026866; 20050042755; 20050048076; 20050075298; 20050106151; 20050106176; 20050129711; 20050163791; 20050175630; 20050180985; 20050222057; 20050229274; 20050232937; 20050233408; 20050249706; 20050249752; 20050255125; 20050271643; 20050271683; 20050281841; 20050287123; 20060018877; 20060019239; 20060074039; 20060078572; 20060083716; 20060115494; 20060121045; 20060121054; 20060140971; 20060140975; 20060147418; 20060147461; 20060153875; 20060171960; 20060182754; 20060189792; 20060193874; 20060233835; 20060240494; 20060246083; 20060257415; 20060269570; 20070031382; 20070031458; 20070037225; 20070048331; 20070059323; 20070104733; 20070104736; 20070110717; 20070116725; 20070122881; 20070128216; 20070134214; 20070134272; 20070141082; 20070154495; 20070169226; 20070189982; 20070258901; 20070281328; 20070286874; 20070298012; 20080008718; 20080020441; 20080038296; 20080063655; 20080095794; 20080107653; 20080112974; 20080124355; 20080131466; 20080138359; 20080181892; 20080188436; 20080193373; 20080213308; 20080241179; 20080241858; 20080254058; 20080261869; 20080286852; 20080311081; 20080317742; 20090017000; 20090017048; 20090028892; 20090053186; 20090074816; 20090081250; 20090081257; 20090104204; 20090117151; 20090117152; 20090123426; 20090142310; 20090148473; 20090169517; 20090169562; 20090180987; 20090181078; 20090196887; 20090214476; 20090227013; 20090253778; 20090263414; 20090263418; 20090285844; 20090297552; 20090297561; 20090304750; 20090305398; 20090324503; 20090324576; 20090324638; 20090324641; 20100047286; 20100055082; 20100055127; 20100068214; 20100092438; 20100092518; 20100099600; 20100129406; 20100135961; 20100136048; 20100136055; 20100136058; 20100137192; 20100166786; 20100166800; 20100172938; 20100172976; 20100189691; 20100196524; 20100209446; 20100226891; 20100226931; 20100226941; 20100233212; 20100233213; 20100239546; 20100272748; 20100272759; 20100285592; 20100291148; 20100297184; 20100297740; 20100303862; 20100310602; 20100322957; 20110008389; 20110014274; 20110020401; 20110021416; 20110052628; 20110059126; 20110064723; 20110064766; 20110070290; 20110086059; 20110104186; 20110110979; 20110111481; 20110111496; 20110123565; 20110183342; 20110195093; 20110200631; 20110201092; 20110201676; 20110206694; 20110209228; 20110212090; 20110213129; 20110217323; 20110243992; 20110256214; 20110268739; 20110275585; 20110281330; 20110287046; 20110293662; 20110312020; 20120003298; 20120009247; 20120014881; 20120027811; 20120036589; 20120039931; 20120039994; 20120058142; 20120071545; 20120077206; 20120093773; 20120093850; 20120093865; 20120100177; 20120107340; 20120115223; 20120121647; 20120135039; 20120135503; 20120141493; 20120142079; 20120142080; 20120144509; 20120164687; 20120189657; 20120189661; 20120208866; 20120225454; 20120237491; 20120237537; 20120237544;

20120258128; 20120258129; 20120258135; 20120276167; 20120282181; 20120282291; 20120288523; 20120294948; 20120301422; 20120315278; 20130004547; 20130018089; 20130040370; 20130058997; 20130064845; 20130078275; 20130078278; 20130084307; 20130095131; 20130096103; 20130101523; 20130110249; 20130121968; 20130149321; 20130156809; 20130177589; 20130177593; 20130217063; 20130236948; 20130251719; 20130266635; 20130267481; 20130273144; 20130302380; 20130315950; 20130330824; 20130336990; 20130337012; 20130337545; 20140004178; 20140004193; 20140010844; 20140017279; 20140017285; 20140037691; 20140056940; 20140065187; 20140093477; 20140093954; 20140099320; 20140112951; 20140134662; 20140155343; 20140178425; 20140186398; 20140186401; 20140187612; 20140193459; 20140206064; 20140212396; 20140220661; 20140234310; 20140234379; 20140271563; 20140271719; 20140294883; 20140322249; 20140322265; 20140322267; 20140322268; 20140335125; 20140341921; 20140341942; 20140341970; 20140341974; 20140356415; 20140369986; 20140370036; 20140370057; 20140371428; 20150017138; 20150017191; 20150017204; 20150030573; 20150037370; 20150050311; 20150056246; 20150071994; 20150093824; 20150125485; 20150125921; 20150132335; 20150140028; 20150140034; 20150140037; 20150165011; 20150174178; 20150182611; 20150184167; 20150190500; 20150196659; 20150202276; 20150204845; 20150218254; 20150219645; 20150225692; 20150238589; 20150258190; 20150265696; 20150273045; 20150316567; 20150321037; 20150335736; 20150343050; 20150376242; 20160000896; 20160022592; 20160030494; 20160045591; 20160054299; 20160058860; 20160074505; 20160090395; 20160101168; 20160103127; 20160108096; 20160136285; 20160136294; 20160158334; 20160158335; 20160169921; 20160175415; 20160175428; 20160193256; 20160193257; 20160199422; 20160199474; 20160206727; 20160208261; 20160213770; 20160220652; 20160222393; 20160228523; 20160228530; 20160243204; 20160250311; 20160263209; 20160289287; 20160317637; 20160324783; 20160324939; 20160346381; 20160354462; 20160366862; 20160367650; 20160369282; 20170007683; 20170014513; 20170015735; 20170021011; 20170028048; 20170042987; 20170042996; 20170051260; 20170072042; 20170080078; 20170081642; 20170081671; 20170095548; 20170106028; 20170106074; 20170114319; 20170129942; 20170136102; 20170136111; 20170143815; 20170145061; 20170145065; 20170151321; 20170157232; 20170157239; 20170174746; 20170182155; 20170191058; 20170209502; 20170216378; 20170240615; 20170246281; 20170258885; 20170290889; 20170290901; 20170304434; 20170318817; 20170327830; 20170340720; 20170350890; 20170360540; 20170368156; 20170368166; 20180008701; 20180021424; 20180028642; 20180028649; 20180043021; 20180044406; 20180049413; 20180050099; 20180066041; 20180066225; 20180071377; 20180087060; 20180099999; 20180104328; 20180140665; 20180147278; 20180164221; 20180168488; 20180168489; 20180168490; 20180169222; 20180169226; 20180185469; 20180193003; 20180193441; 20180206726; 20180206769; 20180221286; 20180221470; 20180236063; 20180243347; 20180243348; and EP0973911.

---

What is claimed is:

1. A live genetically engineered bacterium, selected from the group consisting of *Escherichia coli* and *Salmonella*, comprising a genetically engineered construct comprising a nucleic acid sequence encoding SEQ ID NO 015, a SARS-CoV-2 spike protein receptor binding domain (RBD) 488-525 epitope, the live genetically engineered bacterium being adapted for administration to a human or animal and colonization of at least one tissue under non-lethal conditions and the nucleic acid sequence having a prokaryotic promoter for expression of the SARS-Cov2 spike protein RBD 488-525 epitope by the live genetically engineered bacterium in the at least one tissue.

2. The live genetically engineered bacterium according to claim 1, wherein the nucleic acid sequence further encodes a bacterial secretion signal.

3. The live genetically engineered bacterium according to claim 1, which is *Escherichia coli* Nissel 1917.

4. The live genetically engineered bacterium according to claim 1, which is an attenuated *Salmonella typhimurium*.

5. The live genetically engineered bacterium according to claim 1, wherein the nucleic acid sequence encodes SEQ ID NO 001.

6. The live genetically engineered bacterium according to claim 1, wherein the nucleic acid sequence further comprises a fused in-frame adjuvant peptide encoding sequence.

7. The live genetically engineered bacterium according to claim 6, wherein the adjuvant peptide encoding sequence encodes a p28 dimer.

8. The live genetically engineered bacterium according to claim 6, wherein the adjuvant peptide encoding sequence encodes an adjuvant selected from the group consisting of flagellin, a flagellin peptide that binds to a toll-like receptor, a combination of p28 and flagellin toll-like receptor binding region, a dimer of C3d p28, and a dimer of C3d p28 with an internal flagellin peptide.

9. The live genetically engineered bacterium according to claim 1, wherein the live genetically engineered bacterium expresses a gut colonization factor.

10. The live genetically engineered bacterium according to claim 1, wherein the gut colonization factor is selected from the group consisting of colicin A, E1, E2, E3, E4, E5, E6, E7, E8, E9, DF13, K, N, U, B, D, Ia, and M.

11. The live genetically engineered bacterium according to claim 1, wherein the nucleic acid sequence further encodes at least one of an angiotensin converting enzyme 2 binding peptide and an angiotensin binding protein 2.

12. The live genetically engineered bacterium according to claim 1, wherein the nucleic acid sequence further encodes a fusion protein selected from the group consisting of YebF, ice nucleation protein, and HlyA.

13. The live genetically engineered bacterium according to claim 12, wherein the fusion protein contains one or more disulfide bonds.

14. The live genetically engineered bacterium according to claim 1, wherein the live genetically engineered bacterium co-expresses a colicin immunity peptide and a colicin lysis peptide with the SARS-Cov2 spike protein RBD 488-525 epitope.

15. A genetically engineered bacterium selected from the group consisting of *Escherichia coli* and *Salmonella*, comprising:
   a first genetically engineered construct comprising a nucleic acid sequence encoding SEQ ID NO 015, a SARS-CoV-2 spike protein receptor binding domain (RBD) 488-525 epitope, having an associated bacterial expression promoter; and
   a second genetically engineered construct comprising a nucleic acid sequence encoding an adjuvant peptide.

16. The genetically engineered bacterium according to claim 15, wherein the SARS-CoV-2 spike protein RBD 488-525 epitope and the adjuvant peptide are together expressed as a fusion peptide.

17. A method of vaccinating a human against SARS-CoV-2, comprising:
   administering the live genetically engineered bacterium according to claim 1 orally, intranasally, or rectally to the human or animal;
   allowing the live genetically engineered bacterium to colonize a tissue of the human or animal; and
   clearing the live genetically engineered bacterium from the human or animal,
   wherein said administration, colonization, and clearance are non-lethal to the human or animal.

* * * * *